(12) United States Patent
Seidel et al.

(10) Patent No.: US 7,629,113 B2
(45) Date of Patent: *Dec. 8, 2009

(54) MULTIPLE SEXED EMBRYO PRODUCTION SYSTEM FOR BOVINE MAMMALS

(75) Inventors: George Seidel, La Porte, CO (US); Lisa Herickhoff, Fort Collins, CO (US); John Schenk, Fort Collins, CO (US)

(73) Assignee: XY, Inc, Navasota, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 10/081,955

(22) Filed: Feb. 20, 2002

(65) Prior Publication Data

US 2002/0119558 A1    Aug. 29, 2002

Related U.S. Application Data

(63) Continuation of application No. 09/448,643, filed on Nov. 24, 1999, now Pat. No. 6,372,422, which is a continuation of application No. 09/015,454, filed on Jan. 29, 1998, now Pat. No. 6,071,689, which is a continuation-in-part of application No. 09/001,394, filed on Dec. 31, 1997, now Pat. No. 6,149,867.

(51) Int. Cl.
*A61D 19/02* (2006.01)
*A01N 1/00* (2006.01)
*A01K 67/00* (2006.01)
*A61K 35/52* (2006.01)
*A61K 35/48* (2006.01)
*G01N 33/00* (2006.01)
*C12Q 1/68* (2006.01)

(52) U.S. Cl. .................. 435/2; 435/4; 435/6; 435/7.1; 435/7.21; 422/73; 436/63; 424/561; 800/15; 600/33; 600/35

(58) Field of Classification Search .......... 435/2, 435/6, 7.1, 7.21, 325; 600/33, 8, 35; 422/73, 422/82.5; 436/10, 18, 63.164; 209/576, 209/571
See application file for complete search history.

(56) References Cited

U.S. PATENT DOCUMENTS

| | | | |
|---|---|---|---|
| 3,005,756 A | 10/1961 | VanDemark et al. | |
| 3,299,354 A | 1/1967 | Hogg | |
| 3,499,435 A | 3/1970 | Rockwell et al. | |
| 3,547,526 A | 12/1970 | Devereux | |
| 3,644,128 A | 2/1972 | Lipner | |
| 3,661,460 A | 5/1972 | Elking et al. | |
| 3,687,806 A | 8/1972 | Van den Bovenkamp | 195/1.3 |
| 3,710,933 A | 1/1973 | Fulwyler et al. | |
| 3,738,759 A | 6/1973 | Dittrich et al. | |
| 3,756,459 A | 9/1973 | Bannister | |
| 3,761,187 A | 9/1973 | Dittrich et al. | |
| 3,761,941 A | 9/1973 | Robertson | |
| 3,788,744 A | 1/1974 | Friedman et al. | |
| 3,791,384 A | 2/1974 | Richter et al. | |
| 3,791,517 A | 2/1974 | Friendman | |
| 3,810,010 A | 5/1974 | Thom | |
| 3,816,249 A | 6/1974 | Bhattacharya | |
| 3,826,364 A | 7/1974 | Bonner et al. | |
| 3,829,216 A | 8/1974 | Persidsky | |
| 3,833,796 A | 9/1974 | Fetner et al. | |
| 3,877,430 A | 4/1975 | Wieder | |
| 3,893,766 A | 7/1975 | Hogg | |
| 3,894,529 A | 7/1975 | Shrimpton | 128/1 R |
| 3,906,929 A | 9/1975 | Augspurger | |
| 3,909,744 A | 9/1975 | Wisner et al. | |
| 3,944,917 A | 3/1976 | Hogg et al. | |
| 3,947,093 A | 3/1976 | Goshima et al. | |
| 3,960,449 A | 6/1976 | Carleton et al. | |
| 3,963,606 A | 6/1976 | Hogg | |
| 3,973,003 A | 8/1976 | Colas | |
| 3,973,196 A | 8/1976 | Hogg | |
| 4,006,360 A | 2/1977 | Mueller | |
| 4,007,087 A | 2/1977 | Ericsson | |
| 4,009,260 A | 2/1977 | Ericsson | |
| 4,014,611 A | 3/1977 | Simpson et al. | |
| 4,056,324 A | 11/1977 | Gohde | |
| 4,058,732 A | 11/1977 | Wieder | |
| 4,067,965 A | 1/1978 | Bhattacharya | |
| 4,070,617 A | 1/1978 | Kachel et al. | |
| 4,083,957 A | 4/1978 | Lang | |
| 4,085,205 A | 4/1978 | Hancock | |
| 4,092,229 A | 5/1978 | Bhattacharya | 204/180 R |
| 4,110,604 A | 8/1978 | Haynes et al. | |
| 4,148,718 A | 4/1979 | Fulwyler | |
| 4,155,831 A | 5/1979 | Bhattacharya | 207/299 R |
| 4,162,282 A | 7/1979 | Fulwyler et al. | |
| 4,175,662 A | 11/1979 | Zold | |
| 4,178,936 A | 12/1979 | Newcomb | |
| 4,179,218 A | 12/1979 | Erdmann et al. | |
| 4,189,236 A | 2/1980 | Hogg et al. | |
| 4,191,749 A | 3/1980 | Bryant | 424/105 |
| 4,200,802 A | 4/1980 | Salzman et al. | |

(Continued)

FOREIGN PATENT DOCUMENTS

BR         9704313        6/1999

(Continued)

OTHER PUBLICATIONS

Brink et al. Theriogenology. 1994. 41:168.*

(Continued)

*Primary Examiner*—Carla Myers

(57) ABSTRACT

Improved insemination systems particularly adapted to use for sex-selected sperm sorting include systems which achieve superovulation and then multiple embryo production with sexed embryos. These systems combine with other techniques, including techniques for enhanced sheath fluid and other strategies which minimize stress on the sperm cells, and, potentially, a 2.9 percent sodium citrate sheath solution for bovine species and a hepes bovine gamete media for equine species. Improved collection systems and techniques for the process are described so that commercial application of sperms samples as well as the resulting animals may be achieved.

9 Claims, 4 Drawing Sheets

U.S. PATENT DOCUMENTS

| | | |
|---|---|---|
| 4,225,229 A | 9/1980 | Gohde |
| 4,225,405 A | 9/1980 | Lawson .................. 204/180 R |
| 4,230,558 A | 10/1980 | Fulwyler |
| 4,251,733 A | 2/1981 | Hirleman, Jr. |
| 4,255,021 A | 3/1981 | Brunsden |
| 4,263,508 A | 4/1981 | Leary et al. |
| 4,267,268 A | 5/1981 | Nelson, Jr. |
| 4,274,408 A | 6/1981 | Nimrod |
| 4,274,740 A | 6/1981 | Eidenschink et al. |
| 4,276,139 A | 6/1981 | Lawson .................. 204/180 R |
| 4,302,166 A | 11/1981 | Fulwyler et al. |
| 4,317,520 A | 3/1982 | Lombardo et al. |
| 4,318,480 A | 3/1982 | Lombardo et al. |
| 4,318,481 A | 3/1982 | Lombardo et al. |
| 4,318,482 A | 3/1982 | Barry et al. |
| 4,325,483 A | 4/1982 | Lombardo et al. |
| 4,327,177 A | 4/1982 | Shrimpton |
| 4,339,434 A | 7/1982 | Ericsson .................... 424/105 |
| 4,341,471 A | 7/1982 | Hogg et al. |
| 4,348,107 A | 9/1982 | Leif |
| 4,350,410 A | 9/1982 | Minott |
| 4,352,558 A | 10/1982 | Eisert |
| 4,361,400 A | 11/1982 | Gray et al. |
| 4,362,246 A | 12/1982 | Adair ......................... 209/3.3 |
| 4,367,043 A | 1/1983 | Sweet et al. |
| 4,395,397 A | 7/1983 | Shapiro |
| 4,395,676 A | 7/1983 | Hollinger et al. |
| 4,400,764 A | 8/1983 | Kenyon |
| 4,408,877 A | 10/1983 | Lindmo et al. |
| 4,422,761 A | 12/1983 | Frommer |
| 4,448,767 A | 5/1984 | Bryant ......................... 424/85 |
| 4,474,875 A | 10/1984 | Shrimpton |
| 4,487,320 A | 12/1984 | Auer |
| 4,492,436 A | 1/1985 | Bergmann |
| 4,498,766 A | 2/1985 | Unterleitner |
| 4,501,366 A | 2/1985 | Thompson |
| 4,511,661 A | 4/1985 | Goldberg .................... 436/503 |
| 4,515,274 A | 5/1985 | Hollinger et al. |
| 4,523,809 A | 6/1985 | Taboada et al. |
| 4,538,733 A | 9/1985 | Hoffman |
| 4,545,677 A | 10/1985 | Chupp |
| 4,559,309 A | 12/1985 | Evenson |
| 4,573,796 A | 3/1986 | Martin |
| 4,585,736 A | 4/1986 | Dolbeare et al. |
| 4,598,408 A | 7/1986 | O'Keefe |
| 4,600,302 A | 7/1986 | Sage, Jr. |
| 4,605,558 A | 8/1986 | Shrimpton |
| 4,609,286 A | 9/1986 | Sage, Jr. |
| 4,629,687 A | 12/1986 | Schindler et al. |
| 4,631,483 A | 12/1986 | Proni et al. |
| 4,637,691 A | 1/1987 | Uehara et al. |
| RE32,350 E | 2/1987 | Bhattacharya |
| 4,654,025 A | 3/1987 | Cassou et al. |
| 4,659,185 A | 4/1987 | Aughton |
| 4,660,971 A | 4/1987 | Sage et al. ..................... 356/39 |
| 4,661,913 A | 4/1987 | Wu et al. |
| 4,662,742 A | 5/1987 | Chupp |
| 4,673,288 A | 6/1987 | Thomas et al. |
| 4,673,289 A | 6/1987 | Gaucher |
| 4,680,258 A | 7/1987 | Hammerling et al. .......... 435/7 |
| 4,683,195 A | 7/1987 | Mullis et al. |
| 4,683,202 A | 7/1987 | Mullis |
| 4,691,829 A | 9/1987 | Auer |
| 4,698,142 A | 10/1987 | Muroi et al. .............. 204/182.3 |
| 4,702,598 A | 10/1987 | Böhmer |
| 4,704,891 A | 11/1987 | Recktenwald et al. |
| 4,710,635 A | 12/1987 | Chupp |
| 4,714,680 A | 12/1987 | Civin |
| 4,737,025 A | 4/1988 | Steen |
| 4,744,090 A | 5/1988 | Freiberg |
| 4,749,458 A | 6/1988 | Muroi et al. .............. 204/182.3 |
| 4,752,131 A | 6/1988 | Eisenlauer et al. |
| 4,756,427 A | 7/1988 | Gohde et al. |
| 4,758,729 A | 7/1988 | Monnin |
| 4,764,013 A | 8/1988 | Johnston |
| 4,765,737 A | 8/1988 | Harris et al. |
| 4,770,992 A | 9/1988 | den Engh et al. |
| 4,778,593 A | 10/1988 | Yamashita et al. |
| 4,780,406 A | 10/1988 | Dolbeare et al. |
| 4,780,451 A | 10/1988 | Donaldson |
| 4,786,165 A | 11/1988 | Yamamoto et al. |
| 4,790,653 A | 12/1988 | North, Jr. |
| 4,794,086 A | 12/1988 | Kasper et al. |
| 4,796,788 A | 1/1989 | Bond |
| 4,818,103 A | 4/1989 | Thomas et al. |
| 4,831,385 A | 5/1989 | Archer et al. |
| 4,836,038 A | 6/1989 | Baldwyn |
| 4,845,025 A | 7/1989 | Lary et al. |
| 4,846,785 A | 7/1989 | Cassou |
| 4,867,908 A | 9/1989 | Recktenwald et al. |
| 4,871,249 A | 10/1989 | Watson |
| 4,876,458 A | 10/1989 | Takeda et al. |
| 4,877,965 A | 10/1989 | Dandliker et al. |
| 4,887,721 A | 12/1989 | Martin et al. |
| 4,915,501 A | 4/1990 | Steen |
| 4,936,465 A | 6/1990 | Zold |
| 4,942,305 A | 7/1990 | Sommer |
| 4,954,715 A | 9/1990 | Zold |
| 4,957,363 A | 9/1990 | Takeda et al. |
| 4,959,354 A | 9/1990 | Barbetti |
| 4,965,204 A | 10/1990 | Civin |
| 4,979,093 A | 12/1990 | Laine et al. |
| 4,980,277 A | 12/1990 | Junnila |
| 4,981,580 A | 1/1991 | Auer |
| 4,983,038 A | 1/1991 | Ohki et al. |
| 4,987,539 A | 1/1991 | Moore et al. |
| 4,988,619 A | 1/1991 | Pinkel .......................... 435/30 |
| 4,989,977 A | 2/1991 | North, Jr. |
| 4,999,283 A | 3/1991 | Zavos et al. ..................... 435/2 |
| 5,005,981 A | 4/1991 | Schulte et al. |
| 5,007,732 A | 4/1991 | Ohki et al. |
| 5,017,497 A | 5/1991 | De Grooth |
| 5,021,244 A | 6/1991 | Spaulding .................... 424/561 |
| 5,030,002 A | 7/1991 | North, Jr. |
| 5,034,613 A | 7/1991 | Denk et al. |
| 5,040,890 A | 8/1991 | North, Jr. |
| 5,043,591 A | 8/1991 | Ludlow et al. |
| 5,055,393 A | 10/1991 | Kwoh et al. |
| 5,057,413 A | 10/1991 | Terstappen et al. |
| 5,072,382 A | 12/1991 | Kamentsky |
| 5,076,472 A | 12/1991 | Gross et al. |
| 5,079,959 A | 1/1992 | Miyake et al. |
| 5,084,004 A | 1/1992 | Ranoux |
| 5,087,295 A | 2/1992 | Gross et al. |
| 5,088,816 A | 2/1992 | Tomioka et al. |
| 5,089,714 A | 2/1992 | Ludlow et al. |
| 5,098,657 A | 3/1992 | Blackford et al. |
| 5,101,978 A | 4/1992 | Marcus |
| 5,116,125 A | 5/1992 | Rigler |
| 5,127,729 A | 7/1992 | Oetliker et al. |
| 5,132,548 A | 7/1992 | Borden et al. |
| 5,135,759 A | 8/1992 | Johnson ....................... 424/561 |
| 5,138,181 A | 8/1992 | Lefevre et al. |
| 5,142,140 A | 8/1992 | Yamazaki et al. |
| 5,142,462 A | 8/1992 | Kashima |
| 5,144,224 A | 9/1992 | Larsen |
| 5,150,313 A | 9/1992 | van den Engh et al. |
| 5,158,889 A | 10/1992 | Hirako et al. |
| 5,159,397 A | 10/1992 | Kosaka et al. |
| 5,159,403 A | 10/1992 | Kosaka |
| 5,162,306 A | 11/1992 | Donaldson |
| 5,167,926 A | 12/1992 | Kimura et al. |
| 5,180,065 A | 1/1993 | Touge et al. |
| 5,182,617 A | 1/1993 | Yoneyama et al. |

| Patent Number | Date | Inventor(s) | Patent Number | Date | Inventor(s) |
|---|---|---|---|---|---|
| 5,195,979 A | 3/1993 | Schinkel et al. | 5,643,796 A | 7/1997 | Van den Engh et al. |
| 5,199,576 A | 4/1993 | Corio et al. | 5,650,847 A | 7/1997 | Maltsev et al. |
| 5,204,884 A | 4/1993 | Leary et al. | 5,658,751 A | 8/1997 | Yue et al. |
| 5,215,376 A | 6/1993 | Schulte et al. | 5,660,997 A | 8/1997 | Spaulding ............... 435/7.21 |
| 5,219,729 A | 6/1993 | Hodgen | 5,663,048 A | 9/1997 | Winkfein et al. |
| 5,247,339 A | 9/1993 | Ogino | 5,665,315 A | 9/1997 | Robert et al. |
| 5,259,593 A | 11/1993 | Orme et al. | 5,672,880 A | 9/1997 | Kain |
| 5,260,764 A | 11/1993 | Fukuda et al. | 5,674,743 A | 10/1997 | Ulmer |
| 5,274,240 A | 12/1993 | Mathies et al. | 5,675,401 A | 10/1997 | Wangler et al. |
| 5,275,787 A | 1/1994 | Yuguchi et al. | 5,682,038 A | 10/1997 | Hoffman |
| 5,298,967 A | 3/1994 | Wells | 5,684,575 A | 11/1997 | Steen |
| 5,315,122 A | 5/1994 | Pinsky et al. | 5,687,727 A | 11/1997 | Kraus et al. |
| 5,316,540 A | 5/1994 | McMannis | 5,690,815 A | 11/1997 | Krasnoff et al. |
| 5,317,162 A | 5/1994 | Pinsky et al. | 5,690,895 A | 11/1997 | Matsumoto et al. ........... 422/73 |
| 5,346,990 A | 9/1994 | Spaulding ............... 530/350 | 5,691,133 A | 11/1997 | Critser et al. |
| RE34,782 E | 11/1994 | Dandliker et al. | 5,693,534 A | 12/1997 | Alak et al. |
| 5,359,907 A | 11/1994 | Baker et al. | 5,696,157 A | 12/1997 | Wang et al. |
| 5,366,888 A | 11/1994 | Fry et al. | 5,699,152 A | 12/1997 | Fedor et al. |
| 5,367,474 A | 11/1994 | Auer et al. | 5,700,692 A | 12/1997 | Sweet ...................... 436/50 |
| 5,370,842 A | 12/1994 | Miyazaki et al. | 5,701,012 A | 12/1997 | Ho |
| 5,395,588 A | 3/1995 | North, Jr. et al. | 5,707,808 A | 1/1998 | Roslaniec et al. |
| 5,400,179 A | 3/1995 | Ito | 5,708,868 A | 1/1998 | Ishikawa |
| 5,412,466 A | 5/1995 | Ogino | 5,712,807 A | 1/1998 | Bangham |
| 5,437,987 A | 8/1995 | Teng et al. | 5,719,666 A | 2/1998 | Fukuda et al. |
| 5,439,362 A | 8/1995 | Spaulding ............... 424/185.1 | 5,719,667 A | 2/1998 | Miers |
| 5,444,527 A | 8/1995 | Kosaka | 5,726,009 A | 3/1998 | Connors et al. |
| 5,447,841 A | 9/1995 | Gray et al. | 5,726,364 A | 3/1998 | Van den Engh .......... 73/864.85 |
| 5,447,842 A | 9/1995 | Simons | 5,726,751 A | 3/1998 | Altendorf et al. |
| 5,452,054 A | 9/1995 | Dewa et al. | 5,730,941 A | 3/1998 | Lefevre et al. |
| 5,457,526 A | 10/1995 | Kosaka | 5,736,330 A | 4/1998 | Fulton |
| 5,461,145 A | 10/1995 | Kudo et al. | 5,739,902 A | 4/1998 | Gjelsnes et al. |
| 5,464,581 A | 11/1995 | Van den Engh | 5,745,308 A | 4/1998 | Spangenberg |
| 5,466,572 A | 11/1995 | Sasaki et al. .................. 435/2 | 5,747,349 A | 5/1998 | den Engh et al. |
| 5,467,189 A | 11/1995 | Kreikebaum et al. | 5,759,767 A | 6/1998 | Lakowicz et al. |
| 5,469,375 A | 11/1995 | Kosaka | 5,777,732 A | 7/1998 | Hanninen et al. |
| 5,471,294 A | 11/1995 | Ogino | 5,780,230 A | 7/1998 | Li et al. .................... 435/6 |
| 5,471,299 A | 11/1995 | Kaye et al. | 5,786,560 A | 7/1998 | Tatah et al. |
| 5,475,487 A | 12/1995 | Mariella, Jr. et al. | 5,790,692 A | 8/1998 | Price et al. |
| 5,480,774 A | 1/1996 | Hew et al. | 5,793,485 A | 8/1998 | Gourley |
| 5,480,775 A | 1/1996 | Ito et al. | 5,796,112 A | 8/1998 | Ichie |
| 5,483,469 A | 1/1996 | Van den Engh et al. ..... 364/555 | 5,798,276 A | 8/1998 | Haugland et al. |
| 5,488,469 A | 1/1996 | Yamamoto et al. | 5,799,830 A | 9/1998 | Carroll et al. |
| 5,492,534 A | 2/1996 | Athayde | 5,804,436 A | 9/1998 | Okun et al. |
| 5,494,795 A | 2/1996 | Guerry et al. | 5,815,262 A | 9/1998 | Schrof et al. |
| 5,495,719 A | 3/1996 | Gray, Jr. | 5,819,948 A | 10/1998 | Van den Engh |
| 5,496,272 A | 3/1996 | Chung et al. | 5,824,269 A | 10/1998 | Kosaka et al. |
| 5,503,994 A | 4/1996 | Shear et al. | 5,831,723 A | 11/1998 | Kubota et al. |
| 5,514,537 A | 5/1996 | Chandler ...................... 435/2 | 5,835,262 A | 11/1998 | Iketaki et al. |
| 5,523,573 A | 6/1996 | Hanninen et al. | 5,840,504 A | 11/1998 | Blecher |
| 5,532,155 A | 7/1996 | Ranoux | 5,844,685 A | 12/1998 | Gontin |
| 5,547,849 A | 8/1996 | Baer et al. | 5,846,737 A | 12/1998 | Kang |
| 5,548,395 A | 8/1996 | Kosaka | 5,866,344 A | 2/1999 | Georgiou |
| 5,548,661 A | 8/1996 | Price et al. | 5,868,767 A | 2/1999 | Farley et al. |
| 5,550,058 A | 8/1996 | Corio et al. | 5,872,627 A | 2/1999 | Miers |
| 5,556,764 A | 9/1996 | Sizto et al. | 5,873,254 A | 2/1999 | Arav |
| 5,558,998 A | 9/1996 | Hammond et al. | 5,874,266 A | 2/1999 | Paisson |
| 5,559,032 A | 9/1996 | Pomeroy et al. | 5,876,942 A | 3/1999 | Cheng et al. |
| 5,578,449 A | 11/1996 | Frasch et al. | 5,880,457 A | 3/1999 | Tomiyama et al. |
| 5,579,159 A | 11/1996 | Ito | 5,880,474 A | 3/1999 | Norton et al. |
| 5,584,982 A | 12/1996 | Dovichi et al. | 5,883,378 A | 3/1999 | Irish et al. |
| 5,589,457 A | 12/1996 | Wiltbank et al. | 5,888,730 A | 3/1999 | Gray et al. |
| 5,596,401 A | 1/1997 | Kusuzawa | 5,891,734 A | 4/1999 | Gill et al. |
| 5,601,234 A | 2/1997 | Larue | 5,893,843 A | 4/1999 | Rodrigues Claro |
| 5,601,235 A | 2/1997 | Booker et al. | 5,895,764 A | 4/1999 | Sklar et al. |
| 5,601,533 A | 2/1997 | Hancke et al. | 5,895,922 A | 4/1999 | Ho |
| 5,602,039 A | 2/1997 | Van den Engh ............. 436/164 | 5,899,848 A | 5/1999 | Haubrich |
| 5,602,349 A | 2/1997 | Van den Engh .......... 73/864.85 | 5,909,278 A | 6/1999 | Deka et al. |
| 5,608,519 A | 3/1997 | Gourley et al. | 5,912,257 A | 6/1999 | Prasad et al. |
| 5,620,842 A | 4/1997 | Davis et al. | 5,916,144 A | 6/1999 | Li et al. |
| 5,622,820 A | 4/1997 | Rossi | 5,916,449 A | 6/1999 | Ellwart et al. |
| 5,627,037 A | 5/1997 | Ward et al. | 5,917,733 A | 6/1999 | Bangham |
| 5,633,503 A | 5/1997 | Kosaka | 5,919,360 A | 7/1999 | Contaxis, III et al. |
| 5,641,457 A | 6/1997 | Vardanega | 5,919,621 A | 7/1999 | Brown ...................... 435/6 |

| | | | | | | |
|---|---|---|---|---|---|---|
| 5,934,885 A | 8/1999 | Farrell et al. | 6,416,190 B1 | 7/2002 | Grier et al. |
| 5,962,238 A | 10/1999 | Sizto et al. | 6,423,505 B1 | 7/2002 | Davis |
| 5,972,710 A | 10/1999 | Weigl et al. | 6,423,551 B1 | 7/2002 | Weiss et al. |
| 5,973,842 A | 10/1999 | Spangenberg | 6,432,638 B2 | 8/2002 | Dervan et al. |
| 5,985,216 A * | 11/1999 | Rens et al. .................... 422/73 | 6,452,372 B1 | 9/2002 | Husher et al. |
| 5,985,538 A | 11/1999 | Stachecki | 6,454,945 B1 | 9/2002 | Weigl et al. |
| 5,990,479 A | 11/1999 | Weiss et al. | 6,456,055 B2 | 9/2002 | Shinabe et al. |
| 5,991,028 A | 11/1999 | Cabib et al. | 6,463,314 B1 | 10/2002 | Haruna |
| 5,998,140 A | 12/1999 | Dervan et al. | 6,465,169 B2 | 10/2002 | Walderich et al. |
| 5,998,212 A | 12/1999 | Corio et al. | 6,473,176 B2 | 10/2002 | Basiji et al. |
| 6,002,471 A | 12/1999 | Quake | 6,482,652 B2 | 11/2002 | Furlong et al. |
| 6,003,678 A | 12/1999 | Van den Engh | 6,489,092 B1 | 12/2002 | Benjamin et al. |
| 6,042,025 A | 3/2000 | Crampton et al. | 6,495,333 B1 | 12/2002 | Willmann et al. |
| 6,042,249 A | 3/2000 | Spangenberg | 6,495,366 B1 | 12/2002 | Briggs |
| 6,050,935 A | 4/2000 | Ranoux et al. | 6,503,698 B1 | 1/2003 | Dobrinsky et al. |
| 6,071,689 A | 6/2000 | Seidel et al. .................... 435/2 | 6,511,853 B1 | 1/2003 | Kopf-Sill et al. |
| 6,079,836 A | 6/2000 | Burr et al. | 6,514,722 B2 | 2/2003 | Palsson et al. |
| 6,086,574 A | 7/2000 | Carroll et al. | 6,524,860 B1 * | 2/2003 | Seidel et al. .................. 436/63 |
| 6,087,352 A | 7/2000 | Trout | 6,528,802 B1 | 3/2003 | Koenig et al. |
| 6,090,947 A | 7/2000 | Dervan et al. | 6,534,308 B1 | 3/2003 | Palsson et al. |
| 6,097,485 A | 8/2000 | Lievan | 6,537,829 B1 | 3/2003 | Zarling et al. |
| 6,111,398 A | 8/2000 | Graham | 6,540,895 B1 | 4/2003 | Spence et al. |
| 6,117,068 A | 9/2000 | Gourley et al. | 6,563,583 B2 | 5/2003 | Ortyn et al. |
| 6,119,465 A | 9/2000 | Mullens et al. | 6,576,291 B2 | 6/2003 | Bawendi et al. |
| 6,120,735 A | 9/2000 | Zborowski et al. | 6,577,387 B2 | 6/2003 | Ross, III et al. |
| 6,128,133 A | 10/2000 | Bergmann | 6,580,504 B1 | 6/2003 | Ortyn et al. |
| 6,130,034 A | 10/2000 | Aitken | 6,587,203 B2 | 7/2003 | Colon |
| 6,132,961 A | 10/2000 | Gray et al. | 6,589,792 B1 | 7/2003 | Malachowski |
| 6,133,044 A | 10/2000 | Van den Engh | 6,590,911 B1 | 7/2003 | Spinelli et al. |
| 6,133,995 A | 10/2000 | Kubota | 6,596,143 B1 | 7/2003 | Wang et al. |
| 6,139,800 A | 10/2000 | Chandler | 6,596,499 B2 | 7/2003 | Jalink |
| 6,140,121 A | 10/2000 | Ellington et al. | 6,604,435 B2 | 8/2003 | Buchanan et al. |
| 6,143,535 A | 11/2000 | Paisson | 6,613,525 B2 | 9/2003 | Nelson et al. |
| 6,143,901 A | 11/2000 | Dervan | 6,617,107 B1 | 9/2003 | Dean |
| 6,146,837 A | 11/2000 | van de Winkel | 6,618,143 B2 | 9/2003 | Roche et al. |
| 6,149,867 A | 11/2000 | Seidel et al. .................... 422/73 | 6,618,679 B2 | 9/2003 | Loehrlein et al. |
| 6,153,373 A | 11/2000 | Benjamin et al. | 6,641,708 B1 | 11/2003 | Becker et al. |
| 6,154,276 A | 11/2000 | Mariella, Jr. | 6,642,018 B1 | 11/2003 | Koller et al. |
| 6,175,409 B1 | 1/2001 | Nielsen et al. | 6,658,357 B2 | 12/2003 | Chandler |
| 6,177,277 B1 | 1/2001 | Soini | 6,664,550 B2 | 12/2003 | Rader et al. |
| 6,193,647 B1 | 2/2001 | Beebe et al. | 6,667,830 B1 | 12/2003 | Iketaki et al. |
| 6,201,628 B1 | 3/2001 | Basiji et al. | 6,671,044 B2 | 12/2003 | Ortyn et al. |
| 6,207,392 B1 | 3/2001 | Weiss et al. | 6,673,095 B2 | 1/2004 | Nordquist |
| 6,208,411 B1 | 3/2001 | Vaez-Iravani | 6,674,525 B2 | 1/2004 | Bardell et al. |
| 6,211,477 B1 | 4/2001 | Cardott et al. | 6,698,627 B2 | 3/2004 | Garcia et al. |
| 6,214,560 B1 | 4/2001 | Yguerabide et al. | 6,700,130 B2 | 3/2004 | Fritz |
| 6,221,654 B1 | 4/2001 | Quake et al. | 6,703,621 B2 | 3/2004 | Wolleschensky |
| 6,221,671 B1 | 4/2001 | Groner et al. | 6,704,313 B1 | 3/2004 | Duret et al. |
| 6,238,920 B1 | 5/2001 | Nagai et al. | 6,706,163 B2 | 3/2004 | Seul et al. |
| 6,247,323 B1 | 6/2001 | Maeda | 6,707,555 B1 | 3/2004 | Kusuzawa et al. |
| 6,248,590 B1 | 6/2001 | Malachowski | 6,713,019 B2 | 3/2004 | Ozasa et al. |
| 6,256,096 B1 | 7/2001 | Johnson | 6,729,369 B2 | 5/2004 | Neas et al. |
| 6,263,745 B1 | 7/2001 | Buchanan et al. | 6,746,873 B1 | 6/2004 | Buchanan et al. |
| 6,283,920 B1 | 9/2001 | Eberle et al. | 6,752,298 B2 | 6/2004 | Garcia et al. |
| 6,296,810 B1 | 10/2001 | Ulmer | 6,753,161 B2 | 6/2004 | Koller et al. |
| 6,309,815 B1 | 10/2001 | Tash et al. | 6,761,286 B2 | 7/2004 | Py et al. |
| 6,316,234 B1 | 11/2001 | Bova | 6,761,288 B2 | 7/2004 | Garcia |
| 6,317,511 B1 | 11/2001 | Horiuchi | 6,767,706 B2 | 7/2004 | Quake |
| 6,322,901 B1 | 11/2001 | Bawendi et al. | 6,780,377 B2 | 8/2004 | Hall et al. |
| 6,323,632 B1 | 11/2001 | Husher et al. | 6,782,768 B2 | 8/2004 | Buchanan et al. |
| 6,326,144 B1 | 12/2001 | Bawendi et al. | 6,789,706 B2 | 9/2004 | Abergel et al. |
| 6,328,071 B1 | 12/2001 | Austin | 6,789,759 B2 | 9/2004 | Miyasaka et al. |
| 6,329,158 B1 | 12/2001 | Hoffman et al. | 6,793,387 B1 | 9/2004 | Neas et al. |
| 6,332,540 B1 | 12/2001 | Paul et al. | 6,813,017 B1 | 11/2004 | Hoffman et al. |
| 6,357,307 B2 | 3/2002 | Buchanan et al. | 6,819,411 B1 | 11/2004 | Sharpe et al. |
| 6,368,786 B1 | 4/2002 | Saint-Ramon et al. | 6,849,394 B2 | 2/2005 | Rozeboom et al. |
| 6,372,422 B1 * | 4/2002 | Seidel et al. .................... 435/2 | 6,849,423 B2 | 2/2005 | Mutz et al. |
| 6,372,506 B1 | 4/2002 | Norton | 6,861,265 B1 | 3/2005 | Van den Engh |
| 6,384,951 B1 | 5/2002 | Basiji et al. | 6,941,005 B2 | 9/2005 | Lary et al. |
| 6,395,305 B1 | 5/2002 | Buhr et al. | 7,015,310 B2 | 3/2006 | Remington et al. |
| 6,400,453 B1 | 6/2002 | Hansen | 7,094,527 B2 | 8/2006 | Seidel et al. |
| 6,411,835 B1 | 6/2002 | Modell et al. | 7,105,355 B2 | 9/2006 | Kurabayashi et al. |
| 6,411,904 B1 | 6/2002 | Chandler | 7,195,920 B2 | 3/2007 | Seidel et al. |

| | | | | | | |
|---|---|---|---|---|---|---|
| 7,208,265 | B1 | 4/2007 | Schenk | DE | 69028526 | | 2/1997 |
| 2001/0006416 | A1 | 7/2001 | Johnson | DE | 195 49 015 | C1 | 4/1997 |
| 2002/0047697 | A1 | 4/2002 | Husher et al. | DE | 198 82 943.3 | | 2/2001 |
| 2002/0058332 | A1 | 5/2002 | Quake et al. | EP | 0025296 | A2 | 3/1981 |
| 2002/0064809 | A1 | 5/2002 | Mutz et al. | EP | 0 046 345 | A2 | 2/1982 |
| 2002/0096123 | A1 | 7/2002 | Whittier et al. | EP | 0 068 404 | B1 | 1/1983 |
| 2002/0113965 | A1 | 8/2002 | Roche et al. | EP | 0071538 | A1 | 2/1983 |
| 2002/0115055 | A1 | 8/2002 | Matta | EP | 0 026 770 | B1 | 3/1983 |
| 2002/0119558 | A1 | 8/2002 | Seidel et al. | EP | 0 029 662 | B1 | 2/1984 |
| 2002/0131957 | A1 | 9/2002 | Gavin | EP | 0 025 296 | B1 | 5/1985 |
| 2002/0141902 | A1 | 10/2002 | Ozasa et al. | EP | 0140616 | | 5/1985 |
| 2002/0171827 | A1 | 11/2002 | van den Engh | EP | 0 158 147 | A2 | 10/1985 |
| 2002/0182590 | A1 | 12/2002 | Strange et al. | EP | 0160201 | A2 | 11/1985 |
| 2002/0186375 | A1 | 12/2002 | Asbury et al. | EP | 0189702 | A1 | 8/1986 |
| 2002/0186874 | A1 | 12/2002 | Price et al. | EP | 0 229 814 | B1 | 7/1987 |
| 2002/0198928 | A1 | 12/2002 | Bukshpan et al. | EP | 0 246 604 | A2 | 11/1987 |
| 2003/0002027 | A1 | 1/2003 | Fritz | EP | 0288029 | B1 | 4/1988 |
| 2003/0048433 | A1 | 3/2003 | Desjonqueres | EP | 0276166 | A2 | 7/1988 |
| 2003/0059764 | A1 | 3/2003 | Ravkin et al. | EP | 0 289 677 | A2 | 11/1988 |
| 2003/0059945 | A1 | 3/2003 | Dzekunov et al. | EP | 0 316 173 | A1 | 5/1989 |
| 2003/0078703 | A1 | 4/2003 | Potts | EP | 0 317 809 | A2 | 5/1989 |
| 2003/0096405 | A1 | 5/2003 | Takayama et al. | EP | A-0 366794 | | 5/1990 |
| 2003/0098421 | A1 | 5/2003 | Ho | EP | 0 409 293 | A2 | 1/1991 |
| 2003/0113765 | A1 | 6/2003 | Dempcy et al. | EP | 0461618 | | 12/1991 |
| 2003/0119050 | A1 | 6/2003 | Shai | EP | 0 463 562 | A1 | 1/1992 |
| 2003/0119206 | A1 | 6/2003 | Shai | EP | 0468100 | A1 | 1/1992 |
| 2003/0129091 | A1 | 7/2003 | Seidel et al. | EP | 0474 187 | A2 | 3/1992 |
| 2003/0157475 | A1 | 8/2003 | Schenk | EP | 0 316 172 | B1 | 7/1992 |
| 2003/0165812 | A1 | 9/2003 | Takayama et al. | EP | 0 316 171 | B1 | 9/1992 |
| 2003/0175917 | A1 | 9/2003 | Cumming | EP | 0570102 | A1 | 3/1993 |
| 2003/0175980 | A1 | 9/2003 | Hayenga et al. | EP | 0538786 | A | 4/1993 |
| 2003/0190681 | A1 | 10/2003 | Shai | EP | 0 279 000 | B1 | 7/1993 |
| 2003/0207461 | A1 | 11/2003 | Bell et al. | EP | 0 553 951 | A1 | 8/1993 |
| 2003/0209059 | A1 | 11/2003 | Kawano | EP | 0 288 029 | B1 | 1/1994 |
| 2004/0005582 | A1 | 1/2004 | Shipwash | EP | 0 381 694 | B1 | 6/1994 |
| 2004/0031071 | A1 | 2/2004 | Morris et al. | EP | 0 361 504 | B1 | 7/1994 |
| 2004/0034879 | A1 | 2/2004 | Rothstein et al. | EP | 606847 | A2 | 7/1994 |
| 2004/0049801 | A1 | 3/2004 | Seidel | EP | 0 289 200 | B2 | 8/1994 |
| 2004/0053243 | A1 | 3/2004 | Evans | EP | 0 555 212 | B1 | 10/1994 |
| 2004/0055030 | A1 | 3/2004 | Maxwell et al. | EP | 0 361 503 | B1 | 11/1994 |
| 2004/0061070 | A1 | 4/2004 | Hansen | EP | 0 696 731 | A2 | 2/1996 |
| 2004/0061853 | A1 | 4/2004 | Blasenheim | EP | 0 705 978 | A2 | 4/1996 |
| 2004/0062685 | A1 | 4/2004 | Norton et al. | EP | 0 711 991 | A1 | 5/1996 |
| 2004/0072278 | A1 | 4/2004 | Chou et al. | EP | 0 471 758 | B1 | 9/1996 |
| 2004/0107150 | A1 | 6/2004 | Neas et al. | EP | 0 736 765 | A1 | 10/1996 |
| 2004/0132001 | A1 | 7/2004 | Seidel et al. | EP | 0 545 284 | B1 | 2/1997 |
| 2005/0003472 | A1 | 1/2005 | Anzar | EP | 0 360 487 | B1 | 7/1997 |
| 2005/0011582 | A1 | 1/2005 | Haug | EP | 0 412 431 | B1 | 10/1997 |
| 2005/0064383 | A1 | 3/2005 | Bashkin et al. | EP | 0 526 131 | B1 | 1/1998 |
| 2005/0112541 | A1 | 5/2005 | Durack | EP | A-0 478155 | | 1/1998 |
| 2005/0214733 | A1 | 9/2005 | Graham | EP | 0 822 404 | A3 | 2/1998 |
| 2005/0244805 | A1 | 11/2005 | Ludwig et al. | EP | 0 822 401 | A2 | 4/1998 |
| 2005/0282245 | A1 | 12/2005 | Ludwig et al. | EP | 0781985 | A3 | 7/1998 |
| 2006/0118167 | A1 | 6/2006 | Neas et al. | EP | 0 556 748 | B1 | 10/1998 |
| 2006/0147894 | A1 | 7/2006 | Sowter | EP | 0 430 402 | B1 | 1/1999 |
| 2006/0203226 | A1 | 9/2006 | Roche et al. | EP | 0 529 666 | B1 | 4/2000 |
| 2006/0263829 | A1 | 11/2006 | Evans et al. | EP | 0 994 342 | A3 | 4/2000 |
| 2006/0281176 | A1 | 12/2006 | Seidel et al. | EP | 0 752 133 | B1 | 6/2000 |
| 2007/0026378 | A1 | 2/2007 | Schenk | EP | 1 018 644 | A2 | 7/2000 |
| 2007/0026379 | A1* | 2/2007 | Seidel et al. ............ 435/2 | EP | 1 118 268 | A1 | 7/2001 |
| 2007/0042342 | A1 | 2/2007 | Seidel et al. | EP | 1 147 774 | A1 | 10/2001 |
| 2007/0092860 | A1 | 4/2007 | Schenk | EP | 0 534 033 | B1 | 11/2001 |
| 2007/0017086 | A1 | 5/2007 | Evans et al. | EP | 0 925 494 | B1 | 12/2001 |
| 2007/0099171 | A1 | 5/2007 | Schenk | EP | 0 748 316 | B1 | 5/2002 |
| 2007/0099260 | A1 | 5/2007 | Seidel et al. | EP | 0 662 124 | B1 | 6/2002 |
| 2007/0248976 | A1 | 10/2007 | Harding | EP | 1 245 944 | A3 | 10/2002 |
| | | | | EP | 1 249 502 | A2 | 10/2002 |
| | | FOREIGN PATENT DOCUMENTS | | EP | 1250897 | A1 | 10/2002 |
| | | | | EP | 1 380 304 | A2 | 1/2004 |
| CA | | 1029833 | 4/1978 | EP | 1403633 | A3 | 4/2004 |
| CA | | 1 250 808 | 3/1989 | EP | 1 100 400 | B1 | 5/2004 |
| CA | | 2113957 A1 | 1/1994 | EP | 1 257 168 | B1 | 2/2005 |
| CN | | ZL 03109426.0 | 12/2005 | FR | 2574656 | A1 | 6/1986 |

| | | |
|---|---|---|
| FR | A-2 635453 | 2/1990 |
| FR | 2 647 668 A | 12/1990 |
| FR | 2699678 A1 | 6/1994 |
| GB | 1471019 | 4/1977 |
| GB | 2 121 976 A | 1/1984 |
| GB | 2 122 369 A | 1/1984 |
| GB | 2 125 181 A | 2/1984 |
| GB | 2 136 561 A | 9/1984 |
| GB | 2 137 352 A | 10/1984 |
| GB | 2145112 | 2/1985 |
| GB | 2 144 542 A | 3/1985 |
| GB | 2 153 521 A | 8/1985 |
| GB | 2 243 681 A | 11/1991 |
| GB | 2 360 360 A | 9/2001 |
| JP | 61139747 (A) | 6/1986 |
| JP | 61159135 (A) | 7/1986 |
| JP | 2024535 | 1/1990 |
| JP | 4126064 (A) | 4/1992 |
| JP | 4126065 (A) | 4/1992 |
| JP | 4126066 (A) | 4/1992 |
| JP | 4126079 (A) | 4/1992 |
| JP | 4126080 (A) | 4/1992 |
| JP | 4126081 (A) | 4/1992 |
| SU | 1056008 | 11/1983 |
| SU | 1260778 A1 | 9/1986 |
| WO | WO 84/01265 A1 | 4/1984 |
| WO | WO 85/04014 A1 | 9/1985 |
| WO | WO 88/07198 | 9/1988 |
| WO | WO 89/04470 A1 | 5/1989 |
| WO | WO 89/04471 A1 | 5/1989 |
| WO | WO 89/04472 A1 | 5/1989 |
| WO | WO 90/13315 A1 | 11/1990 |
| WO | WO 91/05236 | 4/1991 |
| WO | WO 92/08120 A1 | 5/1992 |
| WO | WO 92/17288 A1 | 10/1992 |
| WO | WO 93/10803 | 6/1993 |
| WO | WO 93/17322 A1 | 9/1993 |
| WO | WO 94/22001 A1 | 9/1994 |
| WO | WO 96/04542 A1 | 2/1996 |
| WO | WO 96/12171 | 4/1996 |
| WO | WO 96/12171 A2 | 4/1996 |
| WO | WO 96/12172 | 4/1996 |
| WO | WO 96/12173 A1 | 4/1996 |
| WO | WO 96/31764 | 10/1996 |
| WO | WO 96/33806 A1 | 10/1996 |
| WO | WO 97/29354 A1 | 8/1997 |
| WO | WO 97/30338 A1 | 8/1997 |
| WO | WO 97/35189 A1 | 9/1997 |
| WO | WO 97/43620 A1 | 11/1997 |
| WO | WO 98/34094 | 6/1998 |
| WO | WO 99/05504 | 7/1998 |
| WO | WO 98/48259 | 10/1998 |
| WO | WO 98/57152 A1 | 12/1998 |
| WO | WO 99/38883 | 5/1999 |
| WO | WO 99/33956 | 8/1999 |
| WO | WO 99/42810 | 8/1999 |
| WO | WO 99/44035 | 9/1999 |
| WO | WO 99/44037 A1 | 9/1999 |
| WO | WO 99/47906 A1 | 9/1999 |
| WO | WO 99/60397 A1 | 11/1999 |
| WO | WO 9957955 | 11/1999 |
| WO | WO 99/61888 A2 | 12/1999 |
| WO | WO 00/12204 | 3/2000 |
| WO | WO 00/36396 | 6/2000 |
| WO | WO 00/49387 | 8/2000 |
| WO | WO 00/54026 | 9/2000 |
| WO | WO 00/56444 | 9/2000 |
| WO | WO 00/06193 | 10/2000 |
| WO | WO 00/70080 | 11/2000 |
| WO | WO 01/02836 A1 | 1/2001 |
| WO | 0129538 | 4/2001 |
| WO | WO 01/28700 A1 | 4/2001 |
| WO | WO 01/37655 A1 | 5/2001 |
| WO | WO 01/40765 A2 | 6/2001 |
| WO | WO 01/40765 A3 | 6/2001 |
| WO | WO 01/42757 A2 | 6/2001 |
| WO | WO 01/51612 A1 | 7/2001 |
| WO | WO 01/61313 A2 | 8/2001 |
| WO | WO 01/68110 | 9/2001 |
| WO | WO 01/68226 A2 | 9/2001 |
| WO | WO 01/71348 A1 | 9/2001 |
| WO | WO 01/75161 A2 | 10/2001 |
| WO | WO 0175176 | 10/2001 |
| WO | WO 01/85913 A2 | 11/2001 |
| WO | WO 01/85913 A3 | 11/2001 |
| WO | WO 01/90295 A1 | 11/2001 |
| WO | WO 01/95815 A1 | 12/2001 |
| WO | WO 02/01189 A1 | 1/2002 |
| WO | WO 02/04666 A2 | 1/2002 |
| WO | WO 02/19594 | 3/2002 |
| WO | WO 02/20850 A2 | 3/2002 |
| WO | WO 02/21102 A2 | 3/2002 |
| WO | WO 02/23163 A1 | 3/2002 |
| WO | WO 02/25269 A2 | 3/2002 |
| WO | WO 0219943 A1 | 3/2002 |
| WO | WO 02/26114 A2 | 4/2002 |
| WO | WO 02/28311 A2 | 4/2002 |
| WO | WO 02/29106 A2 | 4/2002 |
| WO | WO 02/41906 A2 | 5/2002 |
| WO | WO 02/43486 A1 | 6/2002 |
| WO | WO 02/43574 A2 | 6/2002 |
| WO | WO 02/44319 A2 | 6/2002 |
| WO | WO 02/052244 A2 | 7/2002 |
| WO | WO 02/054044 A2 | 7/2002 |
| WO | WO 02/057775 A1 | 7/2002 |
| WO | WO 02/060880 A | 8/2002 |
| WO | WO 02/077637 A1 | 10/2002 |
| WO | WO 02/092161 A1 | 11/2002 |
| WO | WO 02/092247 A1 | 11/2002 |
| WO | WO 03/008102 A1 | 1/2003 |
| WO | WO 03/008937 A2 | 1/2003 |
| WO | WO 03/012403 A1 | 2/2003 |
| WO | WO 03/016875 A2 | 2/2003 |
| WO | WO 03/020877 A2 | 3/2003 |
| WO | WO 03/056330 A2 | 7/2003 |
| WO | WO 03/056335 A2 | 7/2003 |
| WO | WO 03/ 072765 A1 | 9/2003 |
| WO | WO 03/078065 A1 | 9/2003 |
| WO | WO 03/078972 A1 | 9/2003 |
| WO | WO 04/001401 | 12/2003 |
| WO | WO 2004/006916 A1 | 1/2004 |
| WO | WO 2004/009237 A1 | 1/2004 |
| WO | WO 2004/009237 A3 | 1/2004 |
| WO | WO 2004/012837 A1 | 2/2004 |
| WO | WO 2004/012837 A3 | 2/2004 |
| WO | WO 2004/017041 A2 | 2/2004 |
| WO | WO 2004/017041 A3 | 2/2004 |
| WO | WO 2004/024227 A2 | 3/2004 |
| WO | WO 2004/046712 A2 | 6/2004 |
| WO | WO 2004/059282 A2 | 7/2004 |
| WO | WO 2004/003697 A2 | 10/2004 |
| WO | WO 2004/087177 A1 | 10/2004 |
| WO | WO 2004/088283 A2 | 10/2004 |
| WO | WO 2004/104178 A2 | 12/2004 |
| WO | WO 2004/104178 A3 | 12/2004 |
| WO | WO 2005/094852 A2 | 10/2005 |
| WO | WO 2005/095590 A2 | 10/2005 |
| WO | WO 2005/095960 A1 | 10/2005 |
| WO | WO 2006/015056 A2 | 2/2006 |
| WO | WO 2006012597 A2 | 2/2006 |
| WO | WO 2006060770 A2 | 8/2006 |

| WO | WO 2007/016090 A2 | 2/2007 |

OTHER PUBLICATIONS

Seidel et al. 1978. Control of Reproduction in the Cow, JR Sreenan ed., pp. 268-280.*
Hawk et al. Journal Animal Sciences. 1986. 63: 551-560.*
Jafar et al. *Theriogenology*, vol. 46, pp. 191-200, 1996.*
Amann, R., et al., Prospects for Sexing Mammalian Sperm Colorado Associated University Press, Animal Reproduction Laboratory College of Veterinary Medicine and Biomedical Sciences, Colorado State University, Fort Collins, CO, 80523, 1982.
Amoah, E.A. and Gelaye, S. 1996. Biotechnological advances in goat reproduction. J. Anim. Sci. 75(2): 578-585.
Andersen, V.K., Aamdal, J. and Fougner, J.A. 1973. Intrauterine und tiefzervikale Insemination mit Gefriersperma bein Schat. Zuchthygiene. 8:113-118.
Baker, R.D., Dziuk, P.J. and Norton, H.W. 1968. Effect of volume of semen, number of sperm and drugs on transport of sperm in artificially inseminated gilts. J. Anim. Sci. 27:88-93.
Becker, S.E. and Johnson. A.L. 1992. Effects of gonadotropin releasing hormone infused in a pulsatile or continuous fashion on serum gonadotropin concentrations and ovulation in the mare. J. Anim. Sci. 70:1208-1215.
Bedford, S. J. and Hinrichs, K. 1994. The effect of insemination volume on pregnancy rates of pony mares. Theriogenology 42:571-578.
Berger, G.S. 1987. Intratubal insemination. Fert. Steril. 48:328-330.
Beyhan, Z., Welch, G.R. and First, N.L. 1998. Sexual dimorphism in IVF bovine embryos produced by sperm sorted by high-speed flow cytometry. Theriogenology. 49(1): 359. abstr.
Bracher, V. and Allen, W.R., Videoendoscopic Examination of the Mare's Uterus: Findings in Normal Fertile Mares, Equine Veterinary Journal, vol. 24 (1992), pp. 274-278.
Braselton, W.E. and McShan, W.H. 1970. Purification and properties of follicle stimulating and luteinizing hormones from horse pituitary glands. Arch. Biochem. Biophys. 139:45-48.
Brethour, J.R. and Jaeger, J.R., The Single Calf Heifer System, Kansas Agric. Sta. Rep of Progress 570, 1989.
Bristol, S.P. 1982. Breeding behavior of a stallion at pasture with 20 mares in synchronized estrus. J. Reprod. Fert. Suppl. 32:71.
Buchanan, B.R., et al, Insemination of Mares with Low Numbers of Either Unsexed or Sexed Spermatozoa, Theriogenology, vol. 53, pp. 1333-1344, (2000).
Burwash, L.D., Pickett, B.W., Voss, J.L. and Back, D.G. 1974. Relationship of duration of stems to pregnancy rate in normally cycling, non-lactating mares. J.A.V.M.A. 165:714-716.
Caslick, E.A., The Vulva and the Vulvo-vaginal Orifice and its Relation to Genital Health of the Thoroughbred Mare, Cornell Veterinarian, vol. 27, 1937, pp. 178-187.
Chin, W.W. and Boime, I. 1990. *In*: Glycoprotein Hormones. Serona Symp. Norwell, MA. pp. 19-20.
Chung, Y.G., Schenk, J.L., Herrickhoff, L.A. and Seidel, G.E. Jr. 1998. Artificial insemination of super ovulated heifers with 600,000 sexed sperm. J Anim. Sci. Suppl. 1. 836:215. abstr.
Clement, F., Vincent, P., Mahla, R., Meriaux, J.C. and Palmer, E. 1998. Which insemination fertilizes when several successive inseminations are performed before ovulation. $7^{th}$ Int. Symp. Eq. Repro. 151. abstr.
Cran, D.G. et al., Production of Lambs by Low Dose Intrauterine Insemination With Flow Cytometrically Sorted and Unsorted Semen, Aberdeen, AB21 9TN, UK Scottish Agricultural College, Craibstone, Bucksbum, Aberdeen. AB21 9YA, UK, Theriogenology, p. 267, 1997.
Cran, D.C., Johnson, L.A., Miller, N.G., Cochrane, D. and Polge, C. 1993. Production of bovine calves following separation of X- and Y-chromosome bearing sperm and in vitro fertilization. Vet. Rec. 132:40-41.
Curran, S. 1998. In: Equine Diagnostic Ultrasonography. Fetal gender determination. Rantanen & McKinnon. $1^{st}$ Ed. Williams and Wilkins. pp. 165-169.
Day, B.N., Abeydeera, L.R., Johnson, L.A., Welch, G.R., Wang, W.H., Cantley, T.C. and Rieke, A. 1998. Birth of piglets preselected for gender following in vitro fertilization of in vitro matured pig oocytes by X and Y bearing spermatozoa sorted by high-speed flow cytometry. Theriogenology. 49(1): 360. abstr.
Dean, P.N., Pinkel, D. and Mendelson, M.L. 1978. Hydrodynamic orientation of spermatozoa heads for flow cytometry. Biophys. J. 23:7-13.
Demick, D.S., Voss, J.L. and Pickett, B.W. 1976. Effect of cooling, storage, glycerinating and spermatozoa numbers on equine fertility. J. Anim. Sci. 43:633-637.
DenDaas, J.H.G., De Jong, G., Lansbergen, L.M.T.E. and Van Wagtendonk-De Leeuw, A.M. 1998. The relationship between the number of spermatozoa inseminated and the reproductive efficiency of dairy bulls. J Dairy Sci. 81: 1714-1723.
Donoghue, A.M., Byers, A.P., Johnston, L.A., Armstrong, D.L. and Wildt, D.E. 1996. Timing of ovulation after gonadotropin induction and its importance to successful intrauterine insemination in the tiger (Panthera tigris). J. Reprod. Fert. 107:53-58.
Douglas, R.H. 1979. Review of super ovulation and embryo transfer in the equine. Theriogenology. 11:33-46.
Douglas, R.H., Nuti, L. and Ginther, O.J. 1974. Induction of ovulation and multiple ovulations on seasonally-an-ovulatory mares with equine pituitary fractions. Theriogenology. 2(6): 133-142.
Duchamp, G., Bour, B., Combamous, Y. and Palmer, E. 1987. Alternative solutions to hCG induction of ovulation in the mare. J. Reprod. Fert. Suppl. 35:221-228.
Evans, M.J. and Irvine, C.H.G. 1977. Induction of follicular development, maturation and ovulation by gonadotropin releasing hormone administration to acrylic mares. Bio. Reprod. 16:452-462.
Fitzgerald, B.P., Peterson, K.D. and Silvia, P.J. 1993. Effect of constant administration of a gonadotropin-releasing hormone agonist on reproductive activity in mares: Preliminary evidence on suppression of ovulation during the breeding season. Am. J. Vet. Res. 54:1746-1751.
Fluharty, F.L., et al., Effects of Age at Weaning and Diet on Growth of Calves, Ohio Agri. Res. and Dev. Circular, 1996, 156:29.
Foulkes, J.A., Stewart, D.L. and Herbert, C.N. 1977. Artificial insemination of cattle using varying numbers of spermatozoa. Vet. Rec. 101:205.
Fugger, E.F., Clinical Experience with Flow Cytometric Separation of Human X- and Y-Chromosome Bearing Sperm, Theriogenology, vol. 52, pp. 1435-1440 (1999).
Fulvryler, M.J. 1965. Electronic separation of biological cells by volume. Science. 150:910.
Fulwyler, M.J. 1977. Hydrodynamic orientation of cells. J Histochem. Cytochem. 25:781-783.
Garner, D.L., Gledhill, B.L., Pinkel, D., Lake, S., Stephenson, D., Van Dille, M.A. and Johnson, L.A. 1983. Quantification of the X and Y chromosome-bearing spermatozoa of domestic animals by flow cytometry. Biol. Reprod. 28:312-321.
Ginther, O.J. 1971. Some factors which alter estrus cycle in mares. J. Anim. Sci. 33:1158. abstr.
Ginther, O.J. 1983. Sexual behavior following introduction of a stallion into a group of mares. Theriogenology. 19:877.
Ginther, O.J. 1992. In: *Reproductive Biology of the Mare*. ($2^{nd}$ Ed.) Equiservices, Cross Plains, WI.
Gledhill, B.L. 1988. Gender preselection: historical, technical and ethical perspective. Semen Reprod. Endocrinol. 6:385-395.
Gourley, D.D. and Riese, R.L. 1990. Laparoscopic artificial insemination in sheep. Vet. Clin. N. Amer: Food Anim. Prac. 6(3): 615-633.
Grondahl, C., et al, In Vitro Production of Equine Embryos, Biology of Reproduction, Monograph Series I, pp. 299-307 (1995).
Guillou, F. and Combamous, Y. 1983. Purification of equine gonadotropin and comparative study of their acid-dissociation and receptor-binding specificity. Biochem. Biophys. Acta. 755:229-236.
Gumsey, M.P., and Johnson, L.A., Recent improvements in efficiency of flow cytometric sorting of X and Y-chromosome bearing sperm of domestic animals: a review, 1998, New Zealand Society of Animal Protection, three pages.
Harrison, L.A., Squires, E.L. and McKinnon, A.O. 1991. Comparison of hCG, buserelin and luprostiol for induction of ovulation in cycling mares. Eq. Vet. Sci. 3:163-166.
Hofferer, S., Lecompte, F., Magallon, T., Palmer, E. and Combamous, Y. 1993. Induction of ovulation and super ovulation in mares using equine LH and FSH separated by hydrophobic interaction chromatography. J. Reprod. Fert. 98:597-602.

Holton, D.W., Douglas, R.H. and Ginther, O.J. 1977. Estrus, ovulation and conception following synchronization with progesterone, prostaglandin F2 ct and human chorionic gonadotropin in pony mares. J. Anim. Sci. 44:431-437.

Householder, D.D., Pickett, B.W., Voss, J.L. and Olar, T.T. 1981. Effect of extender, number of spermatozoa and hCG on equine fertility. J. Equine Vet. Sci. 1:9-13.

Howard, J.G., Bush, M., Morton, C., Morton, F., Wentzel, K. and Wildt, D.E. 1991. Comparative semen cryopreservation in ferrets (Mustela putorious furo) and pregnancies after laparoscopic intrauterine insemination with frozen-thawed spermatozoa. J. Reprod. Fert. 92:109-118.

Howard, J.G., Roth, T.L., Byers, A.P., Swanson, W.F. and Wildt, D.E. 1997. Sensitivity to exogenous gonadotropins for ovulation and laparoscopic artificial insemination in the thetas and clouded leopard. Biol. Reprod. 56:1059-1068.

Hunter, R.H.F. 1980. Transport and storage of spermatozoa in the female reproductive tract. Proc $4^{th}$ Int. Congr. Artira. Repro. and A.I. 9:227-233.

Hyland, J.H., Ainsworth, C.G.V. and Langsford, D.A. 1988. Gonadotropin-releasing hormone (GnRH) delivered by continuous infusion induces fertile estrus in mares during seasonal acyclicity. Proc. Amer. Assoc. Eq. Prac. 181-190.

Irvine, C.H.G. and Alexander, S.L. 1993. In: Equine Reproduction. Edited by McKinnon and Voss. Lee and Febriger. Philadelphia, London. pp. 37.

Jafar, at al., Sex Selection in Mammals: A Review, Theriogenology, vol. 46, pp. 191-200 (1996).

Jasko, D.J., Martin, J.M. and Squires, E.L. 1992. Effect of volume and concentration of spermatozoa on embryo recovery in mares. Theriogenology. 37:1233-1239.

Johnson L.A., et al., 1987. Flow cytometry of X- and Y-chromosome bearing sperm for DNA using an improved preparation method and staining with Hoechst 333-42. Gamete Research 17: 203-212.

Johnson, A.L. 1986. Pulsatile release of gonadotropin releasing hormone advances ovulation in cycling mares. Biol. Reprod. 35:1123-1130.

Johnson, A.L. and Becker, S.E. 1988. Use of gonadotropin-releasing hormone (GnRH) treatment to induce multiple ovulations in the anoestrous mare. Eq. Vet. Sci. 8:130-134.

Johnson, L.A., Advances in Gender Preselection in Swine, Journal of Reproduction and Fertility Supplement, vol. 52, and pp. 255-266 (1997).

Johnson, L.A., Sex Preselection in Swine: Altered Sex Ratios in Offspring Following Surgical Insemination of Flow Sorted X- and Y-Bearing Sperm, Reproduction in Domestic Animals, vol. 26, pp. 309-314 (1991).

Johnson, L.A. 1988. Flow cytometric determination of spermatozoa sex ratio in semen purportedly enriched for X or Y bearing spermatozoa. Theriogenology. 29:265. abstr.

Johnson, L.A. 1992. Gender preselection in domestic animals using flow cytometrically sorted sperm. J Anim. Sci. Suppl 1.70:8-18.

Johnson, L.A. 1994. Isolation of X- and Y-bearing spermatozoa for sex preselection. In: Oxford Reviews of Reproductive Biology. Ed. HH Charlton. Oxford University Press. 303-326.

Johnson, L.A. 1995. Sex preselection by flow cytometric separation of X and Y chromosome bearing spermatozoa based on DNA difference: a review. Reprod. Fert. Dev. 7:893-903.

Johnson, L.A. and Welch, G.R., Sex Preselection: High-speed flow cytometric sorting of X and Y sperm for maximum efficiency, Theriogenology, vol. 52, (1999), pp. 1323-1341.

Johnson, L.A. and Schulman, J.D. 1994. The safety of sperm selection by flow cytometry. Ham. Reprod. 9(5): 758.

Johnson, L.A., et al, Sex Preselection in Swine: Flow Cytometric Sorting of X- and Y-Chromosome Bearing Sperm to Produce Offspring, Boar Semen Preservation IV, 2000, pp. 107-114.

Johnson, L.A., et al., 1994. Improved flow sorting resolution of X- and Y-chromosome bearing viable sperm separation using dual staining and dead cell gating. Cytometry 17 (suppl 7): 83.

Johnson, L.A., Flook, J.P., Look, M.V. and Pinkel, D. 1987b. Flow sorting of X and Y chromosome bearing spermatozoa into two populations. Gam. Res. 16:203-212.

Johnson, L.A., Welch, G.R., Rens, W. and Dobrinsky, J.R. 1998. Enhanced flow cytometric sorting of manunalian X and Y sperm: high speed sorting and orienting No. 77.1e for artificial insemination. Theriogenology. 49(1): 361. abstr.

K.L. Macmillan, et al., Prostaglandin F2a—A Fertility Drug In Daily Cattle? Ruakura Animal Research Station, Private Bag, Hamilton, New Zealand, Theriogenology, Sep. 1982, vol. 18 No. 3, pp. 245-253.

Kachel, V., et al., Uniform Lateral Orientation, Caused by Flow Forces, of Flat Particles in Flow-Through Systems, The Journal of Histochemistry and Cytochemistry, 1997, vol. 25, No. 7, pp. 774-780.

Kanayama, K., Sankai, T., Nariaik, K., Endo, T. and Sakuma, Y. 1992b. Pregnancy by means of tubule insemination and subsequent spontaneous pregnancy in rabbits. J. Int. Med. Res. 20:401-405.

Kilicarslan, M.R., Horoz, H., Senunver, S.C., Konuk, S.C., Tek, C. and Carioglu, B. 1996. Effect of GrnRH and hCG on ovulation and pregnancy in mares. Vet. Rec. 139:119-120.

Lapin, D.R. and Ginther, O.J. 1977. Induction of ovulation and multiple ovulations in seasonally ovulatory and ovulatory mares with an equine pituitary extract. J. Anim. Sci. 44:834-842.

Lawrenz, R. 1985. Preliminary results of non-surgical intrauterine insemination of sheep with thawed frozen semen. J S Afr. Vet. Assoc. 56(2): 61-63.

Levinson, G., Keyvanfar, K., Wu, J.C., Fugger, E.F., Fields, R.A., Harton, G.L., Palmer, F.T., Sisson, M.E., Starr, K.M., Dennison-Lagos, L., Calvo, L., Sherins, R.J., Bick, D., Schulman, J.D. and Black, S.H. 1995. DNA-based X-enriched sperm separation as an adjunct to preimplantation genetic testing for the preparation of X-linked disease. Mol. Human Reprod. 10:979-982.

Lindsey, A., et al., Hysteroscopic Insemination of Mares with Non-frozen Low-dose Unsexed or Sex-sorted Spermatozoa, currently unpublished, pp. 1-15.

Linge, F. 1972. Faltforsok med djupfrost sperma (field trials with frozen sperm). Farskotsel. 52:12-13.

Long, C.R., Rath, D., Welch, G.R., Schreier, L.L., Dobrinsky, J.R. and Johnson, L.A. 1998. In vitro production of porcine embryos from semen sorted for sex with a high-speed cell sorter: comparison of two fertilization media. Theriogenology. 49(1): 363. abstr.

Loy, R.G. and Hughes, J.P. 1965. The effects of human chorionic gonadotropin on ovulation, length of estrus, and fertility in the mare. Cornell Vet. 56:41-50.

Matsuda, Y. and Tobari, I. 1988. Chromosomal analysis in mouse eggs fertilized in vitro with sperm exposed to ultraviolet light (UV) and methyl and ethyl methane sulfonate (MMS and EMS). Mutat. Res. 198:131-144.

Maxwell, W.M.C., Evans, G., Rhodes, S.L., Hillard, M.A. and Bindon, B.M. 1993. Fertility of Super ovulated Ewes after Intrauterine or Oviductal Insemination with Low Numbers of Fresh or Frozen-Thawed Spermatozoa. Reprod. Fertil. Dev. 5:57-63.

McCue, P.M. 1996. Super ovulation. Vet. Clin. N. Amer. Eq. Prac. 12:1-11.

McCue, P.M., Fleury, J.J., Denniston, D.J., Graham, J.K. and Squires, E.L. 1997. Oviductal insemination in the mare. $7^{th}$ Int Symp. Eq. Reprod. 133. abstr.

McDonald, L.E. 1988. Hormones of the pituitary gland. In: Veterinary Pharmacology and Therapeutics. $6^{th}$ ed. Edited by N. H. Booth and L.E. McDonald. Ames, Iowa State Univ. Press. pp. 590.

McKenna, T., Lenz, R.W., Fenton, S.E. and Aχ, R.L. 1990. Nonreturn rates of dairy cattle following uterine body or communal insemination. J. Dairy Sci. 73:1179-1783.

McKinnon, A. and Voss, J., Equine Reproduction, Lea & Febriger, Philadelphia, 1993, pp. 291, 299-302, 345-348, 739-797.

McKinnon, A. et al, 1993. Predictable ovulation in mares treated with an implant of the GnRH analogue deslorelin. Eq. Vet. J. 25:321-323.

McKinnon, A.O. et al, 1996. Repeated use of a GnRH analogue deslorelin (Ovuplant) for hastening ovulation in the transitional mare. Eq. Vet. J. 29:153-155.

McNutt, et al., Flow Cytometric Sorting of Sperm: Influence on Fertilization and Embryo/Fetal Development in the Rabbits, Molecular Reproduction and Development, vol. 43, pp. 261-267 (1996).

Meyers, P.J., Bowman, T., Blodgett, G., Conboy, H.S., Gimenez, T., Reid, M.P., Taylor, B.C., Thayer, J., Jochle, W. and Trigg, T.E. 1997. Use of the GnRH analogue, deslorelin acetate, in a slow release implant to accelerate ovulation in oestrous mares. Vet. Rec. 140:249-252.

Michaels, Charles, Beef A.I. Facilities that work, Proc. Fifth N.A. A.B Tech. Conf. A.I. Reprod. Columbia, MO. pp. 20-22.

Michel, T.H., Rossdale, P.D. and Cash, R.S.G. 1986. Efficacy of human chorionic gonadotrophin and gonadatrophin releasing hormone for hastening ovulation in Thoroughbred mares. Eq. Vet. J. 6:438-442.

Miller, S.J. 1986. *Artificial Breeding Techniques in Sheep*. In Morrow, D.A. (ed): Current Therapy in Theriogenology 2. Philadelphia, WB Saunders.

Mirskaja, L.M. and Petrapavlovskii, V.V. 1937. The reproduction of normal duration of heat in the mare by the administration of Prolan. Probl. Zivotn. Anim. Breed. Abstr. 5:387.

Molinia, F.C., Gibson, R.J., Brown, A.M., Glazier, A.M. And Rodger, J.C. 1998. Successful fertilization after super ovulation and laparoscopic intrauterine insemination of the brush tail possum, *Trichosurus vulpecula*, and tammar wallaby, *Macropus eugenii*. J. Reprod. Fert. 112:9-17.

Morcom, C.B. and Dukelow, W.R. 1980. A research technique for the oviductal insemination of pigs using laparoscopy. Lab. Anim. Sci. 1030-1031.

Morris, L.H., et al., Hysteroscopic insemination of small numbers of spermatozoa at the uterotubal junction of preovulatory mares, Journal of Reproduction and Fertility, vol. 118, pp. 95-100 (2000).

Muller, W. and Gautier, F. 1975. Interactions of heteroaromatic compounds with nucleic acids. Euro. J. Biochem. 54:358.

Munne, S. 1994. Flow cytometry separation of X and Y spermatozoa could be detrimental to human embryos. Hum. Reprod. 9(5): 758.

Pace, M.M. and Sullivan, J.J. 1975. Effect of timing of insemination, numbers of spermatozoa and extender components on pregnancy rates in mares inseminated with frozen stallion semen. J Reprod. Fert. Suppl. 23:115-121.

Parrish, J.J., et al, Capacitation of Bovine Sperm by Heparin, Department of Meat and Animal Science, University of Wisconsin, Madison, WI 53706, Biology Of Reporoduction 38, 1171-1180 (1988).

Peippo, J., et al., Sex diagnosis of equine preimplantation embryos using the polymerase chain reaction, Theriogenology, vol. 44 619-627 (1995).

Perry, E.J. 1968. Historical Background In: *The Artificial Insemination of Farm Animals*. 4th ed. Edited by E.J. Perry. New Brunswick, Rutgers University Press, pp. 3-12.

Petersen, G.A., et al, Cow and Calf Performance and Economic Considerations of Early Weaning of Fall-Born Beef Calves, J. Anim. Sci., 1987, 64, pp. 15-22.

Pickett GW, et al., Management of the mare for maximum reproductive efficiency, Bulletin No. 6 Colorado State University, Ft. Collins CO. (1989).

Pickett, B.W, et al., 1976. Factors influencing the fertility of stallion spermatozoa in an A.I. program. Proc. 8th Internat. Congr. Anim. Reprod. A.I. Krakow, Poland. 4: 1049-1052.

Pickett, B.W. and Back, D.G. 1973. Procedures for preparation, collection, evaluation and insemination of stallion semen. C.S.U. Exp. Sta. Artira. Reprod. Lab. Gen. Series Bull. 935.

Pickett, B.W., Burwash, L.D., Voss, J.L. and Back, D.G. 1975b. Effect of seminal extenders on equine fertility. J. Anim. Sci. 40:1136-1143.

Pinkel, D., Gledhill, B.L., Van Dilla, M.A., Stephenson, D. and Watchmaker, G. 1 982b. High-resolution DNA measurements of mammalian spermatozoa. Cytometry. 3:1-9. (1982b).

Rath, D., et al., Low Dose Insemination Technique in the Pig, Boar Semen Preservation IV, 2000, pp. 115-118.

Reiling, B.A., et al., Effect of Prenatal Androgenization on Performance, Location, and Carcass and Sensory Traits on Heifers in Single Calf Heifer System, J. Anim. Sci., 1995, 73: 986, pp. 986-992.

Rens, W., et al., A Novel Nozzle for More Efficient Sperm Orientation to Improve Sorting Efficiency of X and Y Chromosome-Bearing Sperm, Technical Notes, Cytometry 33, 1998, pp. 476-481.

Rens, W., et al., Improved Flow Cytometric Sorting of X- and Y-Chromosome Bearing Sperm: Substantial Increase in Yield of Sexed Semen, Molecular Reproduction and Development, 1999, pp. 50-56.

Ritar, A. and Ball, A. 1991. Fertility of young cashmere goats after laparoscopic insemination. J. Agr. Sci. 117:271-273.

Roberts, J.R. 1971. In: *Veterinary Obstetrics and Genital Diseases*. Ithaca, New York. pp. 740-749.

Roser, JF., Evans, J.W., Kiefer, DP., Neeley, D.P. and Pacheco, C.A. 1980. Reproductive efficiency in mares with anti-hCG antibodies. Proc 9th Int. Congr. Artira. Repro. and A.I. 4:627. abstr.

Roth, T.L., Wolfe, B.A., Long, J.A., Howard, J. and Wildt, D.E. 1997. Effects of equine chorionic gonadotropin, human chorionic gonadotropin, and laparoscopic artificial insemination on embryo, endocrine, and luteal characteristics in the domestic cat. Bio Reprod. 57:165-171.

Rowley, H.S, Squires, E.L. and Pickett, B.W. 1990. Effect of insemination volume on embryo recovery in mares., J. Equine Vet. Sci. 10:298-300.

Salmon, S. 1976. Artificial insemination of Sheep. Chippendale, New South Whales. Publicity Press. p. 83-84.

Salisbury, G.W. and VanDemark, N.L. 1961. *Physiology of Reproduction and Artificial Insemination of Cattle*. San Francisco: Freeman and Company.

SAS, SAS/STAT User's Guide (Release 6.03), SAS Inst. Inc., Cary, NC. 1988. 3 pages.

Schenk, J.L., Cryopreservation of flow-sorted bovine spermatozoa, Theriogenology, vol. 52, 1375-1391(1999).

Schenk, J.L. and Seidel, Jr., G.E., Imminent Commercialization of Sexed Bovine, Proceedings, The Range Beef Cow Symposium XVL, 1999, pp. 89-96.

Schmid R.L., et al, Fertilization with Sexed Equine Spermatozoa Using Intracytoplasmic Sperm Injection and Oviductal Insemination, 7th International Symposium on Equine Reproduction, pp. 139 (Abstract) (1998).

Seidel, G.E. et al., Insemination Of Heifers With Very Low Numbers Of Frozen Spermatozoa. Colorado State University, Fort Collins, Atlantic Breeders Cooperative, Lancaster, PA, DUO Dairy, Loveland, CO, Jul. 1996.

Seidel, G.E. et al., Artificial Insemination With X-and Y-Bearing Bovine Sperm, Animal Reproduction and Biotechnology Laboratory, Colorado State University, Fort Collins, CO; Germplasm and Gamete Physiology Lab, ARS, USDA, Beltsville, MD; Atlantic Breeders Coop, Lancaster, PA; DUO Diary, Loveland, CO, USA Jan. 1996.

Seidel, G.E. et al., Uterine Horn Insemination of Heifers With Very Low Numbers of Non-frozen and Sexed Spermatozoa, Animal Reproduction and Biotechnology Laboratory Colorado State University, Atlantic Breeders Cooperative, Lancaster, PA 17601, Germplasm and Gamete Physiology Laboratory ARS, USDA, Beltsville, MD 20705, DUO Diary, Loveland, CO 80538, Theriogenology 48: 1255-1264, 1997.

Seidel, G.E. Jr, et al., Artificial Insemination of Heifers with Cooled, Unfrozen Sexed Semen, Theriogenology, vol. 49 pp. 365 (Abstract) (1998).

Seidel, G.E. Jr, et al., Insemination of Heifers with Sexed Sperm, Theriogenology, vol. 52, pp. 1407-1421 (1999).

Seidel, G.E. Jr., Cran, D.G., Herrickoff, L.A., Schenk, J.L., Doyle, S.P. and Green, R.D. 1999. Insemination of heifers with sexed frozen or sexed liquid semen. Theriogenology. 51. (in press). abstr. (1999).

Senger, P.L., Becker, W.C., Davidge, S.T., Hillers, J.K. and Reeves, J.J. 1988. Influence of communal insemination on conception rates in dairy cattle. J Anim. Sci, 66:3010-3016.

Shelton, J.N. and Moore, N. W. 1967. The response of the ewe to pregnant mare gonadotropin and to horse anterior pituitary extract. J. Reprod. Fen. 14:175-177.

Shilova, A.V., Platov, E.M. and Lebedev, S.G. 1976. The use of human chorionic gonadothrophin for ovulation date regulation in mares. 8th Int. Congr. On Anim. Repro. and A.I. 204-208.

Squires, E.L, Moran, D.M., Farlin, ME., Jasko, D.J., Keefe, T.J., Meyers, S.A., Figueiredo, E., McCue, P.M. and Jochle, W. 1994. Effect of dose of GnRH analogue on ovulation in mares. Theriogenology. 41:757-769.

Squires, E.L., Early Embryonic Loss in Equine Diagnostic Ultrasonography, 1st Ed. pp. 157-163 Eds. Rantanen & McKinnon. Williams and Wilkins, Baltimore, Maryland (1998).

Squires, E.L., et al, Cooled and frozen stallion semen, Bulletin No. 9, Colorado State University, Ft. Collins, CO. (1999).

Sullivan, J.J., Parker, W.G. and Larson, LL. 1973. Duration of estrus and ovulation time in non-lactating mares given human chorionic gonadotropin during three successive estrous periods. J.A.V.M.A. 162:895-898.

Taljaard, T.L., Terblanche, S.J., Bertschinger, H.J. and Van Vuuren, L.J. 1991. The effect of the laparoscopic insemination technique on the oestrus cycle of the ewe. J. S Afr. Vet. Assoc. 62(2): 60-61.

U.S. Appl. No. 09/454,488, entitled Improved Flow Cytometer Nozzle and Flow Cytometer Sample Handling Methods, filed Dec. 3, 1999.

U.S. Appl. No. 60/224,050, entitled Integrated System for Herd Management With Terminal-Cross Program Using Sexed Semen, filed Aug. 9, 2000.

U.S. Appl. No. 60/238,294, entitled Hysteroscopic Insemination of Mares, filed Oct. 5, 2000.

U.S. Appl. No. 09/001,394, entitled Improved Sheath Fluids and Collection Systems for Sex Specific Cytometer Sorting of Sperm, filed on Dec. 31, 1997, 83 pages and 4 drawings.

U.S. Appl. No. 60/211,093, entitled Integrated System for Herd Management Using Sexed Semen, filed Jun. 12, 2000.

Vasquez, J., et al., A.I. in Swine; New Strategy for Deep Insemination with Low Numbers of Spermatozoa Using a Non-surgical Methodology, 14th International Congress on Animal Reproduction, vol. 2, Stockholm, Jul. 2000, p. 289.

Vasquez, J., et al., Development of a Non-surgical Deep Intra Uterine Insemination Technique, IV International Conference on Boar Semen Preservation, Maryland, Aug. 1999, p. 35 and photo of display board.

Vasquez, J., et al., Successful Low-Dose Insemination by a Fiber optic Endoscope Technique in the Sow, Proceedings Annual Conference of the International Embryo Transfer Society, Netherlands, Theriogenology, vol. 53, Jan. 2000, pp. 201.

Vasquez, J., et al., Hypsometric Swelling Test as Predictor of the Membrane Integrity in Boar Spermatozoa, Boar Semen Preservation IV, 4th International Conference on Boar Semen Preservation, Maryland, pp. 263.

Vidament, M., Dupere, A.M., Julienne, P., Evain, A., Noue, P. and Palmer, E. 1997. Equine frozen semen freeze ability and fertility field results. Theriogenology. 48:907.

Voss, J.L. and Pickett, B.W. 1976. Reproductive management of the broodmare. C.S.U. Exp. Sta. Anim. Reprod. Lab. Gen. Series. Bull. 1-12.

Voss, J.L., Pickett, B.W., Burwash, L.D. and Daniels, W.H. 1974. Effect of human chorionic gonadotropin on duration of estrous cycle and fertility of normally cycling, non-lactating mares. J.A.V.M.A. 165:704-706.

Voss, J.L., Squires, E.L., Pickett, B.W., Shideler, R.K. and Eikenberry, D.J. 1982. Effect of number and frequency of inseminations on fertility in mares. J. Reprod. Fertil. Suppl. 32:53-57.

Welch G.R., et al., 1994. Fluidic and optical modifications to a FACS IV for flow sorting of X- and Y- chromosome bearing sperm based on DNA. Cytometry 17 (suppl. 7): 74.

Wilson, C.G., Downie, C.R., Hughes, J.P. and Roser, J.F. 1990. Effects of repeated hCG injections on reproductive efficiency in mares. Eq. Vet. Sci. 4:301-308.

Wilson, M.S. 1993. Non-surgical intrauterine artificial insemination in bitches using frozen semen. J.Reprod. Fert Suppl. 47:307-311.

Woods, J. and Ginther, O.J,. 1983. Recent studies related to the collection of multiple embryos in mares. Theriogenology. 19:101-108.

Woods, J., Bergfelt, D.R. and Ginther, O.J. 1990. Effects of time of insemination relative to ovulation on pregnancy rate and embryonic-loss rate in mares. Eq. Vet. J. 22(6) 410-415.

Office Action, U.S. Appl. No. 09/001,394, dated Feb. 19, 1999 (Lodo).

Notice of Allowability with Examiner's Amendment, U.S. Appl. No. 09/001,394, dated Oct. 27, 1999 (Lodo).

Office Action, U.S. Appl. No. 09/551,959, dated Jan. 23, 2002 (Lodo Div1).

Notice of Allowability with Examiner's Amendment, U.S. Appl. No. 09/551,959, dated Oct. 15, 2002 (Lodo Div1).

Office Action, U.S. Appl. No. 10/378,109, dated Jun. 10, 2005 (Lodo Div2).

Office Action, U.S. Appl. No. 10/378,109, dated Nov. 21, 2005 (Lodo Div2).

Office Action, U.S. Appl. No. 09/582,809, dated Sep. 17, 2001 (Lodo USNP).

Notice of Allowability with Examiner's Amendment, U.S. Appl. No. 09/582,809, dated Apr. 17, 2002 along with Notice of Withdrawal from Issue dated Oct. 31, 2002 (Lodo USNP).

Office Action, U.S. Appl. No. 09/582,809, dated Oct. 6, 2002 (Lodo USNP).

Office Action, U.S. Appl. No. 09/582,809, dated Oct. 3, 2003 (Lodo USNP).

Office Action, U.S. Appl. No. 09/582,809, dated Jul. 20, 2004 (Lodo USNP).

Office Action, U.S. Appl. No. 09/582,809, dated Apr. 20, 2005 (Lodo USNP).

Office Action, U.S. Appl. No. 09/015,454, dated Sep. 14, 1998 (SuperO).

Office Action, U.S. Appl. No. 09/015,454, dated Apr. 24, 1999 (SuperO).

Notice of Allowability with Examiner's Amendment, U.S. Appl. No. 09/015,454, dated Dec. 27, 1999 (SuperO).

Office Action, U.S. Appl. No. 09/448,643, dated Jun. 1, 2000 (SuperO Cont1).

Office Action, U.S. Appl. No. 09/448,643, dated Mar. 21, 2001 (SuperO Cont1).

Notice of Allowability with Examiner's Amendment, U.S. Appl. No. 09/448,643, dated Oct. 9, 2001 (SuperO Cont1).

Abdel-Ghaffar, A. E., et al., "Rabbit Semen Metabolism" in Rabbit Production in Hot Climates Baselga and Marai (eds); International Conference of Rabbit Production in Hot Climates 1994, p. 305-312.

Akhtar, S., et al., "Prevalence of Five Stereotypes of Bluetongue Virus in a Rambouillet Sheep Flock in Pakistan", Veterinary Record 138, p. 495. (1995).

Aldrich, S. L., et al., "Parturition and Periparturient Reproductive and Metabolic Hormone Concentration in Prenatally Androgenized Beef Heifers", J. Anim. Sci. 73:3712. (1995).

Amann, R. P. et al., "Issues Affecting Commercialization of Sexed Sperm" Therio. 52:1441. (1999).

Amann, R.P. "Fertilizing Potential Vitro of Semen from Young Beef Bulls Containing a High or Low Percentage of Sperm with a Proximal Dropler" Theriogenology 54: 1499-1515, 2000.

Amann, Rupert P. "Cryopreservation of Sperm" 1999, Encyclopedia of Reproduction 1:733-783.

American Meat and Science Association in Cooperation with National Livestock and Meat Board, "Research Guidelines for Cookery and Sensory Evaluation and Instrumental Tenderness Measurements for Fresh Meat". (1995).

Arriola, J. and Foote, R.H.: "Glycerolation and Thawing Effects on Bull Spermatozoa frozen in Detergent-Treated Egg Yok and Whole Egg Extenders," J Dairy Sci, 70:1664-1670 (1987), Abstract only.

Asbury, Charles A. "Fluorescen Spectra of DNA Dyes Measured in a Flow Cytometer," University of Washington Feb. 19, 1996.

Bagley, C. P. "Nutritional Management of Replacement Beef Heifers: a Review" J. Anim. Science 71:3155-3163. (1993).

Bailey, C. M. et al., "Nulliparous Versus Primiparous Crossbred Females for Beef", J. Anim. Sci. 69:1403. (1991).

Bakker Schut, Tom C. "A New Principle of Cell Sorting by Using Selective Electroportation in a Modified Flow Cytometry," University of Twente, Mar. 10, 1990.

Barnes, F. L. and Eyestone, W. H., "Early Cleavage and the Maternal Zygotic Transition in Bovine Embryos", Therio. vol. 33, No. 1, pp. 141-149. (1990).

Batellier, F. et al., "Advances in Cooled Semen Technology" Animal Reproduction Science 68 p. 181-190 (2001).

Becker, S.E. and Johnson, A. L. "Effects of Gonadotropin-Releasing Hormone Infused in a Pulsatile or Continuous Fashion on Serum Gonadotropin Concentrations and Ovulation in the Mare", J. Anim. Sci. 70:1208-1215. (1992).

Behrman, S. J., et al., "Freeze Preservation of Human Sperm" American Journal of Obstetrics and Gynecology vol. 103 (5) p. 654-664 Mar. 1, 1969.

Bellows, R. A., et al., "Cause and Effect Relationships Associated With Calving Difficulty and Calf Birth Weight", J. Anim. Sci. 33:407. (1971).

Berardinelli, J. G., et al., "Source of Progesterolle Prior to Puberty in Beef Heifers". J. Anim. Sci. 49:1276. (1979).

Bergfeld, E. G., et al., "Ovarian Follicular Development in Prepubertal Heifers is Influenced by Level of Dietary Energy Intake", Bio. of Repro. 51:1051. (1994).

Berry, B. W., et al., "Beef Carcass Maturity Indicators and Palatability Attributes", J. Anim. Sci. 38:507 (1974).

Beyhan, Z., Et Al., 1999 Sexual Dimorphism In IVM-IVF Bovine Embryos Produced from X and Y Chromosome-Bearing Spermatozoa Sorted by High Speed Flow Cytometry. Theriogenology. 52: 35-48.

BigosBigos, Martin "Nine Color Eleven Parameter Immunophenotyping Using Three Laser Flow Cytometry," Stanford University Dec. 22, 1998.

Bioxcell, Bovine Sperm Preservation, Advertisement Jun. 28, 2005.

Bond, J., et al., "Growth and Carcass Traits of Open Beef Heifers Versus Beef Heifers That Have Calved", Nutrition Reports International 34:621. 1986.

Boucque, C. V., et al., "Beef-Production With Maiden and Once-Calved Heifers", Livestock Prod. Sci. 7:121. 1980.

Bourdon, R. M. and J. S. Brinks. "Simulated Efficiency of Range Beef—Production III. Culling Strategies and Nontraditional Management-Systems", J. Anim. Sci. 65:963. 1987.

Braun, J. et al, "Effect of Different Protein Supplements on Motility and Plasma Membrane Integrity of Frozen-Thawed Stallion Spermatozoa", Cryobiology (1995) 32:487-492.

Brinsko, S.P. et al., "Artificial Insemination and Preservation of Semen." Veterinary Clinics of North America:Equine Practice vol. 8 No. 1 Apr. 1992 pp. 205-218.

Brookes, A. J. and O'Byme, M., "Use of Cow-Heifers in Beef Production" J. of the Royal Agricultural Society of England 126:30. 1965.

Buchanan, B.R. "Pregnancy Rates in Mares Following a Single Insemination with a Low Number of Spermatozoa into the Tip of the Uterine Horn" Theriogenology p. 395.

Bums, P. D. and Spitzer, J.C., "Influence of Biostimulation on Reproduction in Postpartum Beef-Cows", J. Anim. Sci. 70:358. 1992.

Byerley, D. J., et al., "Pregnancy Rates of Beef Heifers Bred Either on Puberal or Third Estrus". J Anim. Sci. 65:645. 1987.

Catt, et al., "Assessment of Ram and Boar Spermatozoa During Cell-Sorting by Flow Cytometry", Reproduction Dom Animal, vol. 32, pp. 251-258. 1997.

Catt, S. L., et al., "Birth of a Male Lamb Derived from an In Vitro Matured Oocyte Fertilized by Intracytoplasmic Injection of a Single Presumptive Male Sperm", Veterinary Record 139, p. 494-495. 1996.

Cave-Penney, Tony, "Sexed Semen Offers Faster Genetic Gain", Farming News, Livestock Supplement, Feb. 1997, p. 28.

Celestron: *Telescope Basics*: www.celestron.com/tb-2ref/htm; 4 pages.

Chandler, J. E., "Videomicroscopic Comparison of Bull Sperm and Leukocyte Chromosome Areas as Related to Gender", J Dairy Sci 73, p. 2129-2135. 1990.

Chandler, J. E., et al, "Bovine Spermatozoal Head Size Variation and Evaluation of a Separation Technique Based on this Size", Therio. 52, p. 1021-1034. 1999.

Chen, S.H. "Effects of Oocyte Activation and Treatment of Spermatozoa on Embryonic Development Following Intracytoplasmic Sperm Injection in Cattle" Theriogenology 48: 1265-1273, 1997.

Chen, Y. et al., Survival of Bull Spermatozoa Seeded and Frozen at Different Rates in Egg Yolk-Tris and Whole Milk Extenders, 1993 J Dairy Sci 76:1028-1034.

Choi, Y.H. "Developmental Cappacity of Equine Oocytes Matured and Cultured in Equine Trophoblast-Conditioned Media" Theriogenoogy 56: 320-339, 2001.

Cran, D. G., et al., "Sex Preselected in Cattle: A Field Trial", Veterinary Record 136, 1995, p. 495-496.

Cran, D. G., et al., "The Predetermination of Embryonic Sex Using Flow Cytometrically Separated X and Y Spermatozoa" Human Reproduction Update 1996, vol. 2 (4) p. 355-63.

Crowley, J. P. "The facts of Once-Bred Heifer Production" School of Agric., Univ. of Aberdeen, Scotland. 1973.

Cui, K. et al, "X Larger than Y", Nature 366, p. 177-118, 1993.

Cui, K., "Size Differences Between Human X and Y Spermatozoa and Prefertilization Diagnosis", Molecular Human Reproduction, vol. 3, No. 1, pp. 61-67. 1997.

da Silva, Coutinho M.A.."Effect of time of oocyte collection and site of insemination on oocyte transfer in mares." Animal Reproduction and Biotechnology Laboratiory, Colorado State Uniuversity, Fort Collins Journal of Animal Science 2002. 80:1275-1279.

DakoCytomation, "*MoFlo® Sorters*" http://www.dakocytomation.us/prod_productrelatedinformation?url=gprod_moflo_index.htm_one_page, printed Jun. 26, 2003.

Database up 1 BR9704313 (Alves, De Resende et al) Jun. 4, 1999, abstract only.

de Leeuw, F.E. et al:"Effects of carious cryoprotective agents and membrane-stabilizing compounds on bull sperm emebrane integrity after cooling and freezing" Cryobiology US, Academic Press Inc 1993 pp. 32-44.

Denham, A. "In-vitro studies on Sandhill Range Forage as Related to Cattle Preference", M.S. Thesis. Colorado State University. 1965.

Denk, Winfried. "Two-Photon Molecular Excitation in Laser-Scanning Microscopy," Handbook of Biological Confocal Microscopy. 1995.

Deutscher, G. H. "Extending Interval From Seventeen to Nineteen Days in the Melengestrol Acetate-Prostaglandin Estrous Synchronization Program for Heifers". The Professional Animal Scientist 16:164. 2000.

Diagnostic Products Corporation. "*Coat-A-Count*" http://www.Progesterone.com. 1998.

Dikeman, M. E. "Cattle Production Systems to Meet Future Consumer Demands" J. Anim. Sci. 59:1631, 1984.

Dinnyes, A., et al., "Timing of the First Cleavage Post-Insemination Affects Cryosurvival of in Vitro-produced Bovine Blastocysts", Molec. Reprod. Develop. 53, p. 318-324. 1999.

Dipped, K.D. "Fertilization Rates in Superovulated and Spontaneously Ovulating Mares" Theriogenology 41: 1411-1423, 1994.

Donaldson, L. E., "Effect of Insemination Regimen on Embryo Production in Superovulated Cows", The Veterinary Record, Jul. 13, p. 35-37, 1985.

Doyle, S. P., et al. "Artificial Insemination of Lactating Angus Cows with Sexed Semen". Proc. Western Sect. Am. Soc. Anim. Sci. 50:203. 1999.

Dresser D.W. et at. Analysis of DNAcontent ofLiving Spermatozoa Using Flow Cytometry Technique Journal of Reproduction and Fertility, 1993, vol. 98, pp. 357-365.

Ferrell, C. L. Effects of Post-Weaning Rate of Gain on Onset of Puberty and Productive Performance of Heifers of Different Breeds. J. Anim. Sci. 55:1272. 1982.

Ferrell, C. L. and T. G. Jenkins. "Energy-Utilization by Mature, Nonpregnant, Nonlactating Cows of Different Types" J. Anim. Sci. 58:234. 1984.

Field, R. A., et al., "Bone-Ossification and Carcass Characteristics of Wethers Given Silastic Implants Containing Estradiol", J. Anim. Sci. 68:3663-3668. 1990.

Field, R. et al., "Growth, Carcass, and Tenderness Characteristics of Virgin, Spayed, and Single-Calf Heifers", J. Anim. Sci. 74:2178. 1996.

Foote, et al. Motility and Fertility of Bull Sperm Frozen-Thawed Differently in Egg Yolk and Milk Extenders Containing Detergent, 1987 J Dairy Sci 70:2642-2647.

Foote, R.H., "Buffers and Extenders: What Do They Do? Why Are They Important?" Proc. of the NAAB Tech. Conf. On Artificial Insemination and Reproduction, 62-70 (1984).

Francon, M. and Yamamoto, T., "Un Noveau et tres simple dispositif interferentiel applicable as microscope" Optica Acta 9, p. 395-408. 1962.

Fuller, Robert R. "Characterizing Submicron Vesicles With Wavelenth-Resolved Fluorescence in Flow Cytometry," University of Illinois, May 13, 1996.

Gombe, S. and Hansel, W. "Plasma Luteinizing☐Hormone (LH) and Progesterone Levels in Heifers on Restricted Energy Intakes." J. Anim. Sci. 37:728. 1973.

Goppert-Mayer,"Uber Elementarakte mit zwei Quantensprungen Von Maria Copper-Mayer".

Gottlinger et al., "Operation of a Flow Cytometer", Flow Cytometry and Cell Sorting, A. Radbruch (Ed.), 1992, pp. 7-23.

Graham, J. Analysis of Stallion semen and its Relation to Fertility. Abstract.

Graham, J.K. and Hammerstedt, R.H.: "Differential Effects of Butylated Hydroxytoluene Analogs on Bull Sperm Subjected to Cold-Induced Membrane Stress," Cryobiology, 29:106-117 (1992).

Graham, James K., "Effect of Cholesterol-Loaded Cyclodextrins in Semen Extenders", Proceedings of the 19th Technical Conference on Artificial Insemination & Reproduction, 2003, pp. 91-95.

Graven, H. O., "Genetic Aspects of Early Calving." In: J.C. Taylor (Ed.) *The Early Calving of Heifers and Its Impact on Beef Production*. 59 (1975).

Gregory, K. E., et al., "Characterization of Biological Types of Cattle—Cycle III: II Growth Rate and Puberty in Females" J. Anim. Sci. 49:461 (1979).

Grimes, I. F, and T. B. Turner. "Early Weaning of Fall Born Calves II. Post Weaning Performance of Early and Normal☐Weaned Calves". I. Prod. Agric. 4:168 (1991).

Hall, J. B., et al., "Effect of Age and Pattern of Gain on Induction of Puberty with a Progestin in Beef Heifers." J. Anim. Sci. 75:1606 (1997).

Hamamatsu, *Technical Information. Optical Detector Selection: A Delicate Balancing Act*, web page, http://www.optics.org/hamamatsu/photodiode.html, printed on Apr. 15, 2000, 6 pages total.

Hamano, K., et al., "Gender Preselection in Cattle with Intracytoplasmically Injected, Flow Cytometrically Sorted Sperm Heads", Biology of Reproduction 60, p. 1194-1197 (1999).

Hammerstedt, et al., "Cryopreservation of Mammalian Sperm: What We Ask Them to Survive," Journal of Andrology, 11:1:73-88 (1990) Abstract only.

Harte, F. J. "System of Production of Beef From Once Calved Heifers." In: J.C. Taylor (Ed.) *The Early Calving of Heifers and its Impact on Beef Production*. 123 (1975).

Hawk, H. W., et al., "Fertilization Rates in Superovulating Cows After Deposition of Semen on the Infundibulum Near the Uterotubal Junction or After Insemination with High Numbers of Sperm", XP-002103478, Therio. vol. 29, No. 5, p. 1131-1142 (1988).

Hermesmeyer, G. N., et al. "Effects of Prenatal Androgenization and Implantation on the Performance and Carcass Composition of Lactating Heifers in the Single-Calf Heifer System." The Professional Animal Scientist 15:173. 1999.

Herweijer, Hans. "High-Speed Photodamage Cell Selection Uing Bromodeoxyuridine/Hoechst 33342 Photosensitized Cell Killing," Sep. 23, 1987.

Herzenberg, Leonard A. "Flourescence-activated Cell Sorting," pp. 108-117.

Hilton, G. G., et al., "An Evaluation of Current and Alternative Systems for Quality Grading Carcasses of Mature Slaughter Cows." J. Anim. Sci. 76:2094. 1998.

Ho, L., et al., "Influence of Gender, Breed and Age on Maturity Characteristics of Sheep." J. Anim. Sci. 67:2460-2470. 1989.

Hohenboken, W. D. "Applications of sexed semen in cattle production." Therio. 52:1421. 1999.

Horan, Paul K. "Quantitative Single Cell Ana,lysis and Sorting, Rapid Analysis and sorting of cells is emerging as an important new technology in research and medicine."

IMV Technologies, Protocol of Bioxcell with Fresh Semen, 1 page, 2000.

IMV Technologies, Protocol of Bioxcell with Frozen Semen, 2 pages, 2000.

lwazumi, Y., et al., "Superovulation Using CIDR in Holstein Cows" J. of Reprod. Dev. vol. 40 (3) 1994, pp. 259-266.

Jakubiczka, S. et al. "A Bovine Homologue of the Human TSPY Gene." Genomics. 1993, vol. 17, No. 3, pp. 732-735.

Jarriage, R. "Age of Cows at First Calving in France." In: J.C. Taylor (Ed.) *The Early Calvino of Heifers and its Impact on Beef Production*. 10. (1975).

Jasko, D. J., et al., "Pregnancy Rates Utilizing Fresh, Cooled and Frozen-Thawed Stallion Semen", American Association of Equine Practitioners 38th Annual Convention Proceedings, 1992, p. 649-60.

Johnson, L.A., "Gender Preselection in Humans? Flow Cytometric Separation of X and Y Spermatozoa for the Prevention of X-Linked Diseases" Human Reproduction vol. 8 No. 10, p. 1733-1739 (1993).

Johnson, L.A., "Gender Preselection in Mammals: An Overview", Deutsch. Tierarztl. Wschr, vol. 103, p. 288-291 (1996).

Johnson, L.A., "Sex Preselection in Rabbits: Live Births from X and Y Sperm Separated by DNA and Cell Sorting", Biology of Reproduction 41, pp. 199-203 (1989).

Johnson, L.A., "Successful Gender Preselection in Farm Animals", Agricultural Biotechnology, p. 439-452. (1998).

Johnson, L.A., et al., "Modification of a Laser-Based Flow Cytometer for High-Resolution DNA Analysis of Mammalian Spermatozoa" Cytometry 7, pp. 268-273 (1986).

Joseph, R. L. "Carcass composition and meat quality in once calved heifers." In: J.C. Taylor (Ed.) *The Early Calving of Heifers and its Impact on Beef Production*. 143. (1975).

Joseph, R. L. and J. P. Crowley. "Meat Quality of Once-Calved Heifers." Irish J. of Agric. Research 10:281. (1971).

Karabinus, et al., "Effects of Egg Yolk-Citrate and Milk Extenders on Chromatin Structured Viability of Cryopreserved Bull Sperm", Journal of Dairy Science, vol. 74, No. 11, p. 3836-3848. (1999).

Keeling, P. "A Modeling Study of Once-Bred Heifer Beef Production." Proceedings of the New Zealand Society of Animal Production. 51. (1991).

Kinder, J. E., et al. "Endocrine Basis for Puberty in Heifers and Ewes." J. Repro. and Fertility, p. 393. (1995).

Kinder, J. E., et al., "Endocrine Regulation of Puberty in Cows and Ewes." J. Repro. and Fertility, Suppl. 34:167. (1987).

Kinoshita, Shuichi. "Spectroscopic Properties of Fluorescein in Living Lymphocytes," Osaka Uinversity Aug. 7, 1986.

Klindt, J. and J. D. Crouse. "Effect of Ovariectomy and Ovariectomy with Ovarian Autotransplantation on Feedlot Performance and Carcass Characteristics of Heifers." J. Anim. Sci. 68:3481. (1990).

Klosterman, E. W. and C. F. Parker. "Effect of Size, Breed and Sex Upon Feed Efficiency in Beef Cattle." North Central Regional Research Publication 235, Ohio Agric. Research and Development Center 1090:3. (1976).

Kniffen, D. M., et al. "Effects of Long-Term Estrogen Implants in Beef Heifers." J. Anim. Sci. 77:2886. (1999).

Kobata, Akira, "Structures and Functions of the Sugar Chains of Human Chorionic Gonadotropin", in *Glycoprotein Hormones* Chin, W.W. and Boime, I., eds. Serono Symposia, Norwell, MA. p. 19-20. 1990.

Koch, R. M., et al., "Characterization of Biological Types of Cattle-Cycle-II.3." Carcass Composition, Quality and Palatability. J. Anim. Sci. 49:448. (1919).

Kommisrud E., et al. "Comparison of Two Processing Systems for Bull Semen with Regard to Post-Thaw Motility and Nonretum Rates." Theriogenology, vol. 45, 1996, pp. 1515-1521.

Laster, D. B., "Factors Affecting Dystocia and Effects of Dystocia on Subsequent Reproduction in Beef-Cattle." J. Anim. Sci. 36:695. (1973).

Lightwave Electronics, "Xcyte," www.LightwaveElecronics.com.

Lindsey, A. C., et al., "Low Dose Insemination of Mares Using Non-Sorted and Sex-Sorted Sperm" Animal Reproduction Science 68 p. 279-89 (2001).

Liu, Z, et al. "Survival of Bull Sperm Frozen at Different rates in Media Varying in Osmolarity." Cryobiology, vol. 27, 1998, pp. 219-230.

Lonergan, P., et al., "Effect of Time Interval from Insemination to First Cleavage on the Development of Bovine Embryos In Vitro and In Vivo", Therio. p. 326 (1999).

Long, C.R., et al., "In Vitro Production of Porcine Embryos From Semen Sorted for Sex With a High Speed Cell Sorter: Comparison of Two Fertilization Media." Therio. 49(1): 363 (1998) abstr.

Lu, K. H. et al., "In Vitro Fertilization of Bovine Oocytes with Flow-Cytometrically Sorted and Unsorted Sperm from Different Bulls" Therio. abstr.

Lu, K. H., et al., "In Vitro Fertilization with Flow-Cytometrically-Sorted Bovine Sperm", Therio 52, p. 1393-1405. (1999).

Lynch, I. M., et al., "Influence of timing of gain on growth and reproductive performance of beef replacement heifers." J. Anim. Sci. 75:1715. (1997).

Manni, Jeff. "To-Photon Excitation Expands the Capabilities of Laser-Scanning Microscopy,".

Manning, S.T., et al., "Development of Hysteroscopic Insemination of the Uterine Tube in the Mare", Proceedings of the Annual Meeting of the Society for Theriogenology, 1998, p. 84-85.

Martin, A. H., et al., "Characteristics of Youthful Beef Carcasses in Relation to Weight, Age and Sex. III. Meat Quality Attributes." Canadian J. Anim. Sci. 51:305. (1971).

Martin, L. C., et al., "Genetic-effects on Beef Heifer Puberty and Subsequent Reproduction." J. Anim. Sci. 70:4006. (1992).

Martinez, E, A., et al., "Successful Low-Dose Insemination by a Fiberoptic Endoscope Technique in the Sow ", Proceedings Annual Conference of the International Embryo Transfer Society, Netherlands, Therio. vol. 53 p. 201, Jan. 2000.

Matulis, R. J., "Growth and carcass characteristics of cull cows after different times-on-feed." J. Anim. Sci. 65:669. (1987).

Mauleon, P. "Recent research related to the physiology of puberty." In: J.C. Taylor (ed.) *The Early Calvina of Heifers and its Impact on Beef Production*. (1975).

Maxwell, W. and Johnson, L., "Chlortetracycline Analysis of Boar Spermatozoa After Incubation, Flow Cytometric Sorting, Cooling, or Cryopreservation", Molecular Reproduction and Development 46, p. 408-418. (1997).

Maxwell, W. M. C., et al., "The Relationship Between Membrane Status and Fertility of Boar Spermatozoa After Flow Cytometric Sorting in the Presence or Absence of Seminal Plasma" Reprod. Fertil. Dev. vol. 10 p. 433-40 (1998).

Maxwell, W. M. C., et al., "Viability and Membrane Integrity of Spermazota after Dilution and Flow Cytometric Sorting in the Presence or Absence of Seminal Plasma." Reprod. Fertil. Dev. 8:1165-78. (1997).

McCormick, R. J. "The Flexibility of the Collagen Compartment of Muscle." Meat Sci. 36:79. (1994).

McLeod, John H., "The Axicon: A New type of Optical Element", Journal of the Optical Society of America, vol. 44 No. 8, Aug. 1954, Eastman Kodak Company, Hawk-Eye Works, Rochester, New York.

Meilgaard, M., et al., "Sensor Evaluation Techniques." CRC Press Inc., Boca Raton, FL. (1991).

Meinert, C., et al., "Advancing the Time of Ovulation in the Mare With a Short-Term Implant Releasing the GnRH Analogue Deslorelin", Equine Veterinary Journal, 25, p. 65-68 (1993).

Melamed et al, "An Historical Review of the Development of Flow Cytometers and Sorters", 1979, pp. 3-9.

Mendes Jr., J.O.B. "Effect of heparin on cleavage rates and embryo production with four bovine sperm prepration protocols" Theriogenology 60 (2003) 331-340.

Menke,E. A Volume Activated Cell Sorter Journal of Histo chemistry and Cyto Chemistry, 1977, vol. 25,No. 7, pp. 796-803.

Merton, J., et al., "Effect of Flow Cytometrically Sorted Frozen/Thawed Semen on Success Rate of In Vitro Bovine Embryo Production", Therio. 47, p. 295. (1997).

Metezeau P. et al. Improvement of Flow Cytometry Analysis and Sorting of Bull Spermatozoa by Optical Monitoring of Cell Orientation as Evaluated by DAN Specific Probing Molecular Reproduction and Development, 1991,vol. 30 pp. 250-257.

Moe, P. W., "Energetics of Body Tissue Mobilization." J. of Dairy Sci. 54:548.

Moran, C., et al., "Puberty in Heifers—a Review." Animal Reproduction Sci. 18:167. (1989).

Moran, D. M. et al., "Determination of Temperature and Cooling Rate Which Induce Cold Shock in Stallion Spermatozoa", Therio. vol. 38 p. 999-1012 (1992).

Morgan, J. B., et al., "National Beef Tenderness Survey." J. Anim. Sci. 69: 3274. (1991).

Morris, S. T., et al., "Biological efficiency: How relevant is this concept to beef cows in a mixed livestock seasonal pasture supply context?" Proceedings of the New Zealand Society of Animal Production 54:333. (1994).

Moseley, W. M., et al., "Relationship of Growth and Puberty in Beef Heifers Fed Monensin" J. Anim. Sci. vol. 55 No. 2 p. 357-62 (1982).

Mount, D. E. "Fibrous and Non-fibrous Carbohydrate Supplementation to Ruminants Grazing Forage From Small Grain Crops." M.S. Thesis. Abstr. Colorado State University. (2000).

Mullis, K. B. and F. A. Faloona, "Specific Synthesis of DNA in Vitro Via a Polymerase-Catalyzed Chain Reaction" Methods in Enzymology vol. 155 p. 335-350 (1978).

Myers, S. E., "Performance and Carcass Traits of Early-Weaned Steers Receiving Either a Pasture Growing Period or a Finishing Diet at Weaning." J. Anim. Sci. 77:311. (1999).

Myers, S. E., et al., "Comparison of Three Weaning Ages on Cow-Calf Performance and Steer Carcass Traits." J. Anim. Sci. 77:323. (1999).

Myers, S. E., et al., "Production Systems Comparing Early Weaning to Normal Weaning With or Without Creep Feeding for Beef Steers." J. Anim. Sci. 77:300. (1999).

Nix, J. P., et al., "Serum Testosterone Concentration, Efficiency of Estrus Detection and Libido Expression in Androgenized Beef Cows." Therio. 49: 1195. (1998).

Nowshari, et al., "Superovulation of Goats with Purified pFSH Supplemented with Defined Amounts of pLH", Therio. vol. 43, p. 797-802 (1995).

NRC. "Nutrient Requirements for Beef Cattle." National Academy of Sci. National Research Council, Washington, DC. (1996).

O'Brien, Justine K. et al., "Preliminary Developments of Sperm Sorting Technology in Non-human Primates", Biology of Reproduction 2001(Su;;l. 1) 64:158.

Olive, M.D., "Detection of Enterotoxigenic *Escherichia coli* after Polymerase Chain Reaction Amplification with a Tehrmostable DNA Polymerase", J of Clinical Microbiology, Feb. 1989 p. 261-265.

Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).

Owen, J. B. "The Maiden Female-A Means of Increasing Meat Production." Proc. Symp. On the Use of Once Bred Heifers and Gilts. (1973), pp. 70 and 71.

Patterson, D. J., et al., "Estrus Synchronization with an Oral Progestogen Prior to Superovulation of Postpartum Beef Cows" Therio. 48, 1025-33 (1997).

Penfold, L.M.et at., "Comparative Motility of X and Y Chromosome-Bearing Bovine Sperm Separated on the Basis of DNA Content", Mol. Reprod. And Develop. 1998, vol. 50,pp. 323-327.

Petit, M. "Early Calving in Suckling Herds." In: J.C. Taylor (ed.) *The Early Calving of Heifers and its Impact on Beef Production*. p. 157-176. (1975).

Picket B.W., et al., "Livestock Production Science," 1998.

Pickett, B. W., et al., "Influence of Seminal Additives and Packaging Systems on Fertility of Bovine Spermatozoa." J. Anim. Sci. Suppl. II. 47:12. (1978).

Pickett, B. W., et al., "Recent Developments in Artificial Insemination in Horses", Livestock Production Science, 40, p. 31-36 (1994).

Pickett, B. W., et al., "The Effect of Extenders, Spermatozoal Numbers and Rectal Palpation on Equine Fertility." Proc. Fifth N.A.A.B. Tech. Conf. A. I. Reprod. Columbia, MO. pp. 20-22. (1974).

Pinkel et al., "Flow Chambers and Sample Handling", Flow Cytometry: Instrumentation and Data Analysis, Van Dille et al. (Eds.), 1985, pp. 77-128.

Pinkel, D., et al, "Flow Cytometric Determination of the Proportions of X- and Y-Chromosome-Bearing Sperm in Samples of Purportedly Separated Bull Sperm", J. of Anim. Sci., vol. 60, p. 1303-1307 (1998).

Pinkel, D., et al., "Sex Preselection in Mammals? Separation of Sperm Bearing the Y and "O" Chromosomes in the Vole Microtus Oregoni", Science vol. 218 p. 904 (1982).

Piston, D.W. "Three-dimensionally resolved NAD(P)H cellular metabolic redox imaging of the in situ cornea with two-photon excitation laser scanning microscopy," Journal of Microscopy, vol. 178, Nov. 29, 1994.

Polge, E. J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11. (1996).

Polge, et al, "Revival of Spermatozoa After Vitrification and Dehydration at Low Temperatures," Nature, 164:666 (1994).

Preza, C. et al, "Determination of Direction-Independent Optical Path-Length Distribution of Cells Using Rotational-Diversity Transmitted-Light Differential Interference Contrast (DIC) Images", Presented at the Multidimensional Microscopy: Image Acquisition and Processing V. p. 1-11 (1998).

Province, C.A., et al., "Cooling Rates, Storage, Temperatures and Fertility of Extended Equine Spermatozoa Therio. vol. 23 (6) p. 925-934, Jun. 1985.

Purvis, H. T. and J. C. Whittier. "Effects of Ionophore Feeding and Anthelmintic Administration on Age and Weight at Puberty in Spring-Born Beef Heifers." J. Anim. Sci. 74:736-744. (1996).

Randel, R. D. "Nutrition and Postpartum Rebreeding in Cattle." J. Anim. Sci. 68:853. (1990).

Rath, D., et al., "Production of Piglets Preselected for Sex Following in Vitro Fertilization with X and Y Chromosome-Bearing Spermatozoa Sorted by Flow Cytometry", Therio. 47, p. 795-800 (1997).

Rathi, R. et al., "Evaluation of In Vitro Capacitation of Stallion Spermatoza", Biology of Reproduction 2001,vol. 65, pp. 462-470.

Recktenwald, Diether. "Cell Separation Methods and Applications," New York 1997.

Reiling, B.A., et al., "Effect of Prenatal Androgenization on Performance, Location, and Carcass and Sensory Traits on Heifers in Single Calf Heifer System", J. Anim. Sci., 1995, 73: 986, p. 986-992.

Reiling, B.A., et al., "Effects of prenatal Androgenization, Melengestrol Acetate, and Synovex-H on Feedlot Performance, Carcass, and Sensory Traits of Once-Calved Heifers" J. Anim. Sci. vol. 74 p. 2043-51 (199).

Rieger, D., et al, "The Relationship Between the Time of First Cleavage of Fertilized Cattle Oocytes and Their Development to the Blastocyst Stage", Therio. 1999, p. 190.

Rigby, S. L., et al., "Pregnancy Rates in Mares Following Hysterscopic or Rectally-Guided Utero-Tubal insemination with Low Sperm Numbers" Abstracts/Animal Reproduction Science vol. 68 p. 331-333 (2001).

Riggs, B.A. "Integration of Early Weaning and Use of Sexed Semen in a Single-Calf Heifer System to Increase Value of Non-Replacement Heifers" MS Thesis, Colorado State University, Spring 2000.

Romero-Arredondo, A. "Effects of Bovine Folicular Fluid on Maturation of Bovine Oocytes" Theriogenology 41: 383-394, 1994.

Romero-Arrendondo, A. "Effects of Follicular Fluid dring in Virto Maturation of Bovine Oocytes on In Vitro Fertilization and Early Embryonic Development" Biology of Reproduction 55, 1012-1016 1996.

Romita, A. "Some Considerations on the Beef Situation in Italy." In: J.C. Taylor (ed.) *The Early Calving of Heifers and its Impact on Beef Production.* 23. (1975).

Roux, M., et al., "Early Calving Heifers Versus Maiden Heifers for Beef-Production from Dairy herds. I. The Effects of Genotype (Friesian and Carloads x Friesian) and Two Feeding Levels in the Rearing Period on Growth and Carcass Quality." Livestock Prod. Sci. 16:1 (1987).

Roy, J. H., "Rearing Dairy-Herd Replacements." Journal of the Society Of Dairy Technology 31:73-79 (1978).

Rutter, L. M., et al., "Effect of Abomasal Infusion of Propionate on the GnRH-Induced Luteinizing Hormone Release in Prepuberal Heifers." J. Anim. Sci. 56:1167 (1983).

Schenk, J. L. "Applying Semen Sexing Technology to the AI Industry", Proceedings of the 18th Technical Conference on Artificial insemination & Reproduction, 2000.

Schiewe, M. C., et al., "Transferable Embryo Recovery Rates Following Different Insemination Schedules in Superovulated Beef Cattle" Therio. 28 (4) Oct. 1997, pp. 395-406.

Schillo, K. K., et al, "Effects of Nutrition and Season on the Onset of Puberty in the Beef Heifer." J. Anim. Sci. 70:3994 (1992).

Schnell, T. D., et al, "Performance, Carcass, and Palatability Traits for Cull Cows Fed High-Energy Concentrate Diets for 0, 14, 28, 42, or 56 days." J. Anim. Sci. 75:1195. (1997).

Schoonmaker, J. P., et al., "Effects of Age at Weaning and Implant Strategy on Growth of Steer Calves." J. Anim. Sci. (Suppl. II) 76:71. (1998) abstr.

Seidel, G. E. Jr. "Cryopreservation of Equine Embryos" Veterinary Cliniics of North America: Equine Practice vol. 12, No. 1, Apr. 1996.

Seidel, G. E. Jr. "Sexing Bovine Sperm" The AABP Proceedings—vol. 34.

Seidel, G. E. Jr. Sexing mammalian spermatozoa and embryos-state of the art Journal of Reproduction and Fertility Supp 54, 477-487 1999.

Seidel, G. E. Jr et al., "Current Status of Sexing Mammalian Spermatozoa," Society for Reproduction and fertiity, pp. 733-743, 2002.

Seidel, G. E. Jr., "Commercilizing Repreductive Biotechnology—The Approach used by XY, Inc.," Theriogenology, p. 5, 1999.

Seidel, G. E. Jr., "Use of Sexed Bovine Sperm for In Vitro Fertilization and Superovulation", Animal Reproduction and Biotech Lab, CSU, Proceedings of the 2000 CETA/ACTE Convention, Charlottetown, Prince Edward Island, Aug. 2000, pp. 22-24.

Seidel, G. E. Jr., "Status of Sexing Semen for Beef Cattle", Texas A & M University 45th Annual Beef Cattle Short Course and Trade Show Proceedings, Aug. 9-11, p. III24-III27, (1999).

Seidel, G. E. Jr., et al, "Sexing Mammalian Sperm—Overview", Therio. 52: 1267-1272, (1999).

Seidel, G. E. Jr., et al., "Artificial Insemination of Heifers with Cooled, Unfrozen Sexed Semen", Therio. vol. 49 pp. 365 (1998) abstr.

Seidel, G. E. Jr., et al., "Insemination of Heifers with Sexed Frozen or Sexed Liquid Semen." Therio. 51. (in press) (1999) abstr.

Seidel, G. E. Jr., Economics of Selecting for Sex: The Most Important Genetic Trait, Theriogenology 59, (2003), pp. 585-598.

Sell, R. S., et al., "Single-calf Heifer Profitability Compared to Other North Dakota Beef Production Systems." Department of Ag. Eco., North Dakota State University, Ag. Econ. Rpt. 20.

Shabpareh, V. "Methods for Collecting and Maturing Equine Oocytes in Vitro" Theriogenology 40: 1161-1175, 1993.

Shackelford, S. D., et al, "Effects of Slaughter Age on Meat Tenderness and USDA Carcass Maturity Scores of Beef Females." J. Anim. Sci. 73:3304. (1995).

Shapiro, Howard M. MD., PC. "Practical Flow Cytometry Third Edition," New York 1994.

Sharpe, J.C., et al., "A New Optical Configuration for Flow Cytometric Sorting of Aspherical Cells" Horticulture and Food Research Institute of New Zealand Ltd., Hamilton, New Zealand (PNS) Nov. 2, 1997 Abstract.

Sharpe, Johnathan, Thesis; "An Introduction of Flow Cytometry", Ch. 2-2.2, 1997.

Sharpe, Johnathan, Thesis; "Gender Preselection-Principle Scientific Options," Ch. 3.4-3.4.8, 1997.

Sharpe, Johnathan, Thesis; "Sperm Sexing using Flow Cytometry," Ch. 3.5-3.5.8, 1997.

Sharpe, Johnathan, Thesis; "Sperm Sexing-Method of Johnson et al," Ch. 3.6-4.3.4, 1997.

Shorthose, W. R. and P. V. Harris. "Effect of Animal Age on the Tenderness of Selected Beef Muscles." J. Food Sci. 55:1-. (1990).

Silbermann, M., "Hormones and Cartilage. Cartilage: Development, Differentiation, and Growth." pp. 327-368. Academic Press, Inc. (1983).

Simon, M., "The Effect of Management Option on the Performance of Pregnant Feedlot Heifers." M.S. Thesis. Kansas State University. (1983).

Skogen-Hagenson, M. J. et al; "A High Efficiency Flow Cytometer," The Journal of Histochemistry and Cytochemistry, vol. 25, No. 7, pp. 784-789, 1977, USA.

Smith, G. C., et al, "USDA Maturity Indexes and Palatability of Beef Rib Steaks." J. of Food Quality 11:1. (1988).

Smith, G. C., et al., "Relationship of USDA Maturity Groups to Palatability of Cooked Beef." J. of Food Sci. 47:1100. (1982).
Smith, R. L., et al, Influence of Percent Egg Yolk during Cooling and Freezing on Survival of Bovine.
Spectra Physics, The Solid State Laser Company, "Vangaurd 4 Watts of UV from a Quasi-CW, All Solid State Laser," http://www.splasers.com/products/isl_products/vangaurd.html three pages, printed Nov. 14, 2002.
Spectra-Physics Products, "Fcbar" http://www.splasers.com/products/oem_products/ov_fcbar.html two pages printed Nov. 14, 2002.
Spectra-Physics, The Solid State Laser Company, Vanguard 2000HMD 532, www.specra-physics.com.
Spectra-Physics, The Solid State Laser Company, Vanguard 350-HMD 355, www.specra-physics.com.
Squires, E. L, "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, p. 127-130 (1996).
Squires, E.L., "Procedures for Handling Frozen Equine Semen for Maximum Reproductive Efficiency", pp. 1, 39-41, 81-89.
Staigmiller, R.B. "Superovulation of Cattle with Equine Pituitary Extract and Porcine FSH" Theriogenology 37: 1091-1099 1992.
Stap J. Et al Improving the Resolution of Cryopreserved X- and Y-Sperm During DNA Flow Cytometric Analysis with the Addition of Percoll to quench the Fluorescence of Dead Sperm: Academic Medical Center, University of Amsterdam (1998) Journal of Animal Science vol. 76 1998, pp. 1896-1902.
Steel, N. L., "Cost Effectiveness of Utilizing Sexed-Semen in a Commercial Beef Cow Operation", MS Thesis, Colorado State University, Summer 1998.
Steinkamp: "Flow Cytometry" vol. 55, No. 9, Sep. 1984 pp. 1375-1400, New York Review of Scientific Instruments Abstract Only.
Stellflug, J. N., "Plasma Estrogens in Periparturient Cow." Therio 10:269. (1978).
Stevenson, J. S., et al., "Detection of Estrus by Visual Observation and Radiotelemetry in Peripubertal, Estrus-Synchronized Beef Heifers." J. Anim. Sci. 74:729. (1996).
Story, C. E., et al., "Age of Calf at Weaning of Spring-Calving Beef Cows and the Effect on Cow and Calf Performance and Production Economics." J. Anim. Sci. 78:1403. (2000).
Stovel R.T. A Means for Orienting Flat Cells in flow systems Biophysical Journal, 1978,vol. 23,pp. 1-5.
Sumner, A. T. and Robinson, J. A., "A Difference in Dry Mass Between the Heads of X and Y-Bearing Human Spermatozoa", J Reprod Fertil. 48, p. 9-15 (1976).
Swanson, E. W. "Future Research on Problems of Increasing Meat Production by Early Calving." In: J.C. Taylor (ed.) *The Early Calving of Heifers and its Impact on Beef Production*. (1975).
Swenson, S. L., et al., "PRRS Virus Infection in Boars: Isolation From Semen and Effect on Semen Quality" from the 1995 Research Investment Report, Iowa State University, Veterinary Clinical Sciences, Iowa State University.
Tatum, J. D., et al., "Carcass Characteristics, Time on Feed and Cooked Beef Palatability Attributes." J. Anim. Sci. 50:833. (1980).
Taylor, C. S., "Efficiency of Food Utilization in Traditional and Sex-Controlled Systems of Beef Production", AFRC Animal Breeding Research Organization, West Mains Road, Edinburg EH9 3JQ, pp. 401-440.
Tervit, H.R., et al., "Successful Culture In Vitro of Sheep and Cattle Ova", Agricultural Research Council, Unit of Reprod. Physio. and Biochem., Univ of Cambridge, p. 493-497 (1972).
Thun, Rico, et al., Comparison of Biociphos-Plus® and TRIS-Egg Yolk Extender for Cryopreservation of Bull Semen; Theriogenology Symposium, Dec. 1999, vol. 52, #8.
*Time-Bandwidth Products* "GE-100-XHP". www.tbsp.com. 2 pages, Jan. 2002.
Unruh, J. A. "Effects of Endogenous and Exogenous Growth-Promoting Compounds on Carcass Composition, Meat Quality and Meat Nutritional-Value." J. Anim. Sci. 62:1441. (1986).
USDA "Official United States Standards for Grades of Carcass Beef." Agric, Marketing Serv., USDA, Washington, DC. (1997).

Van Dilla, Martin, "Overview of Flow Cytometry: Instrumentation and Data Analysis", Flow Cytometry: Instrumentation and Data Analysis, Van Dilla et al. (Eds.), 1985, pp. 1-8.
Van Munster, E. B., "Geslachtsbepaling met interferometrie", Derde prijs NtvN-prijsvraag voor pas-gepromoveerden 65/4,(Sex Determination with Interferometry) p. 95-98 (1999).
Van Munster, E. B., et al, "Difference in Volume of X- and Y-chromosome Bearing Bovine Sperm Heads Matches Difference in DNA Content" Cytometry vol. 35 p. 125-128 (1999).
Van Munster, E. B., et al, "Measurement-Based Evaluation of Optical Path Length Distributions Reconstructed From Simulated Differential Interference Contrast Images", J of Microscopy 191, Pt. 2, p. 170-176 (1998).
Van Munster, E. B., et al, "Reconstruction of Optical Pathlength Distributions From Images Obtained by a Wide Field Differential Interference Contrast Microscope", J of Microscopy 188, Pt. 2, p. 149-157 (1997).
Vazquez, J. J. et al., "Nonsurgical Uterotubal Insemination in the Mare", Proceedings of the 44th Annual Convention of the American Association of Equine Practitioners, vol. 44, pp. 68-69 (1998).
Vincent, B.C., et al, "Carcass Characteristics and Meat Quality of Once-Calved Heifers." Canadian J. Anim. Sci. 71:311. (1991).
Vogel, T., et al, "Organization and Expression of Bovine TSPY", Mammalian Genome, vol. 8, pp. 491-496 (1997).
Watson, "Recent Developments and Concepts in the Cryopreservvation of Spermatozoa and the Assessment of Their Post-Thawing Function," Reprod. Fertil. Dev. 7:871-891 (1995) Abstract.
Welch, G., et al., "Flow Cytometric Sperm Sorting and PCR to Confirm Separation of X- and Y-Chromosome Bearing Bovine Sperm", Animal Biotechnology, 6, pp. 131-139 (1995).
Wheeler, T. L., et al., "Effect of Marbling Degree on Beef Palatability in Bos-taurus and Bos-inducus cattle." J. Anim. Sci. 72:3145. (1994).
Wickersham, E. W. and L. H. Schultz. "Influence of Age at First Breeding on Growth, Reproduction, and Production of Well-Fed Holstein Heifers." J. Dairy Sci. 46:544. (1963).
Wilhelm, K.M. et al, "Effect of Phosphatidylserine and Cholesterol Liposomes on the Viability, Motility, and Acrosomal Integrity of Stallion Spermatozoa Prior to and after Cryoopreservation", Cryobiology 33:320, 1996.
Wilson, D. E. et al., "Mammal Species of the World", Smithsonian Institution Press, 1993, 1206 pp.
Windsor, D. P., et al, "Sex Predetermination by Separation of X and Y Chromosome-bearing Sperm: A Review", Reproduction of Fertilization and Development 5, pp. 155-171, (1993).
Zhou, Hongwei, et al. "Research on and Development of Flow Cell Sorting Apparatuses," Gazette of Biophysics, vol. 13, ed. 3, 1997—translation of abstract only.
Hamamatsu, "*Photomultiplier Tubes,*" web page, http://www.optics.org/hamamatsu/pmt.html. Printed on Apr. 15, 2000 4.
Hermesmeyer, G.N., et al. Effects of Lactation and Prenatal Androgenization on the Performance, Carcass Composition, and Longissimus muscle sensory characteristics of heifers in the single-calf heifer system. The Professional Animal Scientist 15: 14-23.
Seidel, G. E. Jr., "Fertility of Bulls on the Edge of the Dose-Response Curve for Numbers of Sperm per Inseminate"; Proceedings of the 17th Technical Comference on Artificial Insemination & Reproduction, 1998.
Hollinshead, F.K. et al. "In vitro and in vivo assessment of functional capacity of flow cytometrically sorted ram spermatozoa after freezing and thawing." Reprod. Fertil. And Develp. 2003. vol. 15, pp. 351-359.
Hollinshead F. K. et al. "Production of lambs of predetermined sex after the insemination of ewes with low numbers of frozen-thawed sorted X- or Y-Chromosome-bearing spermatozoa", Reprod. Fertil. And Develop. 2002, vol. 14, pp. 503-508.
Hollinshead F. K. et al. "Sex-Sorting and Re-cryopreservation of Frozen-Thawed Ram Sperm for In Vitro Embryo Production" Theriogenology, vol. 59. (2003) pp. 209.
Dhali et al. Vitrification of Buffalo (*Bubalus bubalis*)Oocytes, Embryo Theriogenology vol. 53, pp. 1295-1303 (2000).
Borini et al. Cryopreservation of Mature Oocytes: The use of a trypsin inhibitor enhances fertilization and obtained embryos rates, Fertil. Steril. (1997), vol. 68 (Suppl.).

Cran et al. The predetermination of embryonic sex using flow cytometrically separated X and Y spermatozoa, Human Reproduction Update 1996, vol. 2, No. 4 pp. 355-363.

Hamamatsu Photonics K.K. Electronic Tube Center, Photomultiplier Tubes, Brochure Dec. 1997.

Johnson, L. A., et al. The Beltsville Sperm Sexing Technology: High-speed sperm sorting gives improved sperm output for In Vitro fertiliation and AI, Journal of Animal Science,vol. 77, Suppl 2/J, Dairy Sci. vol. 82, Suppl. Feb. 1999 pp. 213-220.

Peters D., The LLNL high-speed sorter: Design features,operational characteristics, and bioloical utility, Cyometry, 6:290-301 (1985).

Rens W., et al Slit-scan flow cytometry for consistent high resdolution DNA analysis of X- and Y -chromosome bearing sperm, Cytometry 25:191-199 (1996).

van Munster, E. B. Interferometry in for to sort unstained X- and Y-Chromosome-Bearing Bull Spermatozoa, Cytometry 47:192-199 (2002).

Scmid, R. L., et al. Effects of follicular fluid or progesterone on in vitro maturation of equine oocytes before intracytoplasmic sperm injection with non-sorted and sex-sorted spermatozoa, Journal of Reproduction and Fertility 56:519-525, 2000.

Spectra-Physics, The Solid State Laser Company, Vanguard 350-HMD 355, User's Manual, Dec. 2002.

Photon, Inc. Light MeasuringSolutions, NanoScan for High-powered beam Applications, 2005.

Fluorescense Lifetime Systems, www.picoquant.com, Jan. 28, 2005 pp. 2.

NCI ETI Branch, Flow CytometryCore Laboratory, http://home.ncifcrf.gov/ccr/flowcore/ndyag.htm, pp. 5, May 11, 2004.

NCI ETI Branch, Flow CytometryCore Laboratory, http://home.ncifcrf.gov/ccr/flowcore/lsrll.htm, pp. 14, May 11, 2004.

Saacke,R.G., Can Spermatozoa with abnormal heads gain access to the ovum in artificially inseminated super- and single-ovulating cattle?, Theriogenology 50:117-128. 1998.

Hawk, H.W., Gamete Transport in the Superovulated Cow. Theriogenology: Jan. 1998 vol. 29 No. 1 pp. 125-142.

Bedford, S. J. and Hinrichs, K., "The Effect of Insemination Volume on Pregnancy Rates of Pony Mares", Therio. 42:571-578. (1994).

Berger, G. S. "Intratubal Insemination", Fertil. Steril. 48:328-330, (1987).

Chin, W. W. and Boime, I. 1990. In Glycoprotein Hormones. Serona Symp. Norwell, MA. pp. 19-20.

Purse!, et al, "Effect of Orvus ES Paste on Acrosome Morphology, Motility and Fertilizing Capacity of Frozen-Thawed Boar Sperm," Journal of Animal Science, 47:1:198-202 (1978).

Waggoner, A. W., et al., "Performance, Carcass, Cartilage Calcium, Sensory and Collagen Traits of Longissimus Muscles of Open Versus 30-month-old Heifers That Produced One Calf." J. Anim. Sci. 68:2380. 1990.

Blecher, S.R., et al. A new approach to immunological sexing of sperm, Theriogenology, 59, pp. 1309-1321, 1999 vol.

Wheeler, M. B., et al. Application of sexed semen technology to in vitro embryo production in cattle, Theriogenology, vol. 65 (2006) 219-227.

Garverick, H. A., et al. mRNA and protein expression of P450 aromatase (AROM) and estrigen receptors (ER) α and β during early development of bovine fetal ovaries; The society for the study of reproduction 38th annual meeting Jul. 24-27, 2005; Abstract only.

Bodmer, M., et al., Fertility in heifers and cows after low does insemination with sex-sorted and non-sorted sperm under field conditions; Theriogenology, vol. 64, (2005) 1647-1655.

Schenk J. L., et al. Embryo production from superovulated cattle following insemination of sexed sperm, Theriogenology, 65 (2006) 299-307.

Garner, D. L., Flow cytometric sexing of mammalian sperm, Theriogenology, 65 (2006) 943-957.

Habermann F. A., et al., Validation of sperm sexing in the cattle (*Bos taurus*) by dual colour flourescence in situ hybridization; J Anim Breed Genet. Apr. 2005; 122 Suppl 1:22-7 (Abstract only).

Johnson, L. A., Sexing mammalian sperm for production of offspring: the state-of-the-art; Animal Reproduction Science; 60-61 (2000) pp. 93-107.

Andersson, M. et al., Pregnancy Rates in Lactating Holstein-Greisian Cows after Artificial Insemination with Sexed Sperm. Reprod. Dom. Anim 41, 95-97, 2006.

Morton, K. M., et al., In vitro and in vivo survival of bisected sheep embryos derived from frozen-thawed unsorted, and frozen-thawed sex-sorted and refrozen-thawed ram spermatozoa; Theriogenology, 65 (2006) 1333-1345.

Wilson, R. D., et al., In vitro production of bovine embryos using sex-sorted sperm, Theriogenology, 65 (2006) 1007-1015.

Johnson, L.A., et al, 1996 Gender preselection in mammals. XX Beltsville Symposium in Agricultural Research Technolgy's Role in the Genetic Improvement of Farm Animals. pp. 151-164, Amer. Soc. Anim. Sci. IL, USA.

Smorag, Z., et al., Cattle Sex Regulation by Separation of X and Y Spermatozoa—Preliminary Results of Field Experiment in Poland, Reproduction, Fertility and Development 17(2) 306-306; Jan. 1, 2005.

Crichton, E., et al. (Abstract) Artificial Insemination of Lactating Holstein Cows with Sexed Sperm, Reproduction, Fertility and Development 18(2) 281-281, Dec. 14, 2005.

Lindsey, A.C., et al. Hysteroscopic insemination of low numbers of flow sorted fresh and frozen/thawed stallion spermatozoa, EquineVet J. Mar. 2002;34(2):106-7.

Drobnis, E. Z, Cold shock damage is due to lipid phase transitions in cell membranes : a demonstration using sperm as a model, Journal of experimental zoology (J. exp. zool.) 1993, vol. 265, No. 4, pp. 432-437 (22 ref.).

Hagele, W.C., et al., Effect of Separating Bull Semen into X and Y Chromosome-bearing Fractions on the Sex Ratio of Resulting Embryos; Cran J. Comp. Med, 1984: 48:294-298.

Suh, T.K, et al., Pressure during flow sorting of bull sperm affects post-thaw motility characteristics; Theriogenology vol. 59, No. 1, Jan. 2003 p. 516.

Rath, D, et al., In Vitro Production of Sexed Embryos for Gender Preselection: High-speed sorting of X-Chromosome-Bearing Sperm to Produce Pigs After Embryo Transfer, J. Anim. Sci. 1999, 77:3346-3352.

Auchtung, T.L., et al., Effects of Photoperiod During the Dry Period on Prolactin, Prolactin Receptor, and Milk Production of Dairy Cows; Journal of Dairy Sci. 88: 121-127; American Dairy Sci. Assoc., 2005.

Bailey, Tom and Currin, John Milk Production Evaluation In First Lactation Heifers; 1999 Virginia Cooperation Extension/Dairy Science Publication 404-285.

Belloin, J.C., Milk and Dairy products: prduction and processing costs Food and Agriculture Organization of United Nations Rome 1988 FAO; web page where found: www.fao.org/docrep/003/x6931e/X6931E00.htm.

Kume, Shin-ichi; Dept of Animal Nutrition National Institute of Animal Industry Tsukuba 305, Japan The Dairy Industry $In Asia B. Japan; www.agnet.org/library/article/eb384b.html.

Crichton,E.; Huffman,S.;McSweeney,K.;and Schenk, J. 347 Artificial Insemination of Lactating Holstein Cows with sexed sperm: Abstract CSORP Publishing—Reproduction, Fertility and Development www.publish.csiro.au/nid/44/paper/RDv18n2Ab347.htm.

Lopez, H.,Caraviello, D.Z., Satter, L.D., Fricke, P.M. and Wiltbank, M.C.; Relationship Between Level of Milk Production and Multiple Ovulation in Lactating Dairy Cows Journal of Dairy Sci. 88:2783-2793; American Dairy Science Association, 2005.

Managing the Dairy Cow During the Dry Period; Dairy Cattle Production 341-450A; Macdonald Campus of McGill University/Faculty of Agricultural & Environmental Sciences/Department of Animal Science.

Milk Production and Biosynthesis University of Guelph/Dairy Science and Technology www.foodsci.uoguelph.ca/dairyedu/biosyntheses.html p. 1-5.

Milk Production Released Jul. 18, 2006, by the National Agricultural Statistics Service (NASS), Agri. Stats. Board, US Dept of Agri.

DeVries, A. Economic Value of Pregnancy in Dairy Cattle Journal of Dairy Sci. 89:3876-3885/American Dairy Sci. Assoc. 2006.

Garner, D.L. et al., Viability Assessment of Mammalian Sperm Using SYBR-14 and Propidium Lodide, 1996, Biology of Reporduction, vol. 53, pp. 276-284.

Salisbury, G.W. et al., Substrate-Free Epididymal-Like Bovine Spermatozoa, J Repord Fertil, 1963, vol. 6, pp. 351-359.

Wong, P.Y.D., et al. Potassium Movement During sodium-Induced Motility Initiation in the Rat Caudal Epididymal Spermatozoa; Biology of Reproduction 28, 206-212 (1983).

Shirai, H., et al. Regulation of Sperm Motility in Starfish; Development, Growth, and Differentiation; 24, (5), 419-428 (1982).

Padilla, A.W. et al. Extender and Centrifugation Effects on the Motility Patterns of Slow-Cooled Stallion Spermatozoa; J. Anim. Sci 1991, 69:3308-3313.

Ohta H., et al., Acquisition and Loss of Potential for Motility Ofspermatozoa of the Japanese Eel Anguilla Japonica, National Research Institute of Aquaculture, UNJR Aquiculture; 28th Panel Proceedings (1999).

Morisawa, M. The Process of the Initiation of Sperm Motility; Laboratory of Physiology, Ocean Research Institute, University of Tokyo (1986).

McGrady, A.V., et al. Cholinergic Effects on Bull and Chimpanzee Sperm Motility; Biology of Reproduction 15, 248-253 (1976).

Klinc, P. Dissertation—Improved Fertility of Flowcytometrically Sex Selected Bull Spermatozoa, School of Veterinary Medicine Hanover Germany, 2005.

Jones, J.M. et al Acidification of Intracellular pH in Bovine Spermatozoa Suppresses Motility and Extends Viable Life, Journal of Andrology, vol. 21, No. 5, September/October 616-624.

Jenkins, A. D., et al. Concentrations of Seven Elements in the Intraluminal Fluids of the Rat Seminiferous Tubules, ReteTestis, and Epididymis; Biology of Reproduction 23, 981-987 (1980).

Darszon, A., et al. Ion Channels in Sperm Physiology, Physiological Reviews, vol. 27, No. 2, Apr. 1999.

Christen, R., et al. Metabolism of Sea Urchin Sperm, the Journal of Biological Chemistry, vol. 25, No. 9, Issue of May 10, pp.

Babcock, D. F., et al. Potassium-dependent increases in cytosolic pH stimulate metabolism and motility of mammalian sperm, Proc. Natl. Acad. Sci. USA, vol. 80, pp. 1327-1331, Mar. 1983.

Zilli, L., et al. Adenosine Triphosphate Concentration and β-D-Glucuron idase Activity as Indicators of Sea Bass Semen Quality; Biology of Reproduction 70,1679-1684 (2004) Published online before print Feb. 11, 2004.

Hanania, E. G, et al. A novel Automated Method of Scanning Cytometry and Laser-Induced Necrosis Applied to Tumor Cell Purging, Blood. Nov. 15, 1999, vol. 94, No. 10, suppl 1 part 1.

Purdy, P. H. et al., Effect of Adding Cholesterol to Bull Sperm Membranes on Sperm Capacitation, the Acrosome Reaction, and Fertility, Biology of Reproduction 71, 522-527 (2004).

Purdy, P. H. et al., Effect of cholesterol-loaded cyclodextrin on the cryosurvival of bull sperm, Cryobiology 48 (2004) 36-45.

Moce E., et al., Cholesterol-loaded cyclodextrins added to fresh bull ejaculates improve sperm cryosurvival, J. Anim. Sci, 2006, 84:826-833.

Ereth, B.A., et al. Integration of Early Weaning and Sexed Semen into a Single-Calf Heifer System to Increase Value of Non-Replacement Heifers; Proceedings, Western Section, American Society of Animal Science, vol. 51, 441-443, Jun. 2000.

Ereth, B.A., et al. Integration of Early Weaning and Sexed Semen into a Single-Calf Heifer System to Increase Value of Non-Replacement Heifers; Abstract Only, Journal of Animal Science, vol. 78, Supplement 2, 2000.

Bavister, B.D. et al., The effects of Sperm Extracts and Energy Sources on the Motility and Acromosome Reaction of hamster Spermatozoa in vitero; Biology of Reproduction 16, 228-237 (1997).

Fattouh, El-S.M. et al., Effect of Caffine on the Post-Thaw Motility of Buffalo Spermatozoa; Theriogenology, Jul. 1991, vol. 36 No. 1.

Koh-ichi Hamano, et al., Gender Preselection in Cattle with Intracytoplasmically injected, flow cytometrically sorted sperm heads, Biology of Reproduction 60, 1194-1197 (1990).

Hollinshead, F.K. et al., Birth of lambs of pre-determined sex after in vitro production of embryos using frozen-thawed sex-sorted and re-frozen-thawed ram spermatozoa, Reproduction (Cambridge, England) May 2004, vol. 127, o. 5, pp. 557-568.

Nikkei Biotech, Supplement, Latest Information of Biological Instruments and Reagents, 1988, pp. 93-94.

Parallel Japanese Application No. 2000-526614, Office Action dated May 24, 2006.

Parallel Japanese Application No. 2002-044035, Office Action dated May 24, 2006.

Parallel Russian Application No. SE 2290/17; Office Action dated Mar. 24, 2006.

U.S. Appl. No. 09/582,809; Office Action dated May 1, 2006.

U.S. Appl. No. 09/582,809, Office action dated Jan. 18, 2007.

U.S. Appl. No. 10/378,109; Office action dated Feb. 15, 2006.

U.S. Appl. No. 10/378,109; Office action dated Aug. 31, 2006.

Pursley, J.R. et al., Reproductive Management of Lactating Dairy Cows Using Synchronization of Ovulation; 1997 J. Dairy Sci 80:301-306.

Bagnato, A., Genetic and Breeding; Phenotypic Evaluation of Fertility Traits and Their Association with Milk Production of Italian Friesian Cattle; 1994 J. Dairy Sci 77:874-882.

Panskowski, J., A., et al. Use of Prostaglandin F2a as a Postpartum Reproductive Management Tool for Lactating Dairy Cows; 1995 J. Dairy Sci 78:1477-1488.

Scipioni, R. L., et al., Short Communication: An Electronic Probe Versus Milk Protesterone as Aids for Reproductive Management of Small Dairy Herds; 1999 J. Dairy Sci 82:1742-1745.

Fricke, P. M., Scanning the Fugure—Ultrasonography as a Reproductive Management Tool for Dairy Cattle; J. Dairy Sci 85:1918-1926.

Grant, V. J., et al., Sex-Sorted Sperm and Fertility: An Alternative View; Biology of Reproduction 76, 184-188 (2007).

Garner, D. L, Sex-Sorting Mamallian Sperm: Concept to Application in Arnimls; Journal of Andrology, vol. 22, No. 4 Jul./Aug. 2001.

Tubman, L.M. et al., Characteristics of calves produced with sperm sexed by flow cytometry/cell sorting; 2004 Amer. Society of Animal Sciences; 82:1029-1036.

Weigel, K. A., Exploring the Role of Sexed Semen in Dairy Production Systems; J. Dairy Sci. 87: (E.Suppl.): E120-E130; 2004 American Dairy Science Assoc.

Ferre, L., et al., In vitro-derived embryo production with sexed and unsexed semen from different bulls; Reproduction Fertility and Development, vol. 16, Part 1/2, p. 253, 2004.

Dalton, J.C., et al., Effect of Time of Insemination on Number of Accessory Sperm, Fetilization Rate, and Embryo Quality in Nonlactating Dairy Cattle. J Dairy Sci. 84:2413-2418.

Dransfield, M.B.G., et al., Timing of Inseminatio for Dairy Cows Identified in Estrus by a Radiotelemetric Etrus Detection System. 1998 J Dairy Sci. 81:1874-1882.

Maatje, K. et al. Predicting Optimal Time of Insemination in Cows that Show Visual Signs of Estrus by Estimating onset of Estrus with Pedometers.

Nebel, R.L. et al. Timing of Artificial Insemination of Dairy Cows: Fixed Time Once Daily Versus Morning and Afternoon 1994 J Dairy Sci. 77:3185-3191.

Pursley, J. Richard, et al. Effect of Time of Artificial Insemination on Pregnancy Rates, Calving Rates, Pregnancy Loss, and Gender Ratio After Synchronization of Ovulation in Lactating Dairy Cows. 1998 J Dairy Sci. 81: 2139-2144.

Rozeboom, K. J. et al. Late Estrus or Metestrus Insemination After Estrual Inseminations Decreases Farrowing Rate and Litter Size in Swine J. Animal Sci. 1997. 75: 2323-2327.

Peeler, I. D. et al. Pregnancy Rates After Times AI of Heifers Following Removal of Intravaginal Progesterone Inserts, J. Dair Sci., 87:2868-2873; 2004.

Rath, D. Low Dose Insemination in the Sow—A Review, Reprod. Dom Anim. 37, 201-205 (2002) www.blackwell.de/synergy.

Lukaszewicz, M. et al. Attempts on freezing the Greylag (Anser anser L.) gander semen Animal Reproduction Science 80 (2004) 163-173.

Foote, R. H. et al. Sperm Numbers Inseminated in Dairy Cattle and Nonreturn Rates Revisited 1997 J Dairy Science 80:3072-3076.

Conley, H.H. et at. Intensification by Intrauterine Devices of Sperm Loss from the Sheep Uterus Biology of Reproduction 2, 401-407 (1970).

Chrenek, Peter et al. Fertilizing Capacity of Transgenic and Non-Transgenic Rabbit Spermatozoa after Heterospermic Insemination Bull Vet. Inst. Pulawy 49, 307-310, 2005.

Bakst, Murray R. Fate of Fluorescent Stained Sperm following Insemination: New Light on Ovicucal Sperm Transport and Storage in the Turkey.

Johnson L.A., et al. use of boar spermatozoa for artificial insemination, II. Fertilization Capacity of fresh and frozen spermatozoa in gilts inseminated either at a fixed time or according to walsmeta readings, Journal of Animal Science, vol. 54 No. 1, 1982 pp. 126-131.

Pursel, V. G., et al. Distribution and morphology of fresh and frozen-thawed sperm in the reproductive tract of gilts after artificial insemination; Biology of Reproduction 19, 69-76 (1978).

Rath, D., "On the Status of Sex-Specific Sperm Sorting" Review lecture ET Conference 2002, Department of Animal Production and Animal Behaviour, Mariensee, Germany.

de Graaf, S.P. et al., Birth of offspring of pre-determined sex after artificial insemination of frozen-thawed, sex-sorted and re-frozen-thawed ram spermatozoa, Theriogenology, 67 (2007) 391-398.

O'Brien, J.K. et al., Development fo sperm sexing and associated assisted reproductive technology for sex preselection of captive bottlenose dolphins, Reproduction Fertility and Development, 2006, 18, 319-329.

Zhang, M, et al., In vitro fertilization with flow-sorted buffalo sperm, Reproduction Fertility and Development, 2005, 18 (2), 283-284.

Schenk, J.L. et al., Insemination of cow elk with sexed frozen semen, 2003 Theriogenology 59, 514.

BD Biosciences Brochure, BD FACSCalibur Flow Cytometer, the Automated, Multicolor Flow Cytometry System, 2006.

Johnson, L. A. et al., Cryopreservation of flow cytometrically sorted boar sperm: effects on in vivo embryo developmen; J. Anim Sci. vol. 78, Suppl 1/J. Dairy Sci., vol. 83, Suppl 1, 2000.

Lindsey, A., et al., "Hysteroscopic Insemination of Fresh and Frozen Unsexed and Sexed Equine Spermatozoa", pp. 152-153, Proc. 5th Int. Symp. Equine Embryo Transfer, p. 13, 2000.

Presicce, G.A., et al., First established pregnancies in mediterranean italian buffaloes (Bubalus bubalis) following deposition of sexed spermatozoa near the utero tubal junction, Reproduction in Domestic Animals, vol. 40, No. 1, Feb. 2005, pp. 73-75(3).

Grossfeld, R., "Experiments to Improve the Quality of Sex-Sorted Fresh and Frozen Porcine Spermatozoa" PhD thesis of the Faculty of Agricultural Sciences, Georg-August University, Gottingen, May 2007.

Dielemann, S.J., Superovulation in cattle: from understanding the biological mechanisms to genomics of the oocyte; 23rd Annual Meeting A.E.T.E.—Alghero; Sep. 2007.

Hasler, J. F., Factors influencing the success of embryo transfer in cattle; 23rd World Buiatrics Congress, Quebec, Canada Jul. 2004.

Mapletoft, R. J. et al., Superovulation in perspective, Bioniche Animal Health, Dec. 2002.

Parallel Norwegian patent Application No. 2000 3424-XY, Inc. Official Action dated May 31, 2007.

Parallel Chinese patent Application No. 98813255.9 Official Action dated Oct. 26, 2007.

Bahr, G.F. et al., Considerations of volume, mass, DNA, and arrangement of mitochondria in the midpiece of bull spermatozoa, Experimental Cell Research 60 (1970) 338-340.

Baumber, J., et al., "The Effect of Reactive Oxygen Species on Equine Sperm Motility, Viability, Acrosomal Integrity, Mitochondrial Membrane Potential, and Membrane Lipid Peroxidation", 2000, Journal of Andrology, vol. 21 (6),pp. 895-902.

BD LSR II Flow Cytometer, BD Biosciences Clontech Discovery labware Immunocytometry systems Pharmingen Jan. 28, 2004, pp. 1-8.

Bermudez, D.et al., The immediate effect of IR, laser radiation on rat, germ, cells, was studied by cytophotometric quantification, Scisearch, Adrologia. 1991.23, abstract only.

Sequent Biotechnologies Inc., Welcome to the Sequent Biotechnologies Inc. website., http://www.sequentbiotech.com/ Dec. 6, 2003.

Sabuer K. et al."Effects of Angiotensin II on the Acrosome Reaction in Equine Spermatozoa" Journal of Reproduction and Fertility vol. 120, 2002 p. 135-142.

Brooks, D.E., Manipulation of Mammalian Gametes in Vitro, Biennial Report, Waite Agricultural Research Institute 1986-1989.

Bruemmer, J.E. et al., "Effect of Pyruvate on the Function of Stallion Spermatozoa Stored for up to 48 Hours", Journal of Animal Science 2002, vol. 80*1, pp. 12-18.

Catt, S.L. et al., Hoechst staining and exposure to UV laser during flow cytometric sorting does not affect the frequency of detected endogenous DNA nicks in abnormal and normal human spermatozoa, Molecular Human Reproduction vol. 3 No. 9 pp. 821-825,(1997).

Chaudhry, P., et al., Casein Kinase II activity and polyamine-stimulated protein phosphorylation of cytosolic and plasma membrane protiens in bovine sperm, Archives of Biochemistry and Biophyeics vol. 271, No. 1 pp. 98-106, May 15, 1989.

Chen, Y. et al., Effects of sucrose, trehalose, hypotaurine, taurine, and blood serum on survival of frozen bull sperm, Cryobiology 30,423-431 (1993).

Chapter 16 Semen processing, storage, thawing, and handling, http://nongae.gsnu.ac.kr/~cspark/teaching/chap16.html Sep. 23, 2002.

Conover,J. et al., Pre-loading of mouse oocytes with DNA-specific fluorochrome (Hoechst 33342) permits rapid detection of sperm-oocyte fusion, Journals of Reproductive & Fertility Ltd. 82, 681-690 (1988).

Cressman, B.E. MD, et al., Effect of sperm dose on pregnancy rate from intrauterine insemination: a retrospective analysis, Texas Medicine, 92:74-79 (1996).

Crissman, H.A. et al., Use of DIO-C5-3 to improve hoechst 33342 uptake, resolution of DNA content, and survival of CHO cells, Experimental cell research 174: 338-396 (1988).

Graves, C.N., et al., "Metabolism of Pyruvate by Epididymal-Like Bovine Spermatozoa", 1964 Journal of Dairy Science vol. 47 (12), pp. 1407-1411.

Certified Semen Services, CSS Minimum requirements for disease control of semen produced for AI, http://www.naab-css.org/about_css/disease_control-2002.html Sep. 22, 2003.

De Grooth, B. et al., Simple delay monitor for droplet sorters, Cytometry 12:469-472 (1991).

Lodge, J.R., et al., "Carbon Dioxide in Anaerobic Spermatozoan Metabolism" 1968, Journal of Dairy Science, vol. 51(1), pp. 96-103.

Delgado,N. et al., Correlation between sperm membrane destabilization by heparin and aniline blue staining as membrane integrity index, Archives of Andrology40:147-152 (1998).

Denniston, D.J. et al., "Effect of Antioxidants on the Motility and Viability of Cooled Stallion Spermatozoa", Journal Reproduction Supplement 56, 2001, pp. 121-126.

De Pauw M.C. et al. Sperm Binding to Epithelial Oviduct Explants in Bulls with Different Nonreturn Rates Investigated with a new In-Vitro Model Biology of Reproduction, 2002, vol. 67 p. 1073-1079.

Donoghue, A. et al., Effects of water- and lipid-soluble antioxidants on turkey sperm viability, membrane integrity, and motility during liquid storage, Poultry Science 76:1440-1445 (1997).

Zucker, R. et al., Utility of light scatter in the Morphological analysis of sperm, Cytometry 13:39-47 (1992).

Ericsson, S. et al., Interrelationships among fluorometric analyses of spermatozoal function, classical semen quality parameters and the fertility of frozen-thawed bovine spermatozoal, Theriogenology 39:1009-1024 (1993).

Ericsson, et al. "Flow Cytometric Evaluation of Cryopreserved Bovine Spermatozoa Processed Using a New Antibiotic Combination", Theriogenology, 1990, vol. 33(6), pp. 1211-1220.

Esteves, S. et al., Improvement in motion characteristics and acrosome status in cryopreserved human spermatozoa by swim-up processing before freezing, Human Reproduction vol. 15 No. 10 pp. 2173-2179 (2000).

Evenson, D.et al., Physiology and Management, Rapid determination on sperm cell concentration in bovine semen by flow cytometry, J Dairy Sci. 76: 86-94 (1993).

Farrell et al., "Quantification of Bull Sperm Characteristics measured by Computer-Assisted Sperm Analysis (CASA) and the Relationship of Fertility", Theriogenology, 1998, vol. 49 (4), pp. 871-879.

Fitzgerald, D., Cell sorting: An enriching Experience, The Scientist Jul. 23, 2001.

Foote,R., The history of artificial insemination: Selected notes and notables, American Society of Animal Science (2002).

Johnson, L. et al., Sex preselection in mammals by DSA: A method for flow separation of X and Y Spermatozoa in humans, 1997. In Manual on Assisted Reproduction. 337-349.

Johnson, L. et al., Recent advances in sex preselection of cattle: Flow cytometric sorting of X-&Y-chromosome bearing sperm based on DNA to produce progeny, Theriogenology 41:51-56 (1994).

Ashwood-Smith, M., Debate Human sperm sex selection, Human Reproduction vol. 9 No. 5 pp. 757-759 ( 1994).

Pinkel,D.et al.,Flow cytometry of mammalian sperm progress in DNA and morphology measurement, The Journal of Histochemical and Cytochemistry vol.27 No. 1 pp. 353-358 (1979).

Fugger, E. et al., Birth of normal daughters after MicroSort sperm separation and intrauterine insemination, in-vitro fertilization, or intracytoplasmic sperm injection, http://www.microsort.net/HumRepro.htm Mar. 19, 2003.

Johnson, L. et al., Flow sorting of X and Y Chromosome-bearing Mammalian sperm: Activation and pronuclear development of sorted bull, boar, and ram sperm microinjected into hamster oocytes, Gamete Research 21:335-343 (1988).

Salisbury, G.W., et al., Reversal by Metabolic Regulators of $CO_2$-induced Inhibition of Mammalian Spermatozoa, 1959, Proc Soc Exp Biology Med, vol. 101 (1) pp. 187-189.

Centola, G.et al., Cryopreservation of human semen. Comparison of cryopreservatives, sources of variability, and prediction of post-thaw survival. PMID: 1601749 May-Jun. 1992, abstract only.

Bencic, D.C., et al., "Carbon Dioxide Reversibly Inhibits Sperm Motility and Fertilizing Ability in Steelhead (*Oncorhynchus mykiss*)" 2000, Fish Physiology and Biochemistry, vol. 23(4), pp. 275-281.

Boatman, D.E. et al., "Bicarbonate Carbon Dioxide Regulation of Sperm Capacitation Hyperactivated Motility and Acrosome Reactions", 1991, Biology of Reproduction vol. 44(5), pp. 806-813.

Garcia, M.A. et al., "Development of a Buffer System for Dialysis of Bovine Spermatozoa Before Freezing III.Effect of Different Inorganic and Organic Salts on Fresh and Frozen-Thawed Semen", 1989, Theriogenology, vol. 31(5),pp. 1039-1048.

Eiman, M.et al., Trehalose-enhanced fluidity of the goat sperm membrane and its protection during freezing, Biology of Reproduction 69: 1245-1250 (2003).

Foote, R.et al., Physiology and Management, Fertility of bull spermatozoa frozen in whole milk extender with trehalose, taurine, or blood serum, J. Dairy Sci. 76:1908-1913 (1993).

Johnson, L. et al., Storage of bull semen, Animal Reproduction Science 62: 143-172 (2000).

Johnson, L. et al.,Erratum to "Storage of bull semen", Animal Reproduction Science 62: 143-172 (2000).

McNutt,T.et al., Electrophoretic gel analysis of Hoechst 33342 stained and flow cytometrically sorted bovine sperm membrane proteins, Reprod. Dom Anim.31: 703-709 (1996).

Best, T. P. et al. "Nuclear Localization of Pyrrole-Imidazole Ployamide-Flourescein Conjugates in Cell Culture", PNAS, 2003, vol. 100(21), pp. 12063-12068.

Gygi, M.P., et al. "Use of Fluorescent Sequence-Specific Polyamides to Discriminate Human Chromosomes by Microscopy and Flow Cytometry", Nuci Acids Res. 2002, vol. 30(13),pp. 2790-2799.

BD Biosciences, BD AccuDrop Potion, www.bdbiosciences.com, Sep. 2002.

Agarwal, A.et al., Filtration of spermatozoa through L4 membrane:a new method, Fertility and Sterility, vol. 06, No. 6, Dec. 1991.

Anzar, M.et al., Optimizing and Quantifing fusion of liposomes to mammalian sperm using resonance energy transfer and flow cytometric methods, Cytometry49:22-27 (2002).

Anzar, M.et al., Sperm Apoptosis in fresh and cryopreserved bull semen detected by flow cytometry and it's relationship with fertility, Biology of Reproduction 66: 354-360 (2002).

Arav, A.et al., New trends in gamete's cryopreservation, Molecular and Cellular Endocrinology 187:77-81 (2002).

Arndt-Jovin et al., "Analysis and Sorting of Living Cells According to Deoxyribonucleic Acid Content", Journal Histochem. And Cytochem., 1977, vol. 25(7), pp. 585-589.

Arts,E.et al.,Evidence for the existence of lipid-diffusion barriers in the equatorial segment of human spermatozoa, Boichem J.384:211-218 (1994).

Gadella B,et al., Dynamics in the membrain organization of the mammalian sperm cell and functionality in fertilization, Vet Quart. 21:142-146 (1999).

Garner,D. et al., Morphological and ultrastrutural Characterization of mammalian spermatozoa processed for flow cytometric DNA analyses, Gamete Research 10:339-351 (1984).

Garner, D., et al., Effect of hoechst 33342 staining and laser illumination on the viability of sex-sorted bovine sperm, Theriogenology, vol. 57 No. 1, 1-810 (2002).

Garner, D. et al., Assessment of spermatozoal function using dual fluorescent staining and flow cytometric analyses, Biology of Reproduction 34:, 127-138 (1986).

Gebhard D., Sorting Viability . . . one more time, http://www.cyto.purdue.edu/hmarchiv/1998/2263.htm Feb. 14, 2004.

Givan,A., Flow Cytometry First Principles, (1992).

Gledhill, B.et al., Identifying and separating X- and Y-Chromosome-bearing mammalian sperm by flow cytometry, Lawrence Livermore National Laboratory, Feb. 8, 1984.

Gledhill, B.et al., Flow cytometry and sorting of sperm and male germ cells, Flow Cytometry and sorting, second edition, pp. 531-551 (1990).

Gordon et al., "Genetic Transformation of Mouse Embryos by Microinjection of Purified DNA", Proc. Natil Acad. Sci., 1980, vol. 77 (12), pp. 7380-7384.

Graham, J.et al.,Analysis of sperm cell viability, Acrosomal integrity, and Mitocondrial function using flow cytometry, Biology of Reproduction 43: 55-64 (1990).

Graham, J.et al., Effect of some Zwitter Ion buffers on freezing and storage of spermatozoa I, Bull, J. Dairy Sci 55: 372-378 ( 1992).

Grogan, W. et al., DNA Analysis and sorting of viable mouse testis cells, The Journal of Histochemistry and Cytochemistry, vol. 29 No. 6 pp. 738-746, (1981).

Guthrie, et al., "Flow Cytometric Sperm Sorting: Effects of Varying laser Power on Embryo Development in Swine", Mol. Reprod. And Develop., 2002,vol. 61(1), pp. 87-92.

Hacker-Klom, U.B., et al., Effect of doxorubicin and 4'-epi-doxorubicin on mouse spermatogenesis. Mutation Research International Journal on Mutagenesis vol. 159, pp. 39-46. 1986.

Hasler, J., Symposium: Reproductive Technology and Genetic improvementJ. Dairy Sci. 75:2857-2879 (1992).

Held, A.et al., Quasi- Cw Solid-state lasers Expand their reach, Photonics Spectra, Dec. 2002.

Hinkley, R.et al., Rapid visual detection of sperm-egg fusion using the DNA-Specific Fluorochrome Hoechst 33342, Developmental Biology 118: 148-154 (1986).

Januskauskas, A.et al.,Assessment of sperm quality through Fluorometry and sperm chromatin structure assay in relation to field fertility of frozen-thawed semen from Swedish AI bulls, Theriogenology 55: 947-961 (2001).

Janendran, R.et al., Effect of glycerol and cryopreservation on oocyte penetration by human spermatozoa, PMID: 4025843, Jul. 6, 2006.

Johnson, L., A flow cytometric/ sorting method for sexing mammalian sperm validated by DNA analysis and live births, Cytometry, p. 42 of supplement, Sep. 4, 1990.

Johnson, L., Flow sorting of intact X & Y chromosome-bearingmammalian spermatozoa, The Journal of the Society for Analytical Cytology Cytometry, (1988).

Zhang,M. et al., Development of bovine embryos after in vitro fertilzation of oocytes with a flow cytometrically sorted, stained and unsorted sperm from different bulls, Theriogenology 60: 1657-1663 (2003).

Jones,R.et al., Effect of Osmolality and Phosphate, "Tris", "Tes", "Mes", nd "Herpes" Hydrogen ion buffers on the motility of bull spermatozoa stored at 37 or 5° C., Ausi J. Biol. Sci.25:1047-1055 (1972).

Jones,R., Plasma membrane structures and remodelling during sperm maturation in the epididymis, Journal of Reproduction and Fertility (1998).

Johnson, M.,The Macromolecular Organization of membranes and its bearing on events leading up to Fertilization, Journal of Reproduction and Fertility (1975).

Johnson, L., Progress towards achieving sex preselection in farm animals, USDA Agricultural Research Service, (1989).

Keeler, K. et al., Flow microfluorometric analysis of living spermatozoa stained with Hoechst 33342, J. Reprod.Fert. 68:205-212 (1983).

Keij, J. et al., High speed Photodamage cell sorting: An evaluation of the Zapper Prototype, Methods in cell Biology vol. 42, (1994).

Kirchhoff, C. et al., The Molecular biology of the sperm surface:Post-Testicular Membrane Remodelling, The Fate of the Male Germ Cell, (1997).

Krueger, C. et al., Low dose Insemination in synchronized gilts, Theriogenology 52: 1363-1373 (1999).

Landetie, J., Induction and survival of micronuclei in rat spermatids. Comparison of two meiotic micronucleus techniques using cyclophosphamide, Mutation Research, 203:47-53 (1988).

Laser Innovations—Applications, http://www.laserinnovations.com/488nm.htm Feb. 2, 2004.

Libbus, B. et al., Incidence of chromosome aberrations in mammalian sperm stained with Hoechst 33342 and UV-laser irradiated during flow sorting, Mutation Research, 182: 265-274 (1987).

Loken, M., Separation of viable T and B lymphocytes using a cytochemical stain, Hoechst 33342, The Journal of Histochemistry and Cytochemistry, vol. 28, No. 1, pp. 36-39 (1980).

Lucas, J. et al., Orientation measurments of microsphere doublets and metaphase chromosomes in flow, Cytometry 7:575-581 (1986).

Luttmer, S. et al., Examination of living and fixed gametes and early embryos stained with supravital fluorochromes (Hoechst 33342 and 3,3'-dihexyloxacarocyanine Iodide), Gamete Research 15:267-283 (1986).

Maxwell, W. et al., Physiology of spermatozoa at high dilution rates:The influence of seminal plasma, Theriogenology 52:1353-1362 (1999).

Mazur, P., The role of Intracellular freezing in the death of cells cooled at supraoptimal rates, Cryobiology 14:251-272 (1977).

McSweeney, K. et al., Abstract: Insemination of lactating holstein cows with sexed frozen/thawed sperm, http://www.cvmbs.colostate.edu/physio/abstract/ges12.html Mar. 16, 2004.

Medeiros, C. et al., Current status of sperm cryopreservation: Why isn't it better? Theriogenology 57: 327-344 (2002).

Meistrich, M. et al., "Cytogenetic" studies of spermatids of mice carrying Cattanach's translocation by flow cytometry, Chromosoma 74:141-151 (1979).

Morrell, J. et al., Offspring from inseminations with mammalian sperm stained with Hoechst 33342, either with or without flow cytometry, Mutation Research 224:177-183 (1989).

Morrell et al., "Sexing of Sperm by Flow Cytometry", The Veterinary Record, 1988, pp. 322-324.

Morrier, A. et al., Glycerol addition and conservation of fresh and crypreserved ram spermatozoa, Canadian Journal of AnimalScience, Sep. 2002 http://pubs.nrc-cnrc.gc.ca/aic-journals/2002ab/cjas02/sep02/cjas01-045.html.

Moruzzi, J., Selecting a mammalian species for the separation of X- and Y-chromosome-bearing spermatozoa, J. Reprod. Fert. 57:319-323 (1979).

Murthi S. et al., Improved data acquisition system for digital flow cytometry, (2002).

Studt, T., MEMS-based Cell Sorter Speeds Clinical Studies, R&D Magazine, Dec. 2003: pp. 36-37 as currently presented on and printed from http;//www.rdmag.com 2 pgs.

Gwo-Bin, L. et al., Multi-cell-line micro flow cytometers with buried SU-8/SOG Optical waveguides, Feb. 2002.

Shapiro, H. M. et al., Multistation Multparameter Flow Cytometry: Some Influences of Instrumental Factors on System Performance, 1983, pp. 11-19, 4, AIIan R. Liss, Inc.

OcanaQuero, J. et al., Biological effects of helium-neon irradiation on acrosome reaction in bull, Scisearch Journal of Photochemistry and Photobiology, vol. 40 No. 3, pp. 294-298 (1997).

Pangawkar, G. et al., Physical and biochemical characteristics of semen in relation to fertility of Holstein-Friesian bulls, Indian vet. Med. J. vol. 13: 21-26 (1989).

Papa, S. et al., Chromatin organization in Isolated nuclei: Flow cytometric characterization employing forward and perpendicular light scatter, Cell Biochemistry and Function vol. 6: 31-38 (1988).

Parks, J. et al., Lipids of plasma membrane and outer acrosomal membrane from bovine spermatozoa, Biology of Reproduction 37:1249-1258 (1987).

Perez-Pe, R. et al., Semen plasma proteins prevent cold shock membrane damage to ram spermatozoa, Theriogenology 56 (3):425-434, Aug. 1, 2001, PMID: 11516122 http://www.ncbi.nlm.nih.gov/entrez/query.fcgi?CMD=search&DB=pubmed.

Peter, A. et al., Fractionation of bovine spermatozoa for sex selection: A rapid immunomagnetic technique to remove spermatozoa that contain the H-Y antigen, Theriogenology 40:1177-1185 (1993).

Petersen, Timothy W., et al, Stability of the Breakoff Point in a High-Speed Cell Sorter The Journal of the international society for Analytical Cytology, vol. 56A Num. 2, Dec. 2003.

Pinkel Dan, Flow Cytometry and Sorting Analytical Chemistry, Mar. 1982 vol. 54 No. 3.

Pinkel Dan, Cytometric Analysis of Mammalian Sperm for Induced Morphologic and DNA Content Errors; Biological Dosimetry (Cytometric Approaches to Mammalian Systems) 1984.

Pinkel, D. et al; Radiation-Induced DNA Content Variability in Mouse Sperm. Radiation Research An International Journal, vol. 95, No. 3, Sep. 1983.

Piumi, F. et al., Specific cytogenetic labeling of bovine spermatozoa bearing X or Y chromosomes using florescent in situ hybridization (FISH), Genet, Sel. vol. 33: 89-98 (2001).

Edited by Bell-Prince, C., NFCR Newsletter, http://www.ls.lanl.gov/NFCR/newsletter-Oc98/oct98.html Jan. 6, 2004.

Rasul, Z. et al., Changes in motion characteristics, plasma membrane integrity, and acrosome morphology during cryopreservation of buffalo spermatozoa, Journal of Andrology, vol. 22 No. 2, Mar.-Apr. 2001.

Rees, William A., et al, Betaine Can Eliminate the Base Pair Composition Dependence of DNA Melting; Biochemistry 1993, 32, pp. 137-144.

Rens, W. et al., An X-Y paint set and sperm FISH protocol that can be used for validation of cattle sperm separation procedures, Journals of Reproduction and Fertility, 121: 541-546 (2001).

Reyes-Mereno, C. et al., Characterization of Secretory Proteins from cultured Cauda Epididymal Cells that significantly sustain bovine sperm motility, Molecular Reproduction and Development 63: 500-509 (2002).

Rippel, N. et al., Transcervical insemination: Effects of variation in total sperm number/dose on fertility, 83rd Annual Fall Conference for Veterinarians, Oct. 2002.

Rizzo, W. et al., Liposome-mediated transfer of simian virus 40 DNA and minichromosome into mammalian cells, J. Gen. Virol 64:911-919 (1983).

Ruch, F., Determination of DNA content by microfluorometry, Introduction to Quanitative Cytochemistry, pp. 281-294 (1966).

Saacke, R. et al., Semen Quality test and their relationship to fertility, 4th National Association of Animal Breeders, (1972).

Salisbury, G.W., et al. "Preservation of Bovine Spermatozoa in Yolk-Citrate Diluent and Field Results from its Use", Journal of Dairy Science, 1941, vol. 24(11), pp. 905-910.

Schroter, S. et al., The glycocalyx of the sperm surface, Human Reproduction Update: vol. 5, No. 4, pp. 302-313 (1999).

Schuster, T. et al., Isolation of motile spermatozoa from semen samples using microfluidics, Reproductive BioMedicine Online, vol. 7 No. 1 75-81, www.rbmonline.com/Article/847, Apr. 16, 2003.

Seidel, George E. Jr. "What about sexed semen?" Hoard's Dairyman, The National Dairy Farm Magazine, May 10, 2001.

Sexing Technologies, Welcome to sexing Technologies, http://www.sexingtechnologies.com/ Dec. 11, 2003.

Sharpe, J. et al., Radially symmetric excitation and collection optics for flow cytometric sorting of aspherical cells, Cytometry, 29:363-370 (1997).

Shapiro, H., Re: cheap laser idea??, http://www.cyto.purdue.edu/hmarchiv/1998/1015.htm Feb. 3, 2004.

Smith, P. et al., Characteristics of a Novel Deep Red/ Infrared Fluorescent Cell-Permeant DNA Probe, DRAQ5, in Intact human Cells Analyzed by Flow Cytometry, Confocal and Multiphoton Microscopy, Cytometry 40:280-291 (2000).

Stanger, J. et al., The Relationship between motility and the FITC-BSA binding Properties of Mouse epididymal spermatozoa, The Journal of Experimental Zoology 227: 323-327 (1983).

Stanic, P. et al., Comparison of protective media and freezing techniques for cryopreservation of human semen, http://www.ncbi.nlm.nih.gov/entrez/query.fcgi?CMD=search&DB=pubmed, Jul. 11, 2000.

Stewart, R., Georgia Beef Challenge, Livestock Newsletter Jan.-Feb. 2002.

Takacs, T. et al., Flow Cytometric determination of the sperm cell number in diluted bull semen samples by DNA staining method, Acta Biochim.Biophys.Hung. vol. 22 No. 1, pp. 45-57 (1987).

Thurston, L. et al., Identification of Amplified restriction fragment length polymorphism markers linked to genes controlling boar sperm viability following cryopreservation, Biology of Reproduction 66: 545-554 (2002).

Tone, S. et al., A method of vital staining of mouse eggs using Hoechst dye, Department of Developmential Biology (1986).

Tubman, L. et al., Abstract:Normality of calves resulting from sexed sperm, http://www.cvmbs.colostate.edu/bms/abstract/ges12.html Mar. 16, 2004.

Tucker, K. et al., Sperm separation techniques:Comparison of gradient products, Proceedings 2ed International workshop for Embryologists: Troubleshooting activities in the ART lab. (2002).

Van Dilla, M. et al., Measurement of Mammalian Sperm Deoxyribonucleic acid by Flow Cytometry, The journal of Histochemistry and Cytochemistry vol. 25 No. 7 pp. 763-773 (1977).

Vazquez, J. et al., Nonsurgical Uterotubal Insemination in the Mare, Reproduction: Mare vol. 44 (1998).

Vishwanath, R. et al., Storage of bovine semen in liquid and frozen state, Animal Reproduction Science 62: 23-53 (2000).

Washburn, S., Sex-Sorted Semen; Still several steps short of sensational, http://www.cals.ncsu.edu/an sci/extention/animal/news/april96/april1965.html Mar. 16, 2004.

Welch, G. et al., Sex preselection: Laboratory Validation of the sperm sex ratio of Flow sorted X- and Y-sperm by sort reanal ysis for DNA, Theriogenology 52:1343-1352 (1999).

Welch, G. et al., Fluidic and optical modification to a facs IV for flow sorting of X&Y Chromosomes bearing sperm based on DNA, International Society for Analytical Cytology (1994).

Wiltshire, M. et al., A Novel Deep Red/ Low infrared fluorescent flow cytometric probe DRAQ5NO, For the Discrimination of intact nucleated cells in apoptotic cell populations, Cytometry 39: 217-223 (2000).

Woelders, H. et al., Effects of Trehalose and Sucrose, Osmolality oh the freezing medium, and cooling Rate on Viability and intactness of bull sperm after freezing and thawing, Cryobiology 35: 93-105 (1997).

Wolf, D., Lipid domains in sperm plasma membranes, Molecular Membrane Biology 12: 101-104 (1995).

Wolf, D. et al., Changes in sperm plasma membrane lipid diffusibility after hyperactivation during In vitro capacitation in the mouse, The Journal of Cell Biology, vol. 102: 1372-1377(1986).

Wolf, D. et al., Diffusion and regionalization in membranes of maturing ram spermatozoa, The Journal of Cell Biology, vol. 98:1678-1684 (1984).

XY Files, Issue 1 Jun. 1999.

XY, Inc., Sex selection Procedure, http://www.xyinc.com/sex select.html, Feb. 21, 2003.

XY Files, Issue 4 Aug. 2000.

XY Files, Issue 2 Oct. 1999.

XY Files, Issue 3 Mar. 2000.

XY Files, Issue 5 Mar. 2001.

XY Files, Issue 6 Mar. 2002.

Lindsey, A. C., et al., Hysteroscopic inseminatin of mares with low numbers of nonsorted or flow sorted spermatozoa; Equine vet. J. (2002) 34(2) 128-132.

Sharpe, Johnathan, Advances in flow cytometry for sperm sexing, Unpublished paper, 2008.

Johnson, S.K., Possibilities with today's reproductive technologies. Available online at www.sciencedirect.com; Therio 64(2005) pp. 639-656.

Brogliatti, G. et al., Pregnancy Rates and First Born Calves by Artificial Insemination using Sexed Semen in Argentina: Therio. Jan. 2, 2002, vol. 57, No. 1. p. 369.

Gottlinger, Christopher et al., Cell-Cooling in Flow Cytometry by Peltier Elements. Cytometry 7:295-297 (1986).

Abstracts: American Dairy Science Assoc., American Society of Animal Science, Jun. 22-26, 2003 Phoenix AZ. J.Anim Sci. vol. 81 Suppl.1/J. Dairy Sci. vol. 86, Suppl. 1.

Garner, Duane L., et al, Effect of Semen Dilution on Bovine Sperm Viability as Determined by Dual-DNA Staining and Flow Cytometry. J. of Andrology, vol. 18, No. 3 May/Jun. 1997.

Lindsey, A. L., et al., Hysteroscopic or rectally guided, deep-uterine insemination of mares with spermatozoa stored 18 h at either 5° C or 15° C prior to flow-cytometric sorting, Animal Reproduction Science, vol. 85, Issues 1-2, Jan. 2005, pp. 125-130.

Office Action, U.S. Appl. No. 09/582,809, dated Sep. 28, 2007.

Office Action, U.S. Appl. No. 09/582,809, dated Jul. 21, 2008.

Office Action, U.S. Appl. No. 09/582,809, dated Feb. 27, 2009.

Office Action, U.S. Appl. No. 11/613,605, dated Mar. 24, 2008.

Office Action, U.S. Appl. No. 11/613,605, dated Feb. 13, 2008.

Australian application No. 20239/99; Examiner's Report dated Oct. 3, 2001 (Parent).

Australian application No. 20239/99; Examiner's Report dated Nov. 14, 2001 (Parent).

Australian application No. 20239/99; Examiner's Report dated Apr. 2, 2003 (Parent).

Australian application No. 20239/99; Examiner's Report dated May 13, 2003 (Parent).

Australian application No. 20239/99; Letters Patent dated Mar. 18, 2004.

Australian application No. 2003213537; Examiners Report dated May 23, 2005 (Div1).

Canadian Application No. 2,316,080; Examiner's Report dated Jul. 14, 2003.

Canadian Application No. 2,316,080; Examiner's Report dated Mar. 31, 2005.

Chinese Application No. 98813255.9; Office Action dated Oct. 10, 2003.

Chinese Application No. 98813255.9; Office Action dated Oct. 26, 2007.

Chinese Application No. 98813255.9; Notice of Allowance dated Apr. 25, 2008.

European Regional Application No. 98 965 046.0; dated Feb. 23, 2004.

European Regional Application No. 98 965 046.0; dated Nov. 15, 2004.

European Regional Application No. 98 965 046.0; dated Jun. 27, 2005.

European Application No. 98965045.0; Office Action dated Feb. 16, 2007.

European Application No. 98965045.0; Notice of Grant dated Mar. 5, 2008.

European Application No. 2006-18565; Office Action dated Jun. 24, 2008.

Great Britain application No. GB-0016132.3; Examination Report dated Apr. 9, 2002 (Parent).

Great Britain application No. GB-0016132.3; Examination Report dated Nov. 1, 2002 (Parent).

Great Britain application No. GB-0016132.3; Examination Report dated Feb. 10, 2003 (Parent).

Great Britain application No. GB-0016132.3; Examination Report dated Mar. 25, 2003 (Parent).

Great Britain application No. GB-0016132.3; Examination Report dated Apr. 9, 2003 (Parent).

Great Britain application No. GB-0016132.3; Certificate of Grant of Patent No. GB 2350619 dated Jun. 4, 2003 (Parent).

Great Britain application No. GB-0300479.3; Combined Search and Examination Report dated Feb. 13, 2003 (Div1).

Great Britain application No. GB-0300479.3; Examination Report dated Mar. 28, 2003 (Div1).

Great Britain application No. GB-0300479.3; Examination Report dated Apr. 10, 2003 (Div1).

Great Britain application No. GB-0300479.3; Certificate of Grant of Patent No. GB2381005 dated Jun. 4, 2004 (Div1).
Great Britain application No. GB-0300478.5; Combined Search and Examination Report dated Feb. 13, 2003 (Div2).
Great Britain application No. GB-0300478.5; Examination Report dated Mar. 26, 2003 (Div2).
Great Britain application No. GB-0300478.5; Certificate of Grant of Patent No. GB2381004 dated Jun. 4, 2004 (Div2).
Great Britain application No. GB-0300480.1; Combined Search and Examination Report dated Feb. 13, 2003 (Div3).
Great Britain application No. GB-0300480.1; Examination Report dated Apr. 2, 2003 (Div3).
Great Britain application No. GB-0300480.1; Examination Report dated Apr. 17, 2003 (Div3).
Great Britain application No. GB-0300480.1; Certificate of Grant of Patent No. GB2381006 (Div3).
German Application No. 198 82 943.4-41; Office Action dated Apr. 26, 2002.
Japanese Application No. 2000-526614; Notice of Reasons for Rejection dated May 25, 2004.
Japanese Application No. 2000-526614; Notice of Reasons for Rejection dated May 24, 2006.
Japanese Application No. 2000-526614; Notice of Reasons for Rejection dated Feb. 21, 2007.
Japanese Application No. 2002-044035; Notice of Reasons for Rejection dated Jun. 25, 2008.
Japanese Application No. 2002-044035; Notice of Reasons for Rejection dated May 24, 2006.
New Zealand Application No. 505330; Examination Report dated May 16, 2001 (Parent).
New Zealand Application No. 505330; Examination Report dated Nov. 28, 2002 (Parent).
New Zealand Application No. 505330; Grant of Patent dated Jun. 9, 2003 (Parent).
New Zealand Application No. 522607; Examination Report dated Nov. 21, 2002 (Div1).
New Zealand Application No. 522607; Examination Report dated Mar. 8, 2004 (Div1).
New Zealand Application No. 522607; Examination Report dated May 19, 2004 (Div1).
New Zealand Application No. 522607; Grant of Patent dated Jun. 8, 2006 (Div1).
New Zealand Application No. 532939; Letters Patent dated Jun. 8, 2006 (Div2).
Norweigen Application No. 20003424; Office Action dated May 31, 2007.
Norweigen Application No. 20003424; Office Action dated Feb. 13, 2008.
Russian Application No. 2000120216/13; Official Action dated Jan. 28, 2003.
Russian Application No. 2000120216/13; Official Action dated Oct. 27, 2003.
Russian Application No. 2000120216/13; Official Action dated May 25, 2005.
Russian Application No. 2000120216/13; Official Action dated Mar. 24, 2006.
Norweigen Application No. 20003424; Office Action dated Jan. 27, 2009.
Johnson, L.A., et al., "Sex Preselection in Rabbits: Live Births from X and Y Sperm Separated by DNA and Cell Sorting", Execptional Paper-Rapid Publication, XP-002103476, Biology of Reproduction 41, 199-203, 1989, pp. 199-203.
XP-002103478, File Biosis, one page.
Nowshari, et al, Theriogenology 43:797-802, 1995.

* cited by examiner

MULTIPLE SEXED EMBRYO PRODUCTION SYSTEM FOR BOVINE MAMMALS

This application is a continuation of U.S. application Ser. No. 09/448,643, filed Nov. 24, 1999, now issued as U.S. Pat. No. 6,372,422 which was a continuation of U.S. application Ser. No. 09/015,454, filed Jan. 29, 1998, now issued as U.S. Pat. No. 6,071,689 which was a continuation-in-part of U.S. application Ser. No. 09/001,394, filed Dec. 31, 1997, now issued as U.S. Pat. No. 6,149,867, each hereby incorporated by reference.

BACKGROUND OF THE INVENTION

This invention relates generally to the field of sex selection in mammalian offspring. It is especially relevant to the aspect of low dose artificial insemination for creating the desired sex of offspring. Particularly, the invention relates to systems for sorting sperm via flow cytometry for sex-specific and low dose efforts at artificial insemination or the like.

For ages it has been desired to select the sex of specific offspring. Beyond obvious psychological aspects, the actual sex selection of mammalian offspring has significant economic s consequences when one considers its application to food producing animals such as cattle as well as celebrated trophy animals such as horses and the like. This great desire has resulted in a significant variety of efforts to achieve sex-selected offspring. Probably the effort which has appeared most likely to achieve the desired results has been efforts at sorting and selecting between X and Y sperm prior to insemination.

One of the challenges that effort at sorting X and Y sperm has faced is the large numbers of sperm involved. In natural insemination sperm are produced in some species by the billions; in artificial insemination less, but still significantly large numbers of sperm are used. For instance, artificial insemination techniques commonly use ten million to five hundred million sperm (depending on species). Thus a significant number of sperm are necessary even in an artificial insemination environment.

Many methods have been attempted to achieve the separation of X- and Y-chromosome bearing sperm. These methods have ranged from magnetic techniques such as appears disclosed in U.S. Pat. No. 4,276,139 to columnar techniques as appears disclosed in U.S. Pat. No. 5,514,537 to gravimetric techniques as discussed in U.S. Pat. Nos. 3,894,529, Reissue Pat. No. 32350, U.S. Pat. Nos. 4,092,229, 4,067,965, and 4,155,831. Electrical properties have also been attempted as shown in U.S. Pat. No. 4,083,957 as well as a combination of electrical and gravimetric properties as discussed in U.S. Pat. No. 4,225,405, 4,698,142, and 4,749,458. Motility efforts have also been attempted as shown in U.S. Pat. Nos. 4,009,260 and 4,339,434. Chemical techniques such as those shown in U.S. Pat. Nos. 4,511,661 and 4,999,283 (involving monoclonal antibodies) and U.S. Pat. Nos. 5,021,244, 5,346,990, 5,439,362, and 5,660,997 (involving membrane proteins), and U.S. Pat. Nos. 3,687,803, 4,191,749, 4,448,767, and 4,680,258 (involving antibodies) as well as the addition of serum components as shown in U.S. Pat. No. 4,085,205. While each of these techniques has been presented as if to be highly efficient, in fact at present none of those techniques yield the desired level of sex preselection.

At present, the only quantitative technique used to achieve the separation of X- and Y-chromosome bearing sperm has been that involving individual discrimination and separation of the sperm through the techniques of flow cytometry. This technique appeared possible as a result of advances and discoveries involving the differential dye absorption of X- and Y-chromosome bearing sperm. This was discussed early in U.S. Pat. No. 4,362,246 and significantly expanded upon through the techniques disclosed by Lawrence Johnson in U.S. Pat. No. 5,135,759. The Johnson technique of utilizing flow cytometry to separate X- and Y- chromosome bearing sperm has been so significant an advancement that it has for the first time made the commercial separation of such sperm feasible. While still experimental, separation has been significantly enhanced through the utilization of high speed flow cytometers such as the MoFlo® flow cytometer produced by Cytomation, Inc. and discussed in a variety of other patents including U.S. Pat. Nos. 5,150,313, 5,602,039, 5,602,349, and 5,643,796 as well as international PCT patent publication WO 96/12171. While the utilization of Cytomation's MoFlo® cytometers has permitted great increases in speed, and while these speed increases are particularly relevant given the high number of sperm often used, certain problems have still remained. In spite of the almost ten-fold advances in speed possible by the MoFlo® flow cytometer, shorter and shorter sorting times have been desired for several reasons. First, it has been discovered that as a practical matter, the sperm are time-critical cells. They loose their effectiveness the longer they remain unused. Second, the collection, sorting, and insemination timings has made speed an item of high commercial importance. Thus, the time critical nature of the sperm cells and the process has made speed an essential element in achieving high efficacy and success rates.

Other problems also exist ranging from the practical to the theoretical. On the practical side, it has been desired to achieve sex-sorted sperm samples using inexpensive disposable components and substances. Also on the expense side, it has been desired to be able to achieve sorting (as well as collection and insemination) in as efficient a labor event as possible. Thus, for commercial production and success in this field, improvements which might only represent an increase in efficiency may still be significant. Related to the practical aspect of expense, is the practical aspect of the delicateness and sensitivity of the entire process. In this regard, it has been desired to simplify the process and make it as procedurally robust as possible so that operator error or skill can play an ever decreasing role.

In addition to the delicateness of the process, it has always been known that the sperm themselves are extremely delicate cells. While this factor at first glance seems like it might be considered easily understood, in fact, the full extent of the cells' sensitivities have not yet been fully explored. In the context of flow cytometry in general, most sorted cells or particles have often been spherical or otherwise physically able to withstand a variety of abuses. This is not the case for sperm cells. In fact, as the present invention discloses, the processing through normal flow cytometer techniques may, in fact, be unacceptable for cytometric sorting of sperm cells in certain applications. The sensitivities range from dilution problems and the flow cytometer's inherent need to isolate and distinguish each cell individually as well as the pressure and other stresses which typical flow cytometry has, prior to the present invention, imposed upon the cells or other substances that it was sorting. This may also represent a unique factor for sperm cells because it appears that even though the sperm cell may appear to pass through the flow cytometer and be sorted with no visually discernable side-effects, in fact, the cells themselves may have been stressed to the point that they perform less than optimally in the insemination process. Thus, an interplay of factors seems involved and has raised unusual problems from the perspective of sperm cell sorting and ultimate use for artificial insemination.

Another problem which has remained—in spite of the great advances achieved through the Johnson patent and related technology—is the fact that prior to the present invention it has been extremely difficult to achieve lower dosage insemination with sexed sperm. While historically, some achievement of low dose insemination has occurred, it has appeared to be more on a theoretical or laboratory environment rather than from environments which are likely to be experienced in or applicable to a commercial application. In this regard, the desire has not been merely to achieve low dose insemination but rather to achieve low dose insemination with pregnancy success rates which are comparable to existing unsexed, high dosage artificial insemination efforts. Thus, the advances achieved by the present inventors in both sexed and low dose artificial insemination represent significant advances which may, for the first time, make commercial applications feasible.

Another problem which has been faced by those in the industry—again, in spite of the great advances by the Johnson patent and related technology—is the fact that the problem itself, namely, artificial insemination with a high success rate is one of a statistical nature in which a multitude of factors seem to interplay. Thus, the solutions proposed may to some degree involve a combination of factors which, when thoroughly statistically studied, will be shown to be necessary either in isolation or in combination with other factors. Such a determination is further compounded by the fact that the results themselves vary by species and may be difficult to ascertain due to the fact that testing and statistical sampling on a large enough data base is not likely to be worth the effort at the initial stages. For these reasons the invention can also involve a combination of factors which may, individually or in combination, represent the appropriate solutions for a given application. This disclosure is thus to be considered broad enough so that the various combinations and permeations of the techniques disclosed may be achieved. Undiscovered synergies may exist with other factors. Such factors may range from factors within the sorting or flow cytometer steps to those in the collection as well as insemination steps. At present, studies have been primarily achieved on bovine species, however, it is not believed that these techniques will be limited to such species or, for that matter to only sperm cells. It appears that the techniques used may have application beyond just sperm cells into areas which involve either sensitive items to be sorted or merely minimization of the impacts of the stresses of flow cytometry upon the item sorted.

Interestingly, while the present invention takes an approach to minimize the impacts and stresses upon the sperm cells, others appear to have actually taken steps away from this direction by increasing pressures and demands for speed and other such performance. Essentially, the drive for low dose insemination and high speed processing may, in an individual or perhaps interrelated fashion have posed problems which limited one another. Thus, while there has been a long felt but unsatisfied need for high speed, low dose sexed insemination, and while the implementing arts and elements have long been available, prior to the present invention the advances or perhaps combinations of advances had apparently been overlooked by those skilled in the art. Perhaps to some degree they failed to appreciate that the problem involved an interplay of factors as well as peculiar necessities for the types of cells (sperm cells or perhaps species-specific sperm cells) involved in this field. Interestingly, as the listing of efforts earlier in this discussion shows, substantial attempts had been made but they apparently failed to understand the problem inherent in such an area as low dose, sexed insemination and had perhaps assumed that because the natural service event involves perhaps billions of sperm, there may have been physical limitations to the achievement of artificial insemination with numbers which are as many as four orders of magnitude less in number. Thus, it may not be surprising that there was to some extent an actual teaching away from the technical direction in which the present inventors went. Perhaps the results may even be considered unexpected to a degree because they have shown that sexed, low dose artificial insemination can be achieved with success rates comparable to those of unsexed, high dose artificial insemination. It might even be surprising to some that the techniques and advances of the present invention in fact combine to achieve the great results shown. While each technique could, in isolation, be viewed by some as unremarkable, in fact, the subtle changes appear to afford significant advances in the end result—whether considered alone or in combination with other subtle changes.

Thus, until the present invention the achievement of success rates for low dose, sexed artificial insemination has not been possible with levels of performance necessary or simplified procedures likely to be necessary to achieve commercial implementation. The present invention discloses techniques which permit the achievement of improved performances and thus facilitate the end result desired, namely, low dose, sexed artificial insemination on a commercial basis.

SUMMARY OF THE INENTION

Accordingly, the present invention provides improved sheath and collector systems for sorting of sperm cells to determine their sex through a flow cytometer. The sheath fluid as typically used in a flow cytometer is replaced with a fluid which minimizes the stress on the sperm cells as they are sorted. Furthermore, the collection system is improved to minimize both the physical and chemical stress to which the sperm cells are subjected. Various techniques and substances are represented but as those skilled in the art will readily understand, various combinations and permutations can be used in the manner which may be optimized for performance based in the species, goals and other parameters involved in a specific processing application.

An object of the invention is thus to achieve better sorting for substances such as sperm cells. A goal is to minimize the impact the sorting function itself has on the cells or other sensitive items which may be sorted. A particular goal is to minimize the impact the sheath fluid imposes upon the cells and to potentially provide a sheath fluid which affirmatively acts to assist the cells in handling the various stresses involved. A parallel goal is to provide substances and techniques which are especially suited for sperm cells in general, for bovine sperm cells, for equine sperm cells, and for the separation of such sperm cells into X- and Y-chromosome bearing components. Similarly a goal is to minimize the impacts that the collection phase (e.g., after sorting) has upon the cells and to minimize the physical impact as well as chemical impacts on such sex sorted sperm cells. Thus a goal is to achieve as unaffected a sorted result as possible.

Another object of the invention is to achieve low dose, sorted insemination on levels and with success rates which are comparable to those of the typical unsexed, high dose artificial insemination. Thus the prior goals of minimizing the stress or potential damage upon the sperm cells is important. Sorting in a manner which affords both high speed and low stress sorting, and which is especially adapted for sperm cell sorting in a low dose context is an important goal as well. The goals of providing sheath and other fluids which do not negatively affect the fertility of the sperm and which are compatible with artificial insemination are also important.

Naturally further objects of the invention are disclosed throughout other areas of the specification and claims.

BRIEF DESCRIPTON OF DRAWINGS

DETAILED DESCRIPON OF THE PREFERRED EMBODIMENT

As will be seen, the basic concepts of the present invention can be combined and embodied in a variety of ways. The invention involves both improved flow cytometer systems as well as systems for the creation of sex-specific sperm samples which may be used in artificial insemination and the animals produced by such techniques. Furthermore, the techniques are disclosed in a general fashion so that they may be applied to specific systems and applications once the general principals are understood. While device enhancements are disclosed it should be understood that these enhancements not only accomplish certain methods but also can be varied and combined in a number of ways. Importantly, as to all of the foregoing, each of these facets should be understood to be encompassed by this disclosure.

As mentioned, the basic goal is that of separating the X-bearing sperm from the Y-bearing sperm. This is done in a manner which isolates the two types of sperm so that each can be separately packaged and dealt with. The isolation is preferably done through the use of flow cytometry. Flow cytometry in general is a technique which is well understood. For instance, the basic aspects of it are shown and discussed in a variety of patents to Cytomation, Inc. such as the U.S. Patents and other publications listed earlier. Each of these patents and the references cited therein, are incorporated by reference, thus those skilled in the art can easily understand the basic principles involved.

Figure 1:
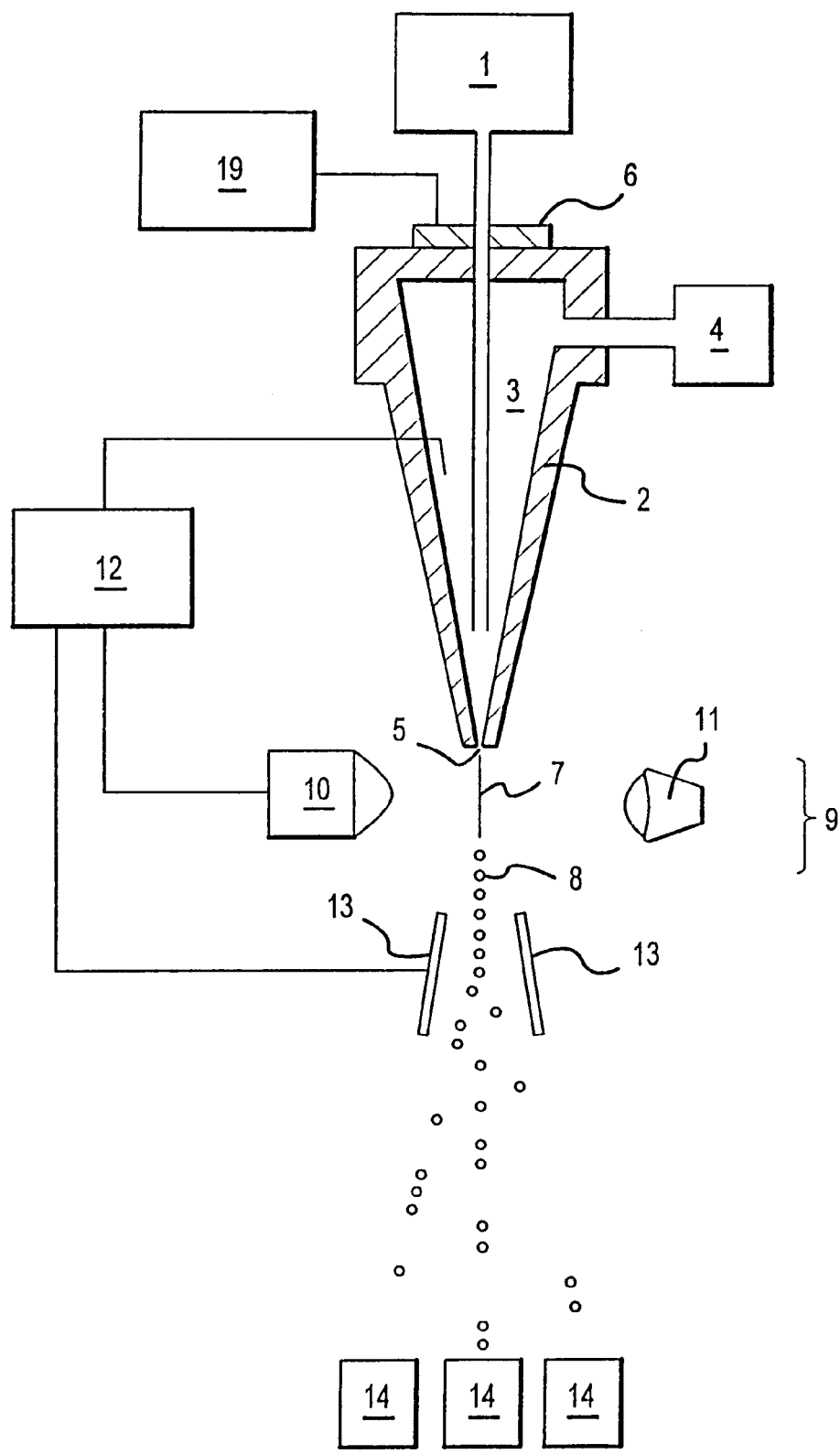
FIG. 1 is a schematic diagram of a sorter system according to the present invention.

Essentially, flow cytometry involves sorting items, such as cells, which are provided to the flow cytometer instrument through some type of cell source. A conceptual instrument is shown in FIG. 1. The flow cytometer instrument includes a cell source (1) which acts to establish or supply cells or some other type of item to be analyzed by the flow cytometer. The cells are deposited within a nozzle (2) in a manner such that the cells are surrounded by a sheath fluid (3). The sheath fluid (3) is usually supplied by some sheath fluid source (4) so that as the cell source (1) supplies its cells, the sheath fluid (3) is concurrently fed through the nozzle (2). In this manner it can be easily understood how the sheath fluid (3) forms a sheath fluid environment for the cells.

Since the various fluids are provided to the flow cytometer at some pressure, they flow out of nozzle (2) and exit at the nozzle orifice (5). By providing some type of oscillator (6) which may be very precisely controlled through an oscillator control (19), pressure waves may be established within the nozzle (2) and transmitted to the fluids exiting the nozzle (2) at nozzle orifice (5). Since the oscillator (6) thus acts upon the sheath fluid (3), the stream (7) exiting the nozzle orifice (5) eventually and regularly forms drops (8). Because the cells are surrounded by a sheath fluid environment, the drops (8) may contain within them individually isolated (generally) cells or other items.

Since the drops (8) generally contain isolated cells, the flow cytometer can distinguish and separate droplets based upon whether or not the appropriate cell or cells is/are contained within the drop. This is accomplished through a cell sensing system (9). The cell sensing system involves at least some type of sensor (10) which responds to the cells contained within each drop (8) as discussed at length in the seminal work (no pun intended) by Larry Johnson, namely, U.S. Pat. No. 5,135,759. As the Johnson patent explains for sperm cells, the cell sensing system (9) may cause an action depending upon the relative presence or relative absence of a particular dye which may be excited by some stimulant such as the laser exciter (11). While each type of sperm cell is stained by the dye, the differing length of the X-chromosome and the Y-chromosome causes different levels of staining, Thus, by sensing the degree of dye present in the sperm cells it is possible to discriminate between X-bearing sperm and Y-bearing sperm by their differing emission levels.

In order to achieve the ultimate separation and isolation of the appropriate cells, the signals received by sensor (10) are fed to some type of sorter discrimination system (12) which very rapidly makes the decision and can differentially charge each drop (8) based upon whether it has decided that the desired cell does or does not exist within that drop (8). In this manner the sorter discrimination system (12) acts to permit the electrostatic deflection plates (13) to deflect drops (8) based on whether or not they contain the appropriate cell or other item. As a result, the flow cytometer acts to sort the cells by causing them to land in one or more collectors (14). Thus by sensing some property of the cells or other items the flow cytometer can discriminate between cells based on a particular characteristic and place them in the appropriate collector (14). In the system presently used to sort sperm, the X-bearing sperm droplets are charged positively and thus deflect in one direction, the Y-bearing sperm droplets are charged negatively and thus deflect the other way, and the wasted stream (that is unsortable cells) is uncharged and thus is collected in an undeflected stream into a suction tube or the like.

Figure 2:
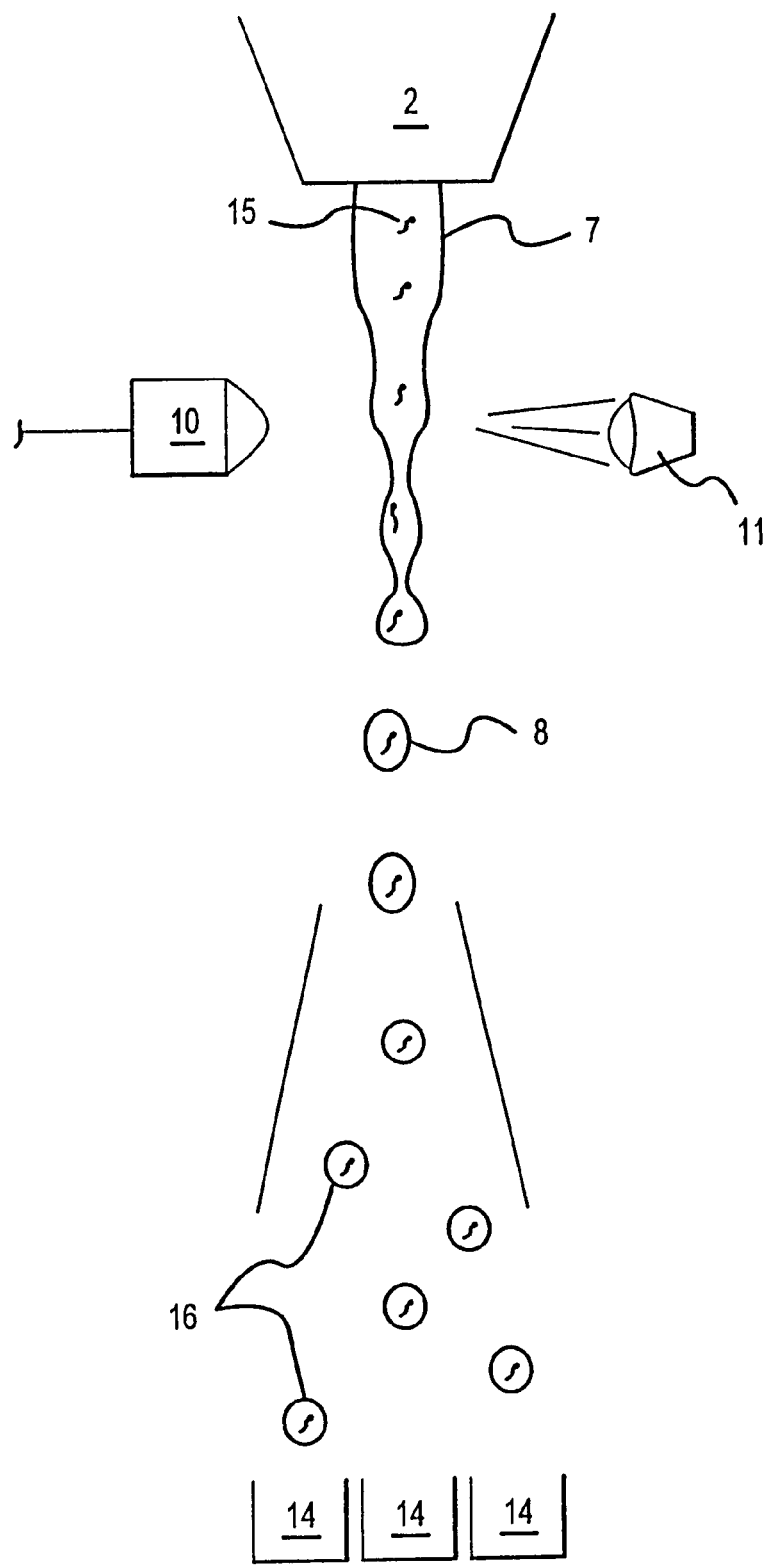
FIG. 2 is a diagram of the entrained cells in the free fall area of a typical flow cytometer.

Referring to FIG. 2, the process can be even further understood. As shown in that figure, the nozzle (2) emits a stream (7) which because of the oscillator (6) (not shown in FIG. 2) forms drops (8). Since the cell source (1) (not shown in FIG. 2) may supply sperm cells (15) which have been stained according to the Johnson technique, the light stimulation by laser exciter (11) is differentially determined by sensor (10) so that the existence or nonexistence of a charge on each drop (8) as it separates from stream (7) can be controlled by the flow cytometer. This control results in positively charged, negatively charged, and uncharged drops (8) based upon their content. As shown in FIG. 2, certain drops are shown as deflected drops (16). These deflected drops (16) are those containing sperm cells (15) of the one or the other sex. They are then deposited in the appropriate collector (14) for later use.

One of the aspects of flow cytometry which is particularly important to its application for sperm sorting is the high speed operation of a flow cytometer. Advances have been particularly made by the flow cytometers available through Cytomation, Inc. under the MoFlo® trademark. These flow cytometers have increased sorting speeds extraordinarily and have thus made flow cytometry a technique which is likely to make feasible the commercial application of sperm sorting (among other commercial applications). They act to achieve high speed sorting, that is at a speed which is notably higher than those otherwise utilized. Specifically, Cytomation's MoFlo® flow cytometers act with oscillator frequencies of greater than about five kilohertz and more specifically can be operated in the 10 to 30 or even the 50 kilohertz ranges. Thus droplets are formed at very high frequencies and the cells contained within the sheath fluid environment can be emitted very rapidly from the nozzle (2). As a result, each of the components such as the nozzle (2) oscillator (6), and the like which make up and are part of a flow cytometer system result in a high speed cell sorter. In the application of a high speed cell sorter to the sorting of sperm cells, sorting at rates of greater than about 500 sorts per second is achieved. In fact, rates of sorting in the thousand and twelve hundred ranges have already been achieved through a high speed cell sorter. Importantly, it should be understood that the term "high speed" is a relative term such that as other advances in flow cytometry and specific applications are achieved, the aspect which is considered "high" may be varied or may remain absolute. In either definition, the general principle is that the sorting may occur at rates at which the parameters and physical characteristics of the flow cytometer are significant to the cells themselves when sorting particular cells such as sperm cells.

One aspect of high speed sorting which appears to come into play when sorting sperm cells is that of the pressures and other stresses to which the sperm cells are subjected within the flow cytometer. For instance, when operating at high speeds (and an alternative definition of "high speed"), flow cytometers can be operated at a pressure of 50 pounds per square inch and even 60 and higher pounds per square inch. These pressures may be considered high because they may result in effects upon the cells being sorted. The key as disclosed in the present invention for this facet is the fact that the stress thresholds of the particular cells are the determining factor. Additionally as further knowledge is gained it may be shown that the stress thresholds are a function of combined effects such as the particular species or the particular prior or subsequent handling of the cells. The key in this regard is that the stress imposed upon the cells can, in fact, alter their viability and their ability to achieve the desired result. In the pressure case, it may be that merely subjecting the sperm cells to a higher pressure as a result of the operation of the flow cytometer at that pressure may result in decreased performance of the cells. The present invention in one regard acts to minimize these stresses and thus results in greater efficacies as well as lower dosages as discussed later.

In considering the stress aspect of the cells, the present invention acts in a fashion which minimizes the stresses. These stresses can be minimized at any point in the over all cycle or process of collecting, sorting or even inseminating the animal. Importantly, the stress imposed by the handling of the cells within the flow cytometer appears significant for this application. In one embodiment of the invention, the sheath fluid is specifically selected so that it can serve in a coordinated fashion with both (or either) the pre-sort cell fluid environment or the post-sort cell fluid environment. While naturally it is possible to adjust either the pre- or post-sort fluids, in one embodiment the invention adjusts the sheath fluid (3) so that it imposes significantly less stress upon the cells than was previously accomplished. In one regard the invention is remarkable in that it removes the total focus from that of operation of the flow cytometer to a focus on handling and removing stress from the cells themselves. For instance, while it has been known to utilize fluids having a proper pH factor or osmoality, the present invention recognizes that there may be certain chemical compositions to which the cells may be hyper-responsive. These hyper-responsive chemical compositions may naturally vary based upon the cells or even the prior handling of the cells. Importantly at present it appears that for sperm cells certain metabolic chemical compositions such as citrate seem to prevent unusually high stresses upon the cells. Thus, the hyper-responsive chemical compositions can be defined as those to which the cells are particularly responsive in the context of their functionality and the then-existing handling techniques. As to sperm cells it appears that metabolic compositions, specifically citrate constancy for bovine sperm cells and hepes buffer constancy for equine sperm cells may be very important. Thus the present invention acts to minimize the changes through the type of operation or the selection of substances which may act as a means for minimizing the changes which the cells experience.

Figure 3:
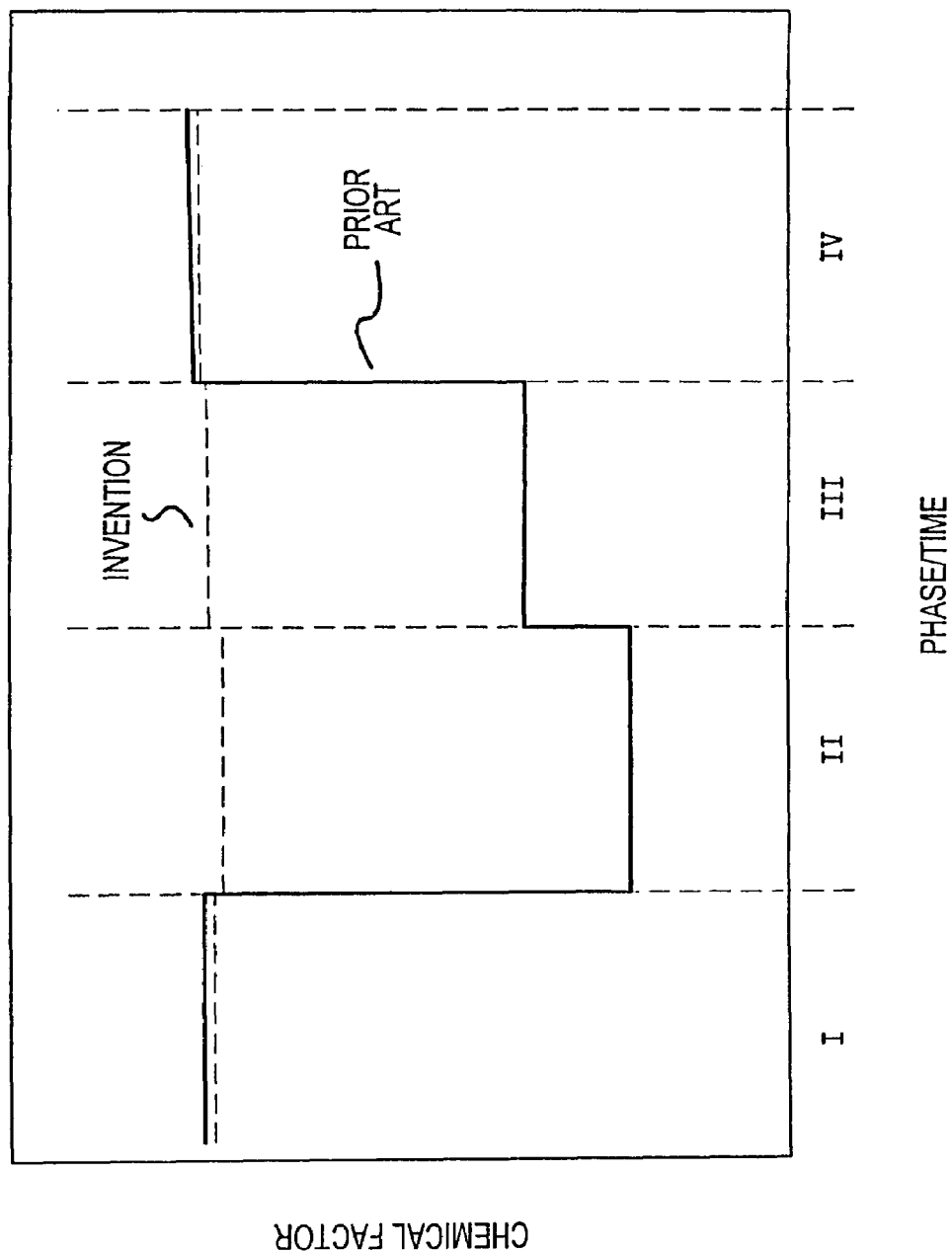
FIG. 3 is a conceptual diagram showing differences as they roughly appear as a result of the present invention.

For the sheath fluid, a substance is selected according to one embodiment of the invention so that it may be chemically coordinated to prevent minimal changes. Thus, by selecting the appropriate sheath fluid not only in context of flow cytometry parameters, but rather also in context of the cell parameters themselves, the changes experienced by the cells and the over all result of the sorting can be enhanced. This is shown conceptually in FIG. 3. FIG. 3 shows some type of chemical factor (such as citrate or other factors) as it may exist throughout the various phases of the process. For instance, the four phases shown might represent the following: phase I may represent the existence of the cells within the cell source (1), phase II might show the existence of the cells as they are sorted in the sheath fluid environment, phase III might show the cells as they are collected after sorting and phase IV might show the reconstituted cells in a storage medium after sorting. These four phases as shown for the prior art may experience vastly different chemical factor environments. As shown conceptually, however, in the present invention the cells may experience very little change, most notably the dip or drop experienced between phases I and II may be virtually absent. This is as a result of the selection of the appropriate sheath fluid as mentioned above. Thus, as a result of being subjected to an appropriate sheath fluid, the cells in the present invention may experience a much lower level of stress.

One of the potential generalities that may exist with respect to this phenomenon is the fact that certain chemical compositions may represent more hyper-responsive chemical compositions than others. While naturally this may vary based upon the species of sperm, the handling, or even the type of cell involved, it appears that the viability of the cells for their intended purpose (here, artificial insemination) varies greatly, naturally or because of sorting or both, and so the cells exhibit a hyper-responsive character with respect to that chemical composition. By selecting certain metabolic chemical compositions, most notably citrates or chemicals which are within the citric acid cycle, great advances appear possible. Thus for the bovine sperm application, the sheath fluid (3) is selected and coordinated so that it presents about a 2.9 percent sodium citrate composition. Specifically, the 2.9 percent sodium citrate solution may be created as follows:

1. Place 29.0 grams of sodium citrate dihydrate ($Na_3C_6H_5O_7 \cdot 2H_2O$) in a 1,000 ml volumetric flask
   a. Dissolve sodium citrate in ¾ of water batch, then add water to volume.
2. Add deionized or Nanopure water to make 1,000 ml final volume.
3. Transfer to bottles and autoclave at 15 lbs pressure (245° F.) for at least 30 minutes
   a. Autoclave solution using conditions to minimize evaporation (loose cover)
   b. Be careful that water does not boil away.

4. Cool slowly at room temperature.

5. Store sealed in a 5° C. cold room.

Further, for a sheath fluid, the sodium citrate solution may be filtered.

6. Filter with a 0.22 micron filter using aseptic techniques.

Interestingly, for equine sperm cells such a composition does not perform as well. Rather, it has been discovered that for equine sperm cells, a hepes buffered medium such as a hepes bovine gamete medium—particularly HBGM3 as previously created by J. J. Parrish for a bovine application—works well. This medium is discussed in the article "Capacitation of Bovine Sperm by Heparin", 38 Biology of Reproduction 1171 (1988) hereby incorporated by reference. Not only is this surprising because it is not the same type of substance as is utilized for bovine sperm, but the actual buffer, originally was developed for a bovine application. Thus in the equine application the sheath fluid is selected which contains the hepes buffer. This solution may have a pH at room temperature of about 7.54 (pH at 39° C.=7.4) with the following composition:

| Chemical | Dry weight (g/500 ml) |
| --- | --- |
| $CaCl_2$ | 0.145 |
| $KCl_2$ | 0.115 |
| $MgCl_2 \cdot 6H_2O$ | 0.004 |
| $NaH_2PO_4 \cdot H_2O$ | 0.018 |
| NaCl | 2.525 |
| NaPyruvate | 0.011 |
| Lactic Acid (60%) | 1.84 ml |
| HEPES | 4.765 |
| $NaHCO_3$ | 0.420 |
| BSA (fraction V) | 3.0 |

One other aspect which may interplay in the present invention is the fact that the cells involved may experience unusual sensitivities. In one regard this may be due to the fact that sperm cells are in a class of cells which are non-repairing cells. That is, they do not have the ability to repair themselves and hence, they may need to be treated much more sensitively than is typical for flow cytometers or other handling equipment. Thus, it may be appropriate that the enhancement is particularly applicable when the flow cytometer acts to establish a source of sperm cells. Another potentially related aspect which may be unique to a class of cells such as sperm cells is the fact that their DNA is non-repairing, non-replicating, and non-transcribing. Either of these factors may come into play and so they may be relevant either individually or together. Thus, it may be that the teachings of the present invention apply to all gamete cells or even to viruses and the like which are non-repairing, non-translating, non-transcribing cells.

Figure 4:
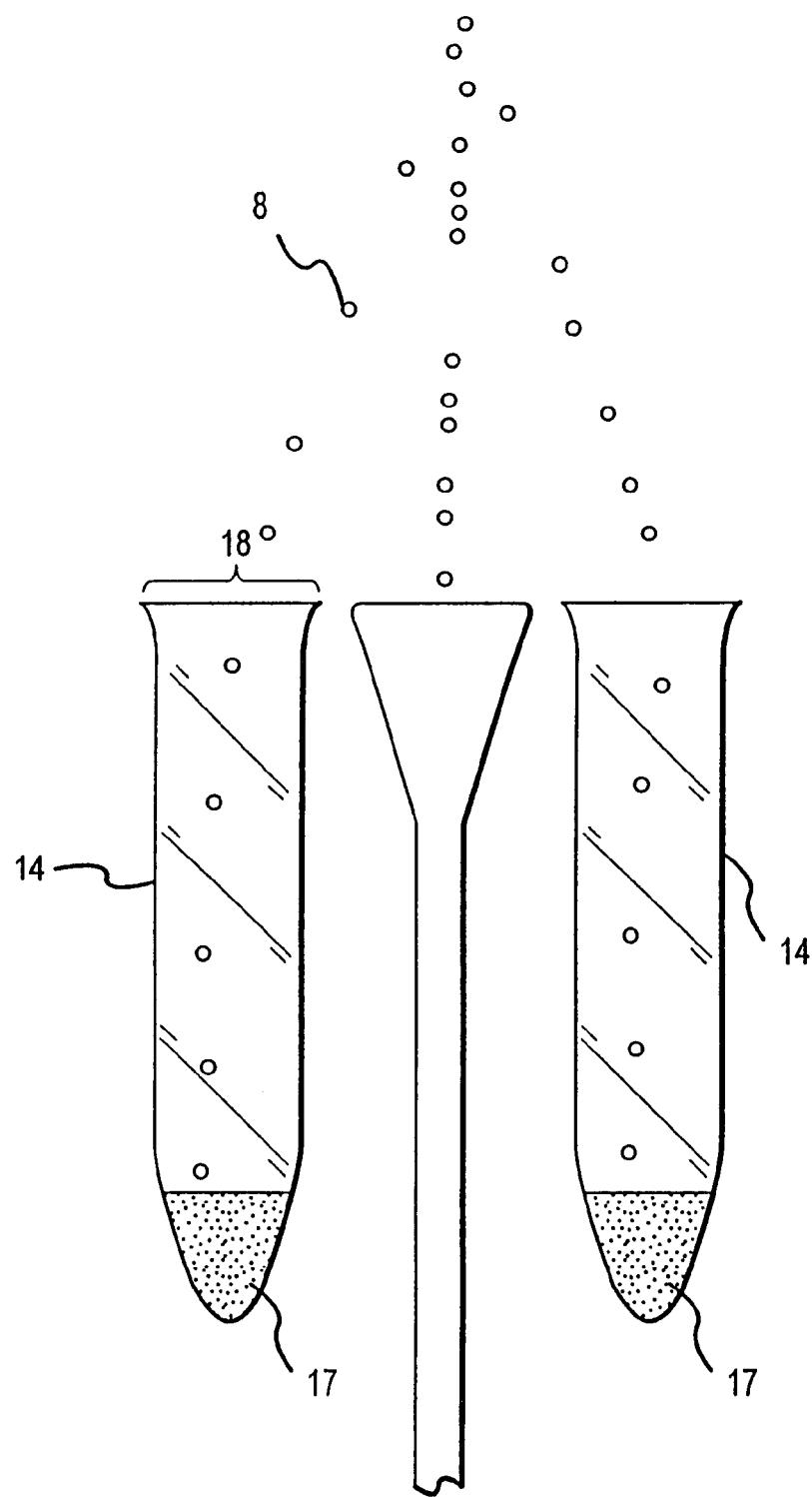
FIG. 4 is a diagram of the sorted cell stream as they are collected in the landing zone area.

A separate aspect of the flow cytometer processing which may also be important is the fact of properly treating the cells both chemically and physically after they are sorted. As shown in FIG. 4, as the cells within drops (8) land in collector (14), it may be important that the container which makes up the collector be properly sized so that it acts as some means of avoiding an impact between the cells and the container itself While it has been known to place an initial collector fluid (17) in the bottom of the container to collect the cells so that they do not hit the bottom of the container, it appears that a simple widening of the container to address variations in stream presentation as well as the inevitable splashing due to the impact of the cells into the container can be used to enhance the result. In one regard this can act as a cushioning element so that cells which may be mechanically delicate, that is, they may break or be damaged by an impact can be treated appropriately. Thus when the cytometer source establishes cells which are physically delicate cells as the cells to be sorted, it may be important to provide some type of cushioning element such as a wide collection tube for which the opening width (18) serves to position the walls of the container in a manner which avoids contact with the cells. Thus the tube does not present side walls so close that there is any significant probability of contact between those cells being sorted and the walls of the tube. In this manner, in addition to the collector fluid (17), it may be desirable to include a wide collection tube as well. Perhaps merely providing a wide opening to the container which serves as part of the collector (14) may be sufficient. For applications utilizing high speed sorting of sperm cells, it has been found that providing a container having an inner diameter opening of at least 15 millimeters is believed to be sufficient. Specifically when utilizing a 14 ml Falcon test tube in such an application, minimal physical damage to the cells as a result of the collector (14) has been discovered.

It should be noted that even the 14 ml Falcon test tube may not be optimum. Specifically, it is believed that designing a collection container which matches the geometry of the stream (that is, a "stream-matched container") may be most optimal. This stream-matched container may have any or all of the following characteristics: a relatively wide orifice, an elliptically shaped orifice, a lesser height to width ratio than currently involved, an angled or otherwise coordinated presentation such as may present side walls which are parallel to the falling streams, and the like. It may also be desirable to provide a mounting element such as a movable element or medium like ball bearings or the like to permit variable orientation of the tube to match the falling stream desired to be collected. In addition, the physical characteristics for the class of containers such as the existing tube (described as a "Falcon-type" test tube) may include not only the width of the tube but also the material (such polystyrene to which the cells do not stick) out of which it is made and the like. (These material options are well known for the 14 ml Falcon tube.) Thus the container and it collection fluid may also serve as a cushioning element to minimize physical damage to the cells. It also can serve, by its size, to facilitate collection of adequate numbers of sperm without a significant dilution effect.

Another aspect of the collector fluid (17) can be the fact that it, too, may serve to minimize chemical stresses upon the cells. In one regard, since it may be important to provide a nutrient to the cells both before and after sorting, the collector fluid (17) may be selected so as to provide a coordinated level of nutrient so that the levels are balanced both before and after sorting. For bovine sperm in which a nutrient of egg yolk citrate is utilized at a two percent egg yolk level, it has been discovered that utilizing a six percent egg yolk citrate level (that is six percent egg yolk content in a citrate solution) provides good results. This is as result of the volumes existing before and after the sorting event. The collector fluid (17) may start (before sorting) with about 2 ml of volume. The sorting event may add about double this volume (ending at three times the initial starting volume) with very little egg yolk citrate in solution (due to clogging and other flow cytometer considerations). Thus, the end result in terms of the level of the amount of egg yolk citrate present may be equivalent to the starting result, namely, two percent egg yolk content in a citrate solution due to the volumes involved. Thus the collector fluid (17) may be selected so as to create an ending collector fluid environment which is balanced with the initial nutrient or other fluid environment. In this manner, it may serve to minimize the time and changed level of composition to which the cells are subjected. Naturally, these fluid environments may be presented within the flow cytometer or may exist at some other prior time, the important point being merely minimizing the stress to which the cells are subjected at any time in their life cycle. Furthermore, since the initial chemical substance content can be varied (for instance the percent egg yolk content in the citrate may be varied up or down), likewise the starting collection fluid environment or various volumes may also be varied so that the ending result is the same. Thus, prior to commencing the sorting process, the collector fluid exists with a six percent egg yolk content in the citrate solution and after completion of the sorting event the collector fluid—with the sex-specific sperm—may result in a two percent egg yolk content in the citrate solution similar to the initial nutrient content.

Note that in later use these sperm cells may be treated to a 20% egg yolk content in the citrate fluid for other reasons, however these changes are not deemed to provide stress to the cells as they are merely a known part of the total insemination process. While naturally the levels may be varied as those skilled in the art readily understand, a 20% egg yolk citrate buffer may be constituted as follows:

I. FINAL COMPOSITION:
  80% sodium citrate solution (72 mM)
  20% (vol/vol) egg-yolk II. PREPARATION FOR 1 LITER:
  A. Sodium citrate solution
    1. Place 29.0 grams of sodium citrate dihydrate ($Na_3C_6O_7 \cdot 2H_2O$) in a 1,000 ml volumetric flask
    2. Add deionized or Nanopure water to make 1,000 ml final volume.
    3. Transfer to bottles and autoclave at 15 lbs pressure (245° F.) for at least 30 minutes.
      a. Autoclave solution using conditions to minimize evaporation (loose cover)
      b. Be careful that water does not boil away.
    4. Cool slowly at room temperature.
    5. Store sealed in a 5° C. cold room.
  B. Egg preparation
    1. Obtain fresh hen's eggs from a good commercial source.
    2. Wash the eggs free of dirt ('do not use too much detergent) and rinse.
    3. Immerse eggs in 70% ethanol for 2-5 minutes.
    4. Remove eggs and allow to dry (or wipe dry) and store on a clean towel.
  C. Preparation of extender
    1. Use sterile, clean glassware
    2. A-fraction (non-glycerol fraction)
      a. Place 800 ml of 2.9% sodium citrate solution in a 1,000 ml graduated cylinder.
      b. Antibiotic levels for the non-glycerol containing fraction (A-fraction) of the extender may be as follows:
        I. Tylosin=100 µg/ml
        ii. Gentamicin=500 µg/ml
        iii. Linco-spectin=300/600 µg/ml
      c. Add 200 ml of fresh egg-yolk as outlined below (Section D)
        I. Mix very thoroughly.
      d. This provides A-fraction extender based on 2.9% sodium citrate, with 20% egg-yolk and antibiotics at concentrations known to be non-toxic to bull sperm.
      e. Extender can be stored overnight at 5° C.
      f. Decant supernatant (upper 800 ml) the next day.
      g. Warm to 37° C. prior to use the next day.
  D. To add egg-yolk to a buffered solution, the following procedure works well.
    1. Wash egg and clean the eggs (see B above)
    2. Open egg and separate yolk from albumin using a yolk separator. Alternatively, pour yolk back and forth 2-3 times between the two half shells. Do not rupture the membrane around the yolk.
    3. Place the yolk onto a sterile piece of 15 cm filter paper.
    4. Hold the filter paper over the graduated cylinder containing buffer and squeeze the yolk (rupturing the membrane) and allow the yolk to run out of the golded filter paper into the cylinder. Typically about 12-15 ml of the yolk can be obtained from one egg.

Another aspect which may interplay in the various factors of the present invention is that of utilizing low dose amounts of sperm for artificial insemination or the like. Additional background on the aspect of sexed, artificial insemination may be found in "Prospects for Sorting Mammalian Sperm" by Rupert P. Amman and George E. Seidel, Jr., Colorado Associated University Press (1982) hereby incorporated by reference. As mentioned, natural insemination involves numbers of sperm on the order of billions of sperm. Typical artificial insemination is presently conducted with millions of sperm for bovine species and hundreds of millions of sperm for equine species. By the term "low dose" it is meant that the dosage of sperm utilized in the insemination event are less than one-half or preferably even less than about 10% of the typical number of sperm provided in a typical artificial insemination event. Thus, the term "low dose" is to be viewed in the context of the typical artificial insemination dosage or also as an absolute number. For bovine sperm where currently 1 to 10 million sperm are provided, a low dose process may be considered an absolute number of about 500,000 sperm or perhaps as low as 300,000 sperm or lower. In fact, through utilization of the techniques of the present invention, artificial insemination with good percentages of success has been shown with levels of insemination of sperm at 100,000 and 250,000 sperm (41% and 50%, respectively pregnancy rates). As shown in the article "Uterine Horn Insemination of Heifers With Very Low Numbers of Non-frozen and Sexed Spermatozoa" as published in 48 Theriogenology 1255 (1997) hereby incorporated by reference. Since sperm cells appear to display a sensitivity to dilution, these results may display particular interdependence on the utilization of low dose sperm samples with regards to various techniques of the present invention. The absolute numbers may be species dependent, for equine species, merely less than about ten, five, or even one million sperm may be considered a low dose process.

Another aspect which may be important is the fact that the sperm sexed through the present invention techniques is utilized in an artificial insemination system. Thus, when the collector (14) is used to provide sperm for artificial insemination the techniques of the present invention may be particularly relevant. Further, it is possible that the combination of both artificial insemination use and the use in a low dose environment may together create synergies which makes the various techniques of the present invention particularly appropriate. Naturally, the sexed sperm can be utilized not just in an artificial insemination mode, but in other techniques such as in vitro fertilization and the like.

The process of collecting, sorting, and eventually inseminating an animal through the use of flow cytometry involves a variety of steps. In the context of bovine insemination, first the semen is collected from the bull through the use of an artificial vagina. This occurs at rates of approximately 1.5 billion sperm per ml. This neat semen may be checked through the use of a spectrophotometer to assess concentration and may be microscopically evaluated to assure that it meets appropriate motility and viability standards. Antibiotics may then be added. As a result the initial sample may have approximately 60 to 70 percent of the progressively motile sperm per ejaculate. For processing, a dilution through of some type TALP (tyrode albumin lactate pyruvate) may be used to get the numbers of sperm at a manageable level (for flow analysis) of approximately 100 million per ml. The TALP not only nurtures the sperm cells, but it may make them hyper-activated for the staining step. Prior to staining, in some species such as the equine species, centrifugation may be accomplished. Staining may be accomplished according to a multi-stained or single-stained protocol, the latter, the subject of the Johnson Patent and related technology. The staining may be accomplished while also adjusting the extender to create the appropriate nutrient environment. In bovine applications this may involve adding approximately 20% egg yolk content in a citrate solution immediately after staining. Further, in staining the sperm cells, it has been discovered that by using higher amounts of stain than might to some extent be expected better results may be achieved. This high concentration staining may involve using amounts of stain in the tens of micro-molar content such as discussed in the examples below where 38 micro-molar content of Hoechst 33342 stain was used.

After adding the stain, an incubation period may be used such as incubating at one hour at 34° C. to hasten the dye uptake with concentrations at about 100 million sperm cells per ml. Filtration may then be accomplished to remove clumps of sperm cells and then dilution or extending may or may not be accomplished to the desired sort concentration of approximately 100 million sperm cells per ml may be accomplished. Sorting according to the various techniques discussed earlier may then be accomplished from which sperm cells may be recovered in the collection phase. As mentioned earlier, the collection may result in samples with approximately 2% egg yolk citrate concentrate content (for bovine species). This sample may then be concentrated to about 3-5 million sperm cells per ml through the use of centrifugation after which the sheath fluid and preserving fluid may be removed. A final extension may then be accomplished with either 20% egg yolk citrate or a Cornell Universal Extender or the like. The Cornell Universal Extender may have the following composition for 1000 ml:

14.5 g sodium citrate dihydrate
2.1 g NaHCO$_3$
0.4 g KCl
3.0 g glucose
9.37 g glycine
0.87 g citric acid
For 20% egg-yolk using 800 ml of above preparation and may include about 200 ml of egg-yolk composition.

After this last extending, 3 to 5 million sperm per ml (for bovine species) may result. This sample may then be cooled to slow the sperm's metabolism and to permit use over longer periods of time. In the equine species the sample may then be used in oviductal or other insemination processes as those skilled in the art well understand. In bovine sperm, the sample may be diluted yet one more time to the desired dosage level. It has been discovered that dilution may create an effect upon the sperm cell's viability and so it may be appropriate to avoid too large a level of dilution by providing a smaller sample. At present, low dosages of approximately 300,000 sperm per 0.184 ml may be achieved. Furthermore, it may be desirable to maintain a level of seminal plasma at approximately a five percent level, although the results of this requirement are, at present, mixed. The sperm cell specimen may then be placed in a straw for use in artificial insemination and may be transported to the cows or heifers to be inseminated.

In order to achieve conveniently timed artificial insemination, heifer or cow estrus may be synchronized using known techniques such as the utilization of prostaglandin F2$_\alpha$ according to techniques well known in the art. This latter substance may be particularly valuable in that it has been reported to potentially achieve enhanced fertility in heifers as discussed in the article "Prostoglandin F2$_\alpha$—A Fertility Drug in Dairy Cattle?", 18 Tneriogenology 245 (1982) hereby incorporated by reference. While recent results have not maintained this premise, it may be that the present invention demonstrates its particular viability in situations of sexed, low dose insemination. For bovine species, artificial insemination may then be accomplished through the use of embryo transfer equipment with placement of the sperm cells deep within the uterine horns. This may be accomplished not at the peak moment as typically used in artificial insemination, but rather at a somewhat later moment such as 12 hours after that time since there is some possibility that fertility for sexed artificial insemination may occur slightly later. The utilization of embryo transfer equipment may be used because there may be high sensitivity of the uterine wall for such low dose, sexed inseminations.

Further the techniques can be combined to achieve higher efficiency production as well. Particularly, the processes now invented which permit high speed sorting and low dose insemination of sexed embryos is also possible in a superovulated animal. The superovulation may be achieved by use of a superovulatory pharmaceutical or by any other technique. The superovulatory pharmaceutical may act directly or indirectly, such as through a sequence of reactions to achieve a greater than normal production of eggs. The combination with superovulation is surprising because superovulation was previously deemed to hinder such a combination. Sperm transport is compromised in superovulated cattle, so, animals were frequently artificially inseminated on multiple occasions and/or with multiple doses of semen. Also, prior procedures for sexing semen were relatively slow; therefore, it was of interest to determine fertilization rates after a single insemination of superovulatory pharmaceutical, such as FSH (follicle stimulating hormone)-treated cattle with only 600,000 total sexed unfrozen sperm using these newer combination of techniques.

By example, twelve Angus crossbred heifers were superovulated using standard procedures: 6, 6, 4, 4, 2, 2, 2, and 2 mg FSH were injected intramuscularly at half-day intervals beginning between days 9 and 12 of the estrous cycle; 25 and 12.5 mg prostaglandin F-2 alpha were injected intramuscularly with the 6th and 7th FSH injections. Sperm from bulls of unknown fertility were stained with Hoechst 33342 and then sorted using a MoFlo® flow cytometer/cell sorter yielding 700-800 live sperm of each sex/sec. Average sort purity was 89% of the desired sex. Sorted sperm were concentrated to 3.36×10$^6$ sperm/ml by centrifugation at 650 g for 10 min, cooled to 5° C., and stored 4 h. Then 184 ul were loaded in 0.25 ml plastic straws; half the dose was inseminated into each uterine horn 20 to 24 h post-onset of estrus using automatic side-opening embryo transfer sheaths. Embryos were collected by standard non-surgical procedures at 7 or 16 days post-estrus. Results were similar between day 7 and 16 collections and between X- and Y-sorted sperm Embryos were recovered from 9 heifers. There were 52 embryos (mean, 4.3-5.3/donor) at normal stages of development, 13 retarded embryos and 31 unfertilized ova. Forty-six embryos were sexed by PCR using primers for a Y-chromosome-specific DNA sequence; 43 (93%) were of the intended sex. Although this study involved few animals, surprisingly, insemination of superovulated heifers with only 600,000 total (live) sexed unfrozen sperm gave similar results to conventional procedures. Variations on the above may also be accomplished, including, but not limited to, sorting through other than flow cytometric means, achieving superovulation in other manners, increasing fertility in other manners, and the like.

Further, the congruence of methods of sexing sperm based on DNA content, high speed flow cytometer/cell sorters, and procedures for inseminating heifers with fewer than 500,000 total sperm without compromising fertility has resulted in the possibility of a viable sexed semen industry in cattle within a few years. There will be a myriad of applications for sperm sexed at <85% accuracy. Perhaps the most obvious is inseminating one subset of cattle (both dairy and beef) for female herd replacements, and having the converse subset (both dairy and beef) bred to entirely different types of bulls to produced males for meat. A very important subset of the above is inseminating heifers with X-chromosome-bearing sperm to produce female calves, which have a lower incidence of dystocia than male calves, primarily due to smaller size. Furthermore, proving young dairy sires would be much more efficient with a preponderance of heifer calves. Having more than 85% heifer calves also makes it feasible to manage dairy cows so they average fewer than two surviving calves per lifetime, which is attractive because of reducing problems associated with gestation and parturition. Single sex systems of beef production also would become feasible, in which each female replaces herself and is slaughtered between 2 and 3 years of age, thus using a much higher percentage of nutrients in the system for growth, and a lower percentage for maintenance. Sexed semen would be useful for in vitro fertilization and to inseminate cows superovulated for embryo transfer. Frequently one sex of calves is considerably more valuable than the other, and although accurate methods of sexing embryos are available, they are time-consuming, and half of the embryos produced are of the less valuable sex, it is surmised that accurately sexed semen would be widely adopted for artificial insemination of cattle if the sexing surcharge were low and fertility was only minimally compromised. The percentage of beef cattle inseminated artificially likely would increase substantially with sexed semen.

Interestingly, rather than inseminating within the uterine body where such insemination are usually placed, by insemination deep within the uterine horn, better results may be achieved. Perhaps it is also surprising that the samples thus far studied have shown no difference between ipsi- and contra-lateral inseminations when accomplished deep within the uterine horn. By deep, it should be understood that the insertion is placed well into the uterine horn using the embryo transfer equipment. The fact that results do not appear significantly different using ipsi- and contra-lateral inseminations has led the present inventors to propose the use of insemination in both so that the process of identifying the appropriate uterine horn may no longer be needed.

As a result of the insemination, it is of course desired that an animal of the desired sex be produce This animal may be produced according to the systems discussed earlier through the use of the sexed sperm specimen. It should also be understood that the techniques of the present invention may find application in other techniques such as laproscopic insemination, oviductal insemination, or the like.

As examples, the following experiments have been conducted. While not all use every aspect of the inventions described here, they do show the performance enhancements possible through differing aspects of the invention Further, a summary of some experiments is contained in the article "Uterine Horn Insemination of Heifers With Very Low Numbers of Non-frozen and Sexed Spermatozoa" as referenced earlier. This article summarizes some of the data showing the efficacy of the present invention. As to the experiments, one has been conducted with sexed, unfrozen sperm cells with high success as follows:

EXAMPLE 1

Angus heifers 13-14 mo of age and in moderate body condition, were synchronized with 25 mg of prostaglandin F-2 alpha at 12-day intervals and inseminated 6-26 h after observed standing estrus. Freshly collected semen from three 14-26 mo old bulls was incubated in 38 µM Hoechst 33342 at $75 \times 10^6$ sperm/ml in a TALP medium for 1 h at 34° C. Sperm were sorted by sex chromosomes on the basis of epifloures-cence from laser excitation at 351 and 364 nm at 150 mW using a MoFlo® flow cytometer/cell sorter operating at 50 psi and using 2.9% Na citrate as sheath fluid. X chromosome-bearing sperm (~90% purity as verified by resorting sonicated sperm aliquots) were collected at ~500 live sperm/sec into 2-ml Eppendorf tubes containing 100 µl Cornell Universal Extender (CUE) with 20% egg yolk. Collected sperm were centrifuged at 600×g for 10 min and resuspended to $1.63 \times 10^6$ live sperm/ml in CUE. For a liquid semen unsexed control; Hoechst 33342-stained sperm were diluted with sheath fluid to $9 \times 10^5$ sperm/ml and centrifuged and resuspended to $1.63 \times 10^6$ progressively motile sperm/ml in CUE. Sexed semen and liquid control semen were cooled to 5° C. over 75 min and loaded into 0.25-ml straws (184 ul/straw). Straws were transported at 3 to 5° C. in a temperature-controlled beverage cooler 240 km for insemination 5 to 9 h after sorting. Sexed semen and liquid control semen were inseminated using side-opening blue sheaths (IMV), one half of each straw into each uterine horn ($3 \times 10^5$ live sperm/heifer). As a standard control, semen from the same bulls had been frozen in 0.5-cc straws by standard procedures (mean $15.6 \times 10^6$ motile sperm/dose post-thaw), thawed at 35° C. for 30 sec, and inseminated into the uterine body. Treatments were balanced over the 3 bulls and 2 inseminators in a ratio of 3:2:2 inseminations for the sexed semen and two controls. Pregnancy was determined ultrasonically 31-34 days after insemination and confirmed 64-67 days later when fetuses also were sexed (blindly). Data are presented in the table.

| Treatment | No. Heifers bred | No. Pregnant d31-34 | No. Pregnant d64-67 | No female fetuses |
|---|---|---|---|---|
| Sexed semen | 45 | 20 (44%) | 19 (42%) | 18 (95%)[a] |
| Liquid control | 28 | 15 (54%) | 15 (54%) | 8 (53%)[b] |
| Frozen control | 29 | 16 (55%) | 15 (52%) | 12 (80%)[c] |

[a,b]Sex ratios of values with different superscripts differ (P <0.02).

Although the pregnancy rate with sexed semen was only 80% of controls, this difference was not statistically significant (>0.1). One pregnancy was lost by 64-67d in each of the sexed and dozen control groups; 18 of 19 fetuses (95%) were female in the sexed group, and 20 of 30 (67%) were female in the control groups. The liquid semen control yielded a virtually identical pregnancy rate to the frozen semen control containing over 50 times more motile sperm (over 120 times more total sperm), demonstrating the efficacy of low-dose insemination into the uterine horns. We have altered the sex ratio in cattle significantly using flow cytometer technology and artificial insemination.

Similarly, an experiment was conducted with unsexed, unfrozen sperm cells and may be reported as follows:

EXAMPLE 2

The objective was to determine pregnancy rates when heifers are inseminated with extremely low numbers of frozen sperm under ideal field conditions. Semen from three Holstein bulls of above average fertility was extended in homogenized milk, 7% glycerol (CSS) extender plus 5% homologous seminal plasma to $2 \times 10^5$, $5 \times 10^5$ or $10 \times 10^6$ (control) total sperm per 0.25 ml French straw and frozen in moving liquid nitrogen vapor. Semen was thawed in 37° C. water for 20 sec. Holstein heifers 13-15 mo of age weighing 350-450 kg were injected with 25 mg prostaglandin F-2-alpha (Lutalyse®) twice at a 12-day interval and inseminated with an embryo transfer straw gun and sideopenig sheath, half of the semen deep into each uterine horn 12 or 24 h after detection of estrus. The experiment was done in five replicates over 5 months, and balanced over two insemination technicians. Ambient temperature at breeding was frequently –10 to –20° C., so care was taken to keep insemination equipment warm. Pregnancy was determined by detection of a viable fetus using ultrasound 40-44 days post-estrus and confirmed 55-62 days post-estrus; 4 of 202 conceptuses were lost between these times. Day 55-62 pregnancy rates were 55/103 (53%), 71/101, (70%), and 72/102 (71%) for $2 \times 10^5$, $5 \times 10^5$ and $10 \times 10^5$ total sperm/inseminate (P<0.1). Pregnancy rates were different (P<0.05) among bulls (59, 62, and 74%), but not between technicians (64 and 65%) or inseminations times post-estrus (65% for 12 h and 64% for 24 h, N=153 at each time). With the methods described, pregnancy rates in heifers were similar with $5 \times 10^5$ and $10 \times 10^6$ total sperm per inseminate.

Prior a experiment has also been conducted on sexed, unfrozen sperm cells and may be reported as follows:

EXAMPLE 3

Semen was collected from bulls at Atlantic Breeders Cooperative, diluted 1:4 with a HEPES-buffered extender ÷0.1% BSA, and transported 160 km (~2 HR) to Beltsville, Md. where it was sorted at ambient temperature by flow cytometry into a TEST yield (20%) extender using methods described previously (Biol Reprod 41:199). Sorting rates of up to $2 \times 10^6$ sperm of each sex per 5-6 h at ~90% purity were achieved. Sperm were concentrated by centrifugation (300 g for 4 min) to $2 \times 10^6$ sperm/ml. Some sperm were sorted into extender containing homologous seminal plasma (final concentration, 5%). Sorted sperm were shipped by air to Colorado (~2,600 km) and stored at either ambient temperature or 5° C. (cooled during shipping over 6 hr in an Equitainer, an insulated device with an ice-containing compartment). Heifers or dry cows detected in estrus 11 to 36 h earlier were inseminated within 9 to 29 h of the end of the sperm sorting session. Sperm (1 to $2 \times 10^5$ in 0.1 ml) were deposited deep in the uterine horn ipsilateral to the ovary with the largest follicle as determined by ultrasound at the time of insemination None of 10 females became pregnant when inseminated with sperm shipped and stored at ambient temperature. Of 29 females inseminated with sperm cooled to 5° C. during shipping, 14 were pregnant at 4 weeks of gestation, and 12 (41%) at 8 weeks. Eleven of the 22 inseminated within 10 h of the end of sorting were pregnant at 8 weeks, but only 1 of 7 inseminated 17-24 h after sorting was pregnant. There was no significant effect of adding seminal plasma. One of the 12 fetuses was not of the predicted sex, one was unclear, and 10 were of the predicted sex, as determined by ultrasonography at 60-70 days of gestation.

Subsequently, 33 additional heifers were inseminated with 0.05 ml (semen extended as described above) into each uterine horn without using ultrasonography, only 3 were pregnant 4 weeks after insemination, and only 1 remained pregnant at 8 weeks. However, different bulls were used from the previous group, and all inseminations were done 18-29 h post-sorting. An additional 38 heifers were inseminated similarly (~22 h post-sorting) 200 km from our laboratory with sorted sperm from another bull; none of these was pregnant 8 weeks after insemination.

To summarize it is possible to achieve pregnancies in cattle via artificial insemination of sperm sorted for sex chromosomes by flow cytometry, and the sex ratio of fetuses approximates that predicted by reanalysis of sorted sperm for DNA content (90%). However, pregnancy rates varied greatly in these preliminary experiments which required shipping sperm long distances. Fertility decreased drastically by 17 h post-sorting but there was some confounding because different bulls were used at the different times. Further studies are needed to determine whether variation observed in pregnancy rates was due to bull differences, insemination techniques, interval between sorting and insemination, or other factors.

Finally, an experiment also has been conducted with unsexed, unfrozen sperm cells and may be reported as follows:

EXAMPLE 4

The objective was to determine pregnancy rates when heifers were inseminated with very low numbers of sperm under ideal experimental conditions. Semen from three Holstein bulls was extended in Cornell Universal Extender plus 5% homologous seminal plasma to $1 \times 10^5$ or $2.5 \times 10^5$ sperm per 0.1 ml $2.5 \times 10^6$ total sperm per 0.25 ml was used as a control. Fully extended semen was packaged in modified 0.25 ml plastic French straws to deliver the 0.1 or 0.25 ml inseminate doses. Semen was cooled to 5° C. and used 26-57 h after collection. Holstein heifers 13-15 mo of age weighing 350-450 kg were injected with 25 mg prostaglandin F-2 alpha (Lutalyse®) at 12-day intervals and inseminated with an embryo transfer straw gun and side-opening sheath into one uterine horn 24 h alter detection of estrus. Insemination was ipsilateral to the side with the largest follicle determined by ultrasound 12 h after estrus; side of ovulation was verified by detection of a corpus luteum by ultrasound 7-9 days post-estrus. Pregnancy was determined by detection of a fetus by ultrasound 42-45 days post estrus. The experiment was done in four replicates and balanced over three insemination technicians. Side of ovulation was determined correctly in 205 of 225 heifers (91%); surprisingly, pregnancy rates were nearly identical for ipsilateral and contralateral inseminates. Pregnancy rates were 38/93 (41%), 45/87 (52%), and 25/45 (56%) for $1 \times 10^5$, $2.5 \times 10^5$ and $2.5 \times 10^6$ sperm/inseminate (P>0.1). There was a significant difference in pregnancy rate (P<0.05) among technician, but not among, bulls. With the methods described, it may be possible to reduce sperm numbers per inseminate sufficiently that sperm sorted by sex with a flow cytometer would have commercial application.

As mentioned and as can be seen from the various experiments, the field is statistically based and thus a variety of additional experiments may be conducted to show the appropriate combination and limitation strategies. Thus synergies among various affects will further be identified, such as instances in which the dye effects and combined dye effects the laser excitation may be studied.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims which may be submitted. It should be understood that a variety of changes may be made without departing from the essence of the invention. Such chances are also implicitly included in the description. They still fall within the scope of this invention. A broad disclosure encompassing both the explicit embodiment(s) shown, the great variety of implicit alternative embodiments, and the broad methods or processes and the like are encompassed by this disclosure.

In addition, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. As but one example of this aspect, the disclosure of a "collector" should be understood to encompass disclosure of the act of "collecting"—whether explicitly discussed or not—and, conversely, were there only disclosure of the act of collecting, such a disclosure should be understood to encompass disclosure of a "collector." Such changes and alternative terms are to be understood to be explicitly included in the description.

Any references mentioned in the application for this patent as well as all references listed in any information disclosure filed with the application are hereby incorporated by reference; however, to the extent statements might be considered inconsistent with the patenting of this/these invention(s) such statements are expressly not to be considered as made by the applicant(s).

We claim:

1. A method of producing multiple embryos from a female bovine mammal comprising:
    a. creating superovulation in said female bovine mammal to create at least two eggs in each of said female bovine mammal comprising the step of using an ovulatory pharmaceutical to cause multiple eggs to be produced in said female bovine mammal further comprising the steps of:
        i) injecting a dosage of follicle stimulating hormone in each of said female bovine mammal a plurality of times a day;
        ii) administering said dosage of follicle stimulating hormone with prostaglandin F-2-alpha;
    and wherein said step of injecting said dosage of follicle stimulating hormone in each of said female bovine mammal a plurality of times a day comprises injecting said follicle stimulating hormone in approximately half day increments at a dosage level of 6, 6, 4, 4, 2, 2, 2, and 2 mg between days 9 and 12 inclusive of the estrus cycle and wherein administering said dosage of follicle stimulating hormone with prostaglandin F-2-alpha comprises supplementing 25 and 12.5 mg of prostaglandin F-2-alpha on the sixth and seventh dosages, respectively, of said follicle stimulating hormone;
    b. collecting sperm cells from at least one male bovine mammal;
    c. staining said collected sperm cells with Hoechst 33342;
    d. sorting the stained sperm cells with a flow cytometer to yield live sperm cells of a desired sex;
    e. concentrating said live sperm cells of a desired sex;
    f. establishing an insemination sample having in the range of $1 \times 10^5$ to $6 \times 10^5$ live sperm cells of a desired sex;
    g. inserting said insemination sample into said female bovine mammal, half the dose into each uterine horn of said female bovine mammal, 20 to 24 hours post-onset of estrus for said female bovine mammal;
    h. fertilizing a plurality of said eggs in said female bovine mammal; and
    i. producing at least two embryos of a desired sex from said female bovine mammal in which a plurality of said eggs were fertilized.

2. A method of producing multiple embryos from a female bovine mammal as described in claim 1 and further comprising the step of separating sperm cells based on the amount of nuclear DNA each said sperm cell contains.

3. A method of producing multiple embryos from a female bovine mammal as described in claim 1, further comprising the step of allowing at least one said embryo to develop into an animal of a desired sex.

4. A method of producing multiple embryos from a female bovine mammal as described in claim 1, further comprising chemically coordinating a sheath fluid to create a sheath fluid environment for said cells which is coordinated with both a pre-sort and a post-sort cell fluid environment.

5. A method of producing multiple embryos from a female bovine mammal as described in claim 4, wherein chemically coordinating a sheath fluid to create a sheath fluid environment for said cells which is coordinated with both a pre-sort and a post-sort cell fluid environment comprises establishing a sheath fluid which contains citrate.

6. A method of producing multiple embryos from a female bovine mammal as described in claim 1, further comprising collecting said sperm cells of a desired sex and cushioning said sperm cells of a desired sex from impact with a collection container which has a wide opening.

7. A method of producing multiple embryos from a female bovine mammal as described in claim 1, wherein said sorting said stained sperm cells with a flow cytometer is performed at a rate of about 500 sorts per second.

8. A method of producing multiple embryos from a female bovine mammal as described in claim 1, wherein said sorting said stained sperm cells with a flow cytometer yields 700-800 live sperm of the desired sex per second.

9. A method of producing multiple embryos from a female bovine mammal as described in claim 1, wherein said concentrating said live sperm cells of a desired sex comprises concentrating the live sperm cells to a concentration of about $3\times10^6$ to $5\times10^6$ sperm per milliliter.

* * * * *